United States Patent
Parham et al.

(10) Patent No.: US 11,345,687 B2
(45) Date of Patent: May 31, 2022

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Thomas Eberle, Landau (DE); Anja Jatsch, Frankfurt am Main (DE); Tobias Grossmann, Darmstadt (DE); Jonas Kroeber, Frankfurt am Main (DE); Dominik Joosten, Frankfurt am Main (DE); Caroline Wern, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 392 days.

(21) Appl. No.: 16/348,175

(22) PCT Filed: Nov. 6, 2017

(86) PCT No.: PCT/EP2017/078269
§ 371 (c)(1),
(2) Date: May 8, 2019

(87) PCT Pub. No.: WO2018/087022
PCT Pub. Date: May 17, 2018

(65) Prior Publication Data
US 2019/0367494 A1    Dec. 5, 2019

(30) Foreign Application Priority Data
Nov. 9, 2016 (EP) ..................... 16197924

(51) Int. Cl.
| | | |
|---|---|---|
| *C07D 403/10* | (2006.01) | |
| *C07D 405/04* | (2006.01) | |
| *C07D 405/14* | (2006.01) | |
| *C07D 409/04* | (2006.01) | |
| *C07D 487/04* | (2006.01) | |
| *C07D 491/04* | (2006.01) | |
| *C07D 495/04* | (2006.01) | |
| *H01L 51/00* | (2006.01) | |
| *H01L 51/50* | (2006.01) | |
| *C07D 491/048* | (2006.01) | |

(52) U.S. Cl.
CPC ......... *C07D 405/14* (2013.01); *C07D 403/10* (2013.01); *C07D 405/04* (2013.01); *C07D 409/04* (2013.01); *C07D 487/04* (2013.01); *C07D 491/048* (2013.01); *C07D 495/04* (2013.01); *H01L 51/006* (2013.01); *H01L 51/0067* (2013.01); *H01L 51/0072* (2013.01); *H01L 51/0073* (2013.01); *H01L 51/0074* (2013.01); *H01L 51/5016* (2013.01); *H01L 51/5056* (2013.01); *H01L 51/5072* (2013.01)

(58) Field of Classification Search
CPC .............. C07D 209/82; C07D 491/147; C07D 493/14; C07D 495/14
See application file for complete search history.

(56) References Cited

U.S. PATENT DOCUMENTS

| | | |
|---|---|---|
| 7,935,434 B2 | 5/2011 | Tanaka et al. |
| 8,221,908 B2 | 7/2012 | Tanaka et al. |
| 9,818,948 B2 | 11/2017 | Jatsch et al. |
| 2013/0341602 A1* | 12/2013 | Hikime ............... H01L 51/0074 257/40 |
| 2015/0357579 A1 | 12/2015 | Itoi et al. |
| 2016/0197282 A1 | 7/2016 | Tanimoto et al. |
| 2018/0162843 A1* | 6/2018 | Parham ............... C07D 405/14 |
| 2019/0084967 A1 | 3/2019 | Parham et al. |

FOREIGN PATENT DOCUMENTS

| | | |
|---|---|---|
| EP | 2301921 A1 | 3/2011 |
| JP | 2012049518 A | 3/2012 |
| JP | 2013-243266 A | 12/2013 |
| JP | 2016149558 A | 8/2016 |
| WO | WO-2013041176 A1 | 3/2013 |
| WO | WO-2013109045 A1 | 7/2013 |
| WO | WO-2014097866 A1 | 6/2014 |
| WO | 2015/022987 A1 | 2/2015 |
| WO | WO-2015022988 A1 | 2/2015 |
| WO | 2015/140073 A1 | 9/2015 |
| WO | 2016/198144 A1 | 12/2016 |
| WO | WO-2017076485 A1 | 5/2017 |

OTHER PUBLICATIONS

International Search Report for PCT/EP2017/078269 dated Dec. 8, 2017.
Written Opinion of the International Searching Authority for PCT/EP2017/078269 dated Dec. 8, 2017.
International Preliminary Report on Patentability received for PCT Patent Application No. PCT/EP2017/078269, dated May 23, 2019, 15 ages (9 pages of English Translation and 6 pages of Original Document).

* cited by examiner

*Primary Examiner* — Vu A Nguyen
(74) *Attorney, Agent, or Firm* — Faegre Drinker Biddle & Reath LLP

(57) ABSTRACT

The present invention describes dibenzofuran compounds substituted by carbazole compounds, especially for use as triplet matrix materials in organic electroluminescent devices. The invention further relates to a process for preparing the compounds of the invention and to electronic devices comprising these.

11 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/078269, filed Nov. 6, 2017, which claims benefit of European Application No. 16197924.0, filed Nov. 9, 2016, both of which are incorporated herein by reference in their entirety.

The present invention describes dibenzofuran compounds substituted by carbazole compounds, especially for use as triplet matrix materials in organic electroluminescent devices. The invention further relates to a process for preparing the compounds of the invention and to electronic devices comprising these.

Emitting materials used in organic electroluminescent devices (OLEDs) with organic semiconductors as functional materials are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

According to the prior art, matrix materials used for phosphorescent emitters in organic electroluminescent devices include carbazole derivatives and dibenzofuran derivatives. JP 2012-049518, U.S. Pat. Nos. 7,935,434 and 8,221,908 disclose dibenzofuran derivatives substituted by two N-phenylcarbazolyl groups.

There is generally still a need for improvement in these materials for use as matrix materials, in aspects including the external quantum efficiency (EQE). It is therefore an object of the present invention to provide compounds suitable for use in a phosphorescent or fluorescent OLED, especially as matrix material. More particularly, it is an object of the present invention to provide matrix materials which are suitable for red-, yellow- and green-phosphorescing OLEDs and possibly also for blue-phosphorescing OLEDs, and which lead to long lifetime, good efficiency and low operating voltage. More particularly, it is an object of the present invention to provide materials that lead to an improved external quantum efficiency.

It has been found that, surprisingly, electroluminescent devices containing compounds of the formulae (1) to (4) below have improvements over the prior art, especially when used as matrix material for phosphorescent dopants.

The present invention therefore provides a compound of one of the following formulae (1), (2), (3) or (4):

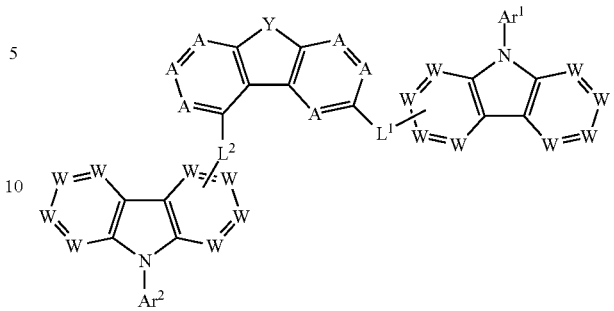

Formula (1)

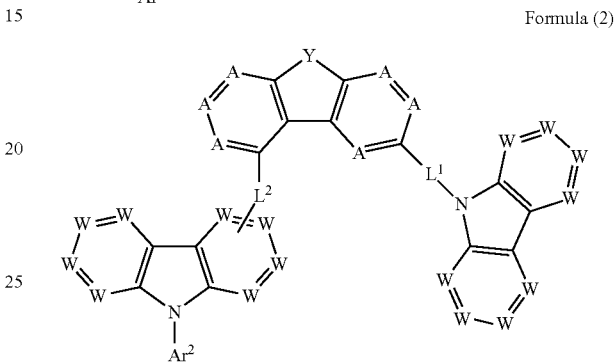

Formula (2)

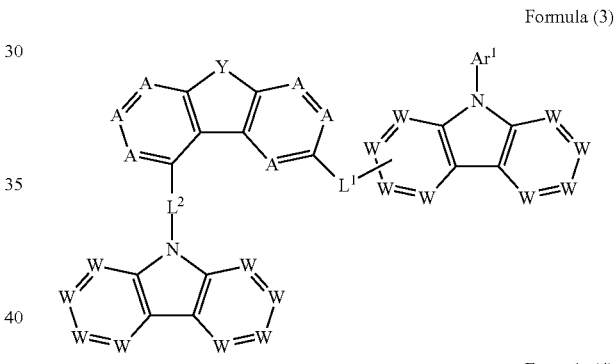

Formula (3)

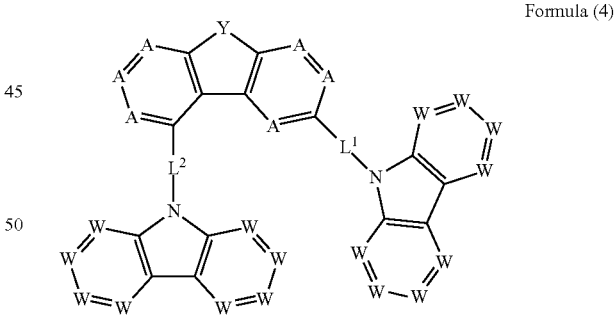

Formula (4)

where the symbols used are as follows:
A is the same or different at each instance and is CR' or N, where not more than two A groups per cycle are N, preferably not more than one A group per cycle is N;
Y is O or S;
W is the same or different at each instance and is CR or N, where not more than two W groups per cycle are N and where W is C when an $L^1$ or $L^2$ group is bonded to this position, or two adjacent W groups together are a group of the following formula (5) or (6) and the remaining W are the same or different at each instance and are CR or N, where each of the two carbazolyl derivative groups in the compound of the formula (1), (2), (3) or (4) has not more than two groups of the formula (5) or formula (6):

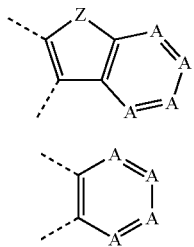

Formula (5)

Formula (6)

where the dotted bonds indicate the linkage of this group, A has definitions given above and Z is NR, CR$_2$, O or S;
with the proviso that one W group is CR and R at this position is a group of the following formula (7) or formula (8), or that two adjacent W groups are a group of the formula (5) or (6);

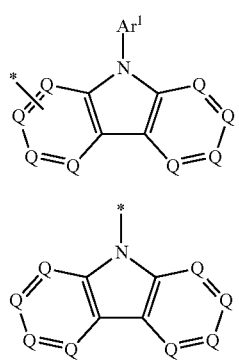

Formel (7)

Formul (8)

Q is the same or different at each instance and is CR$^1$ or N, where not more than two Q groups per cycle are N and where Q is C when the single bond to formula (1), (2), (3) or (4) is at this position, or two adjacent Q groups together are a group of the formula (5) or (6) and the remaining Q groups are the same or different at each instance, where the group of the formula (7) or formula (8) has not more than two groups of the formula (5) or formula (6), and A in the case of CR' is CR$^1$;
* is the single bond to formula (1), (2), (3) or (4);
Ar$^1$, Ar$^2$ is the same or different at each instance and is an aromatic ring system having 5 to 30 aromatic ring atoms or a dibenzofuran or dibenzothiophene group, where the aromatic ring system or the dibenzofuran or dibenzothiophene group may be substituted in each case by one or more nonaromatic R radicals;
L$^1$, L$^2$ is the same or different at each instance and is a single bond or an aromatic or heteroaromatic ring system which has 5 to 30 aromatic ring atoms and may be substituted by one or more R radicals;
R, R' is the same or different at each instance and is selected from the group consisting of H, D, F, Cl, Br, I, CN, NO$_2$, N(R$^1$)$_2$, C(=O)R$^1$, P(=O)(R$^1$)$_2$P(R$^1$)$_2$, B(R$^1$)$_2$, Si(R$^1$)$_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more R$^1$ radicals, where one or more nonadjacent CH$_2$ groups may be replaced by R$^1$C=CR$^1$, Si(R$^1$)$_2$, C=O, C=S, C=NR$^1$, P(=O)(R$^1$), SO, SO$_2$, NR$^1$, O, S or CONR$^1$ and where one or more hydrogen atoms may be replaced by D, F, Cl, Br, I, CN or NO$_2$, an aromatic or heteroaromatic ring system which has 5 to 40 aromatic ring atoms and may be substituted in each case by one or more R$^1$ radicals, or an aryloxy or heteroaryloxy group which has 5 to 40 aromatic ring atoms and may be substituted by one or more R$^1$ radicals; at the same time, it is optionally possible for two R substituents bonded to the same carbon atom or to adjacent carbon atoms, or two R' substituents bonded to adjacent carbon atoms, to form a monocyclic or polycyclic, aliphatic, aromatic or heteroaromatic ring system which may be substituted by one or more R$^1$ radicals;
R$^1$ is the same or different at each instance and is selected from the group consisting of H, D, F, Cl, Br, I, CN, N(R$^2$)$_2$, C(=O)R$^2$, a straight-chain alkyl group having 1 to 10 carbon atoms or a branched or cyclic alkyl group having 3 to 10 carbon atoms or an alkenyl group having 2 to 10 carbon atoms, each of which may be substituted by one or more R$^2$ radicals, where one or more hydrogen atoms may be replaced by D, F, Cl, Br, I or CN, or an aromatic or heteroaromatic ring system which has 5 to 40 aromatic ring atoms and may be substituted in each case by one or more R$^2$ radicals; at the same time, it is optionally possible for two R$^1$ substituents bonded to the same carbon atom or to adjacent carbon atoms to form a monocyclic or polycyclic, aliphatic, aromatic or heteroaromatic ring system which may be substituted by one or more R$^2$ radicals;
R$^2$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, CN and which may be substituted by one or more alkyl groups each having 1 to 4 carbon atoms; at the same time, it is possible for two or more adjacent R$^2$ substituents together to form a mono- or polycyclic, aliphatic ring system.

Adjacent carbon atoms in the context of the present invention are carbon atoms bonded directly to one another.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

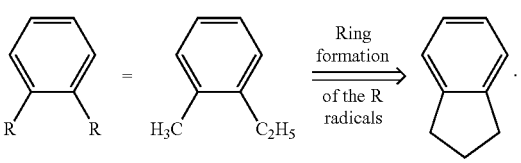

In addition, however, the abovementioned wording shall also be understood to mean that, if one of the two radicals is hydrogen, the second radical binds to the position to which the hydrogen atom was bonded, forming a ring. This shall be illustrated by the following scheme:

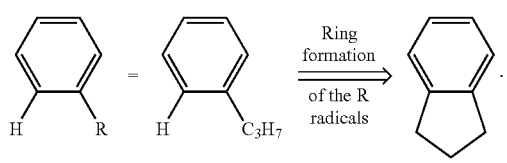

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S, where the heteroaryl group preferably contains not more than three heteroatoms. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

A fused aryl group in the context of the present invention is a group in which two or more aromatic groups are fused, i.e. annelated, to one another along a common edge, as, for example, in naphthalene. By contrast, for example, fluorene is not a fused aryl group in the context of the present invention, since the two aromatic groups in fluorene do not have a common edge.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S, where the heteroaromatic ring system preferably contains not more than four heteroatoms, more preferably not more than three heteroatoms. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are interrupted, for example, by a linear or cyclic alkyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{20}$-alkyl group in which individual hydrogen atoms or $CH_2$ groups may also be substituted by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to the compounds of the following formulae (1a), (2a), (3a) and (4a):

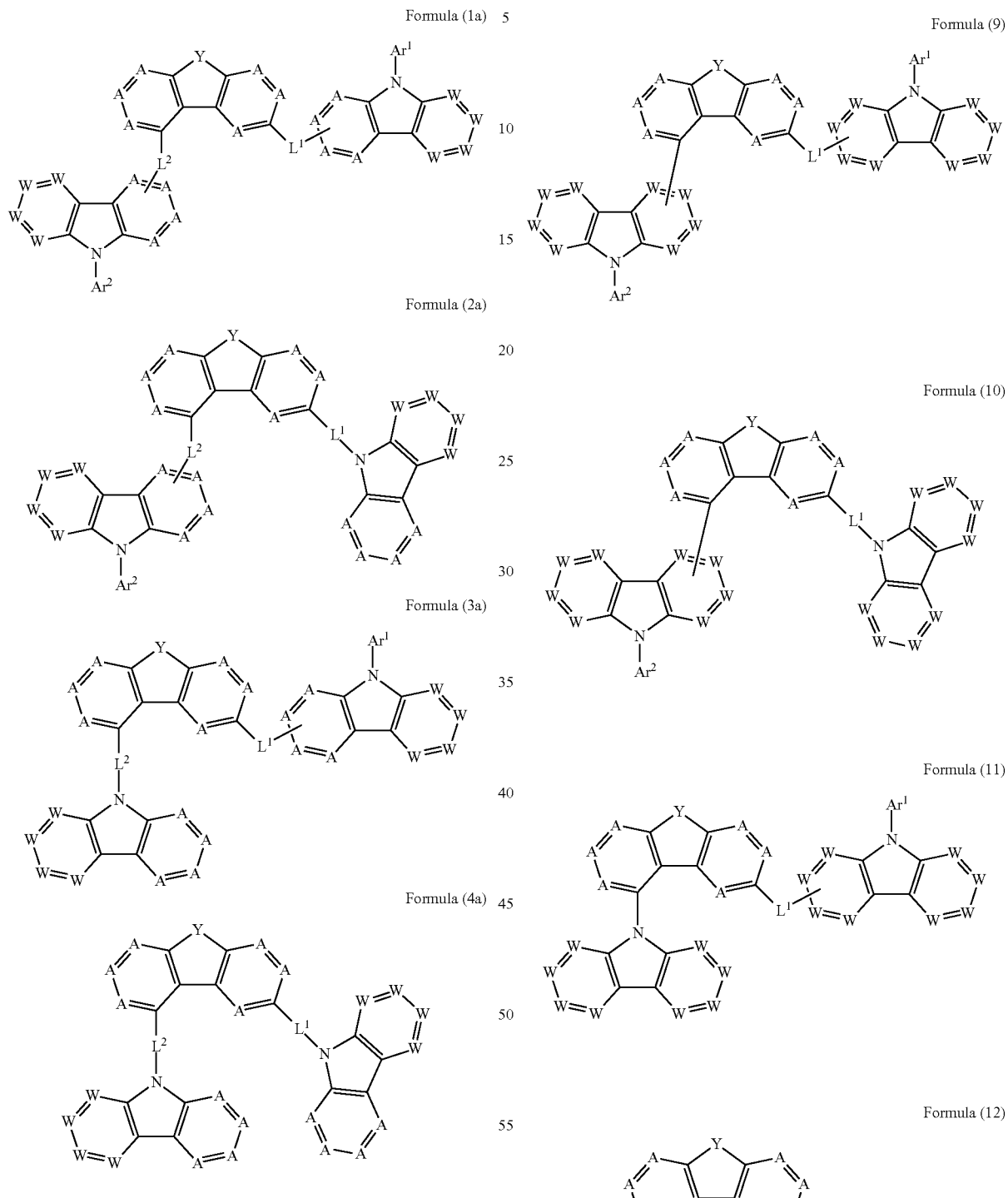

where the symbols used have the definitions given above and A is C when an $L^1$ or $L^2$ group is bonded to this position.

In a preferred embodiment of the invention, the $L^2$ group is a single bond. A preferred embodiment of the compound of the formula (1) is thus a compound of the following formula (9), and a preferred embodiment of the compound of the formula (1a) is a compound of the formula (9a). The same applies to the compounds of the formulae (2), (3) and (4), for which the compounds of the formulae (10), (11) and (12), or (2a), (3a) and (4a), for which the compounds (10a), (11a) and (12a) are preferred:

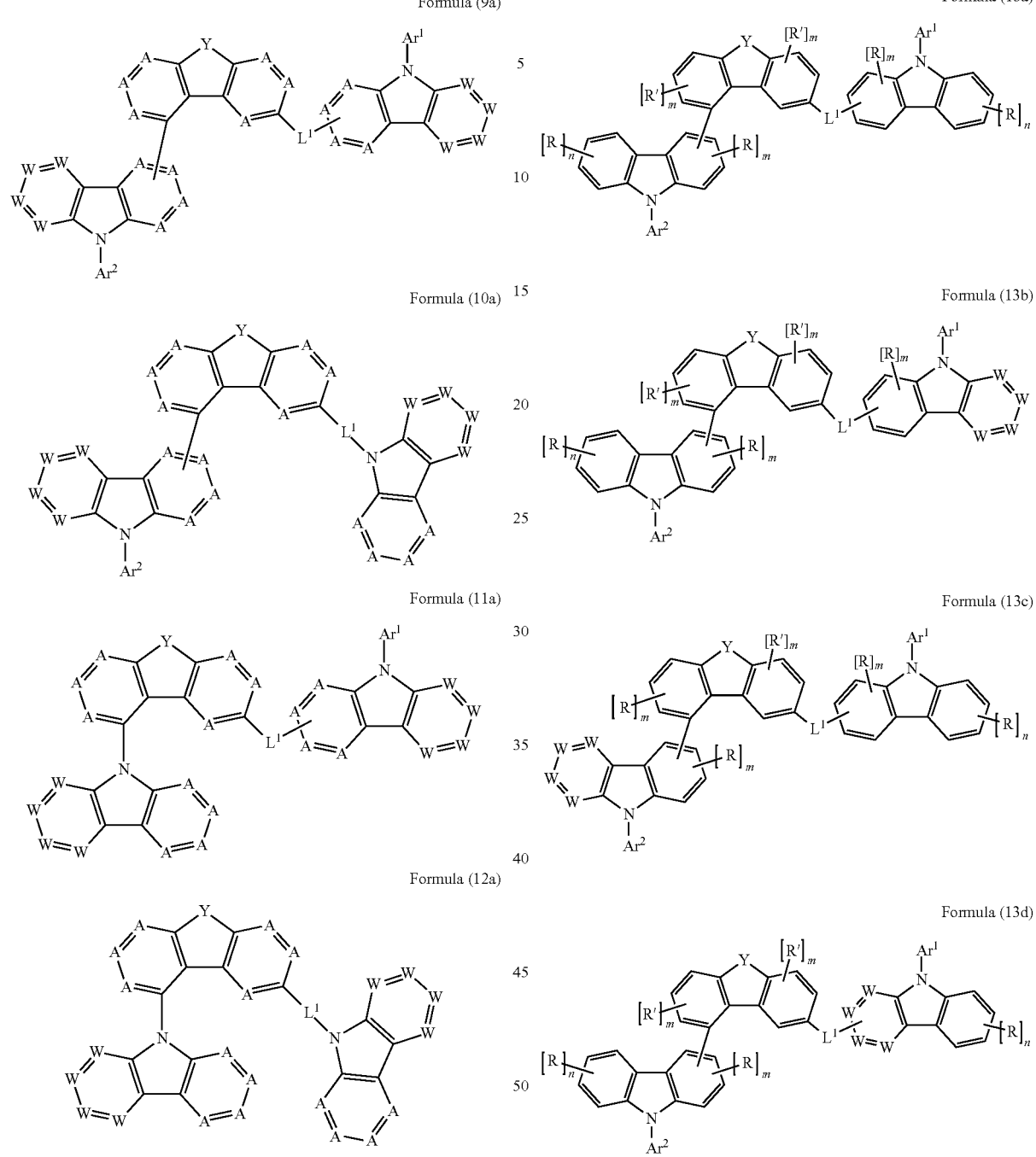

where the symbols used have the definitions given above.

Preference is given here to compounds of the formula (1), (2) or (3), or (9), (10) or (11), or (9a), (10a) or (11a).

In a preferred embodiment of the invention, W is the same or different at each instance and is CR, or two W are a group of the formula (5) or (6) and the remaining W are CR, and A is the same or different at each instance and is CR'. Preference is thus given to the compounds of the following formulae (13a), (13b), (13c), (13d), (13e), (13f), (13g), (13h), (13i), (13j), (13k), (13l), (13m), (13n), (13O) and (13p):

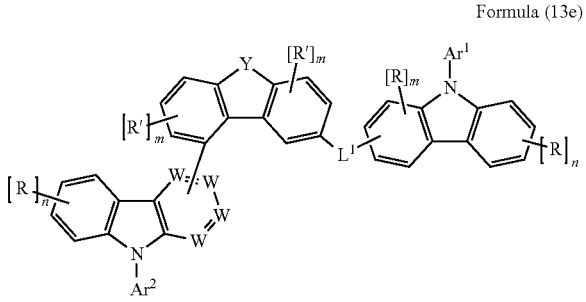

Formula (13f)
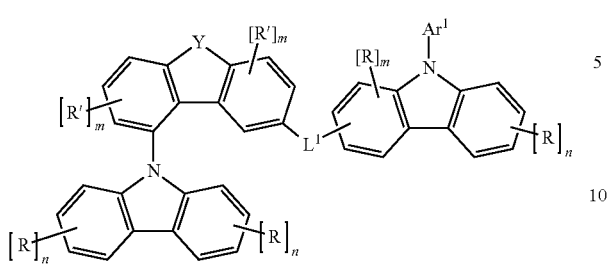
Formula (13g)
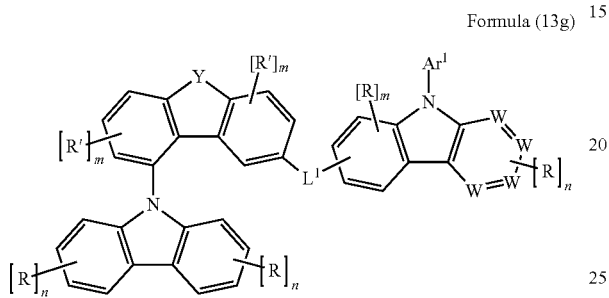
Formula (13h)
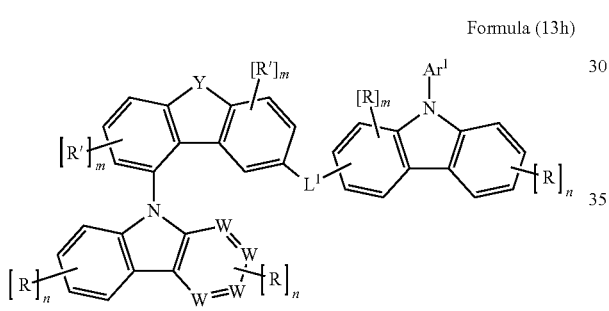
Formula (13i)
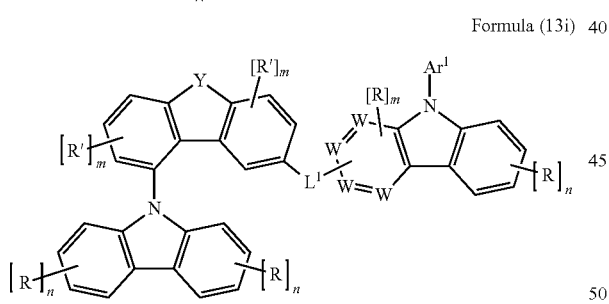
Formula (13j)
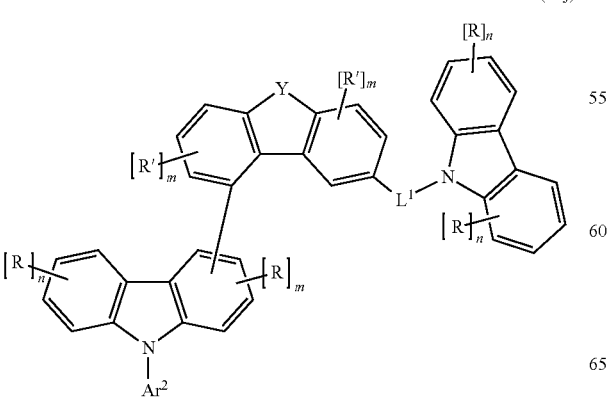
Formula (13k)
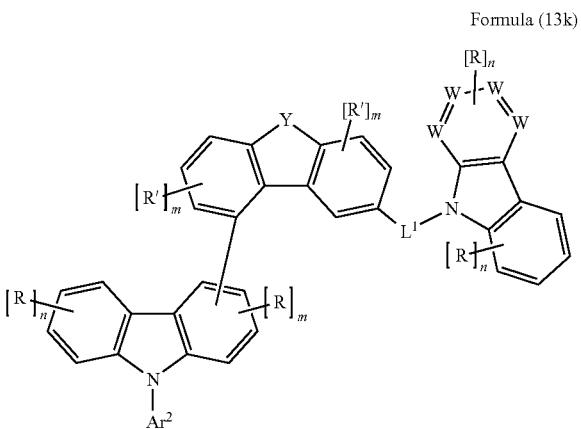
Formula (13l)
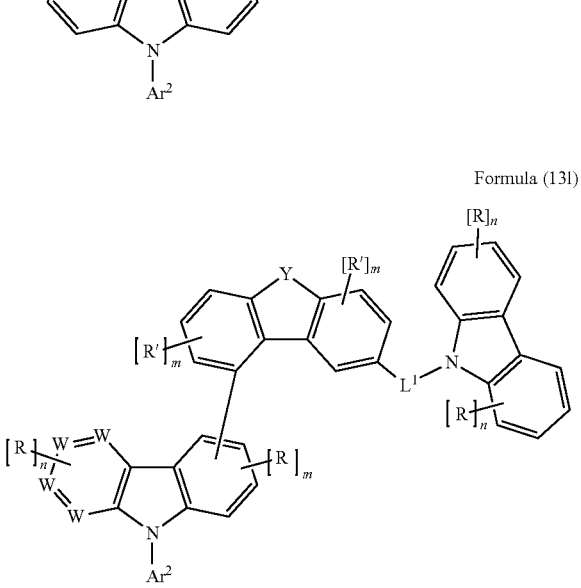
Formula (13m)
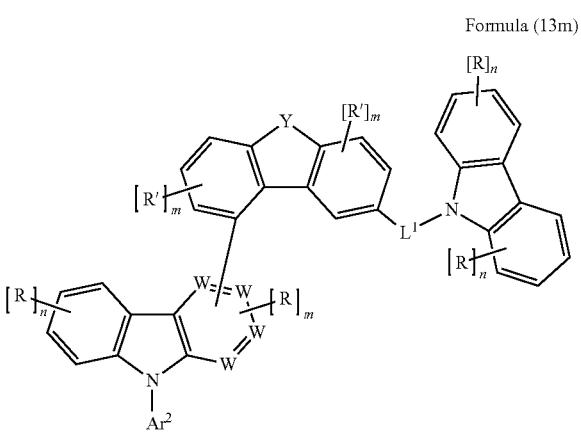
Formula (13n)
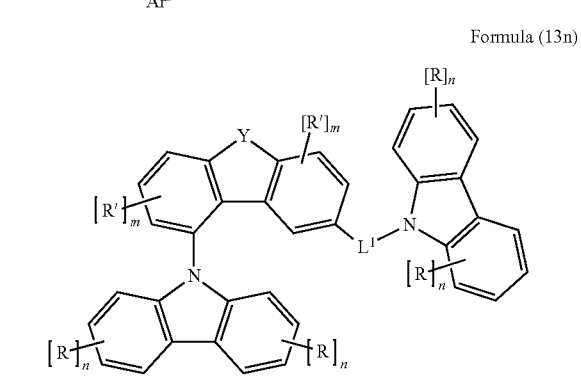

Formula (13o)

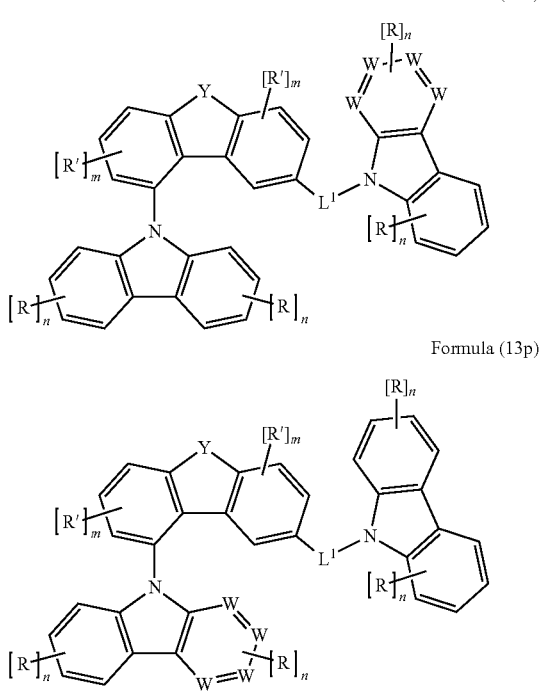

Formula (13p)

Formula (14a)

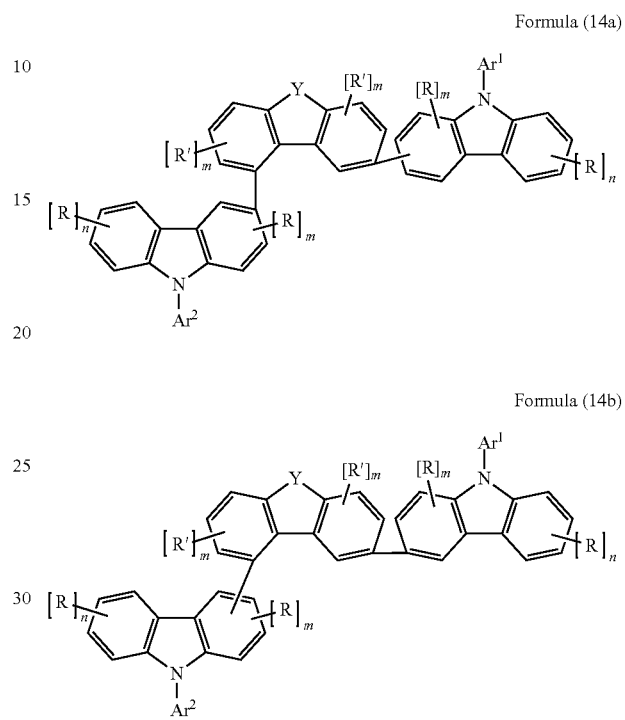

Formula (14b)

Formula (14c)

Formula (14d)

where:
W two adjacent W groups together are a group of the following formula (5a) or (6a) and the two other W groups are CR and preferably CH, where W is C when an $L^1$ group is bonded to this position, or the dibenzofuran or dibenzothiophene derivative is bonded to this position:

Formula (5a)

Formula (6a)

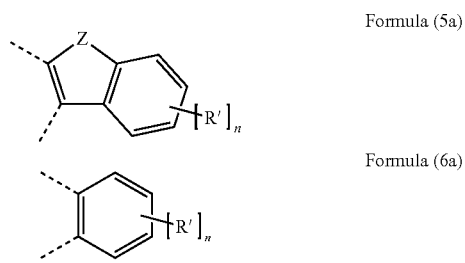

where the dotted bonds indicate the linkage of this group;
n is the same or different at each instance and is 0, 1, 2, 3 or 4;
m is the same or different at each instance and is 0, 1, 2 or 3;
where, in the formulae (13a), (13f, (13j), (13n), one R group is a group of one of the formulae (7) or (8) shown above, where, in addition:
Q is $CR^1$, where Q is C when the single bond to formula (13a), (13o, (13j) or (13n) is at this position, or two adjacent Q groups together are a group of the formula (5a) or (6a), where the group of the formula (7) or formula (8) has not more than two groups of the formula (5a) or formula (6a);
* is the single bond to formula (13a), (13f), (13j) or (13n);
the further symbols used have the definitions given above.
In a further preferred embodiment of the invention, $L^1$ and $L^2$ are each a single bond.

In a particularly preferred embodiment of the invention, at least one of the two carbazole groups or carbazole derivatives is joined by the 3 position, i.e. via the position para to the nitrogen atoms. Particular preference is thus given to the compounds of the following formulae (14a) to (14r):

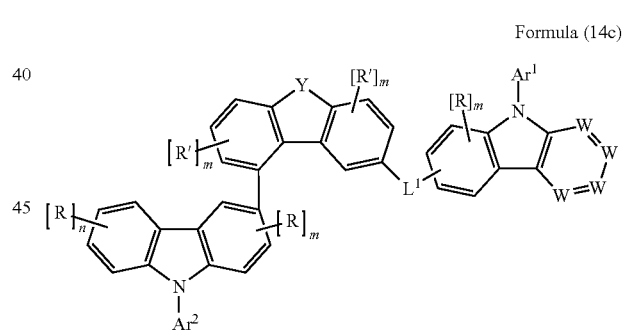

Formula (14e)
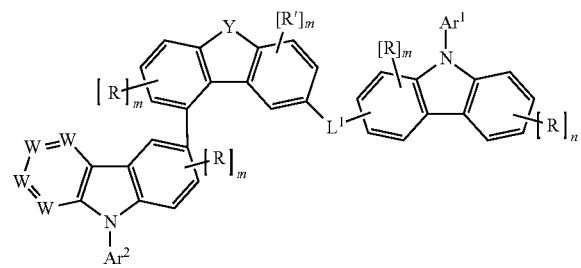
Formula (14f)
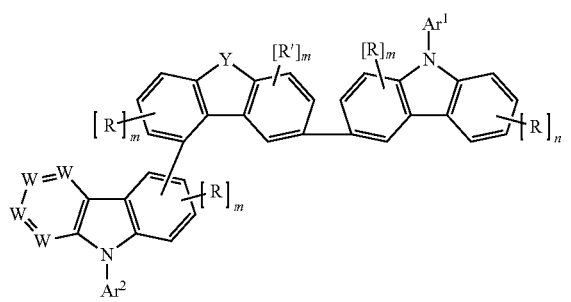
Formula (14g)
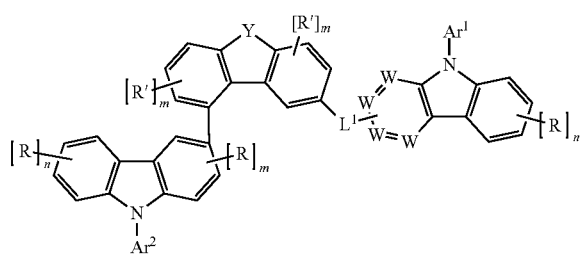
Formula (14h)
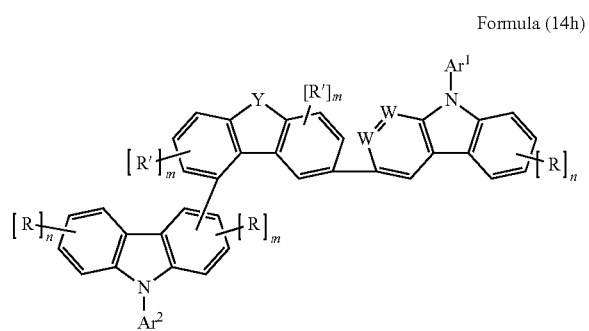
Formula (14i)
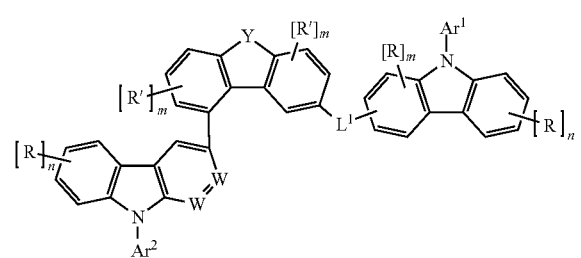
Formula (14j)
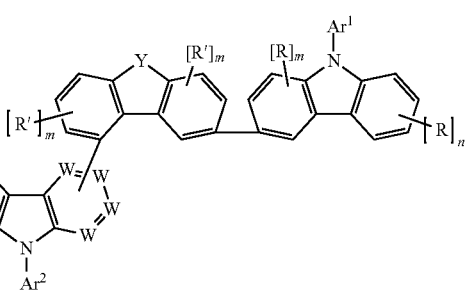
Formula (14k)
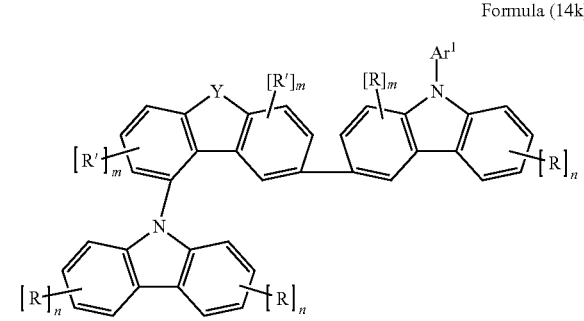
Formula (14l)
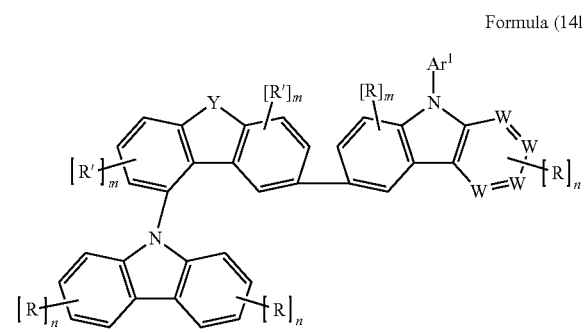
Formula (14m)
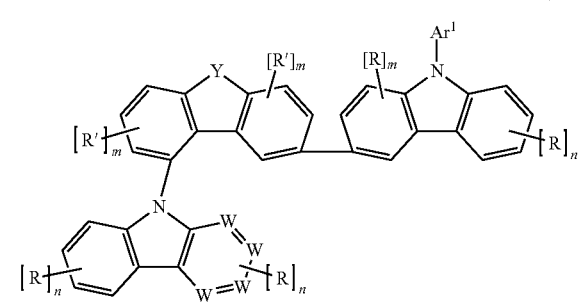
Formula (14n)
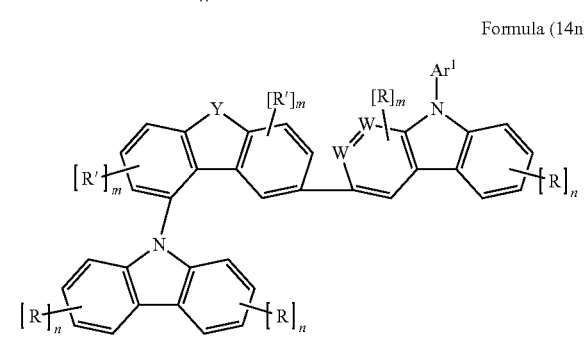

-continued

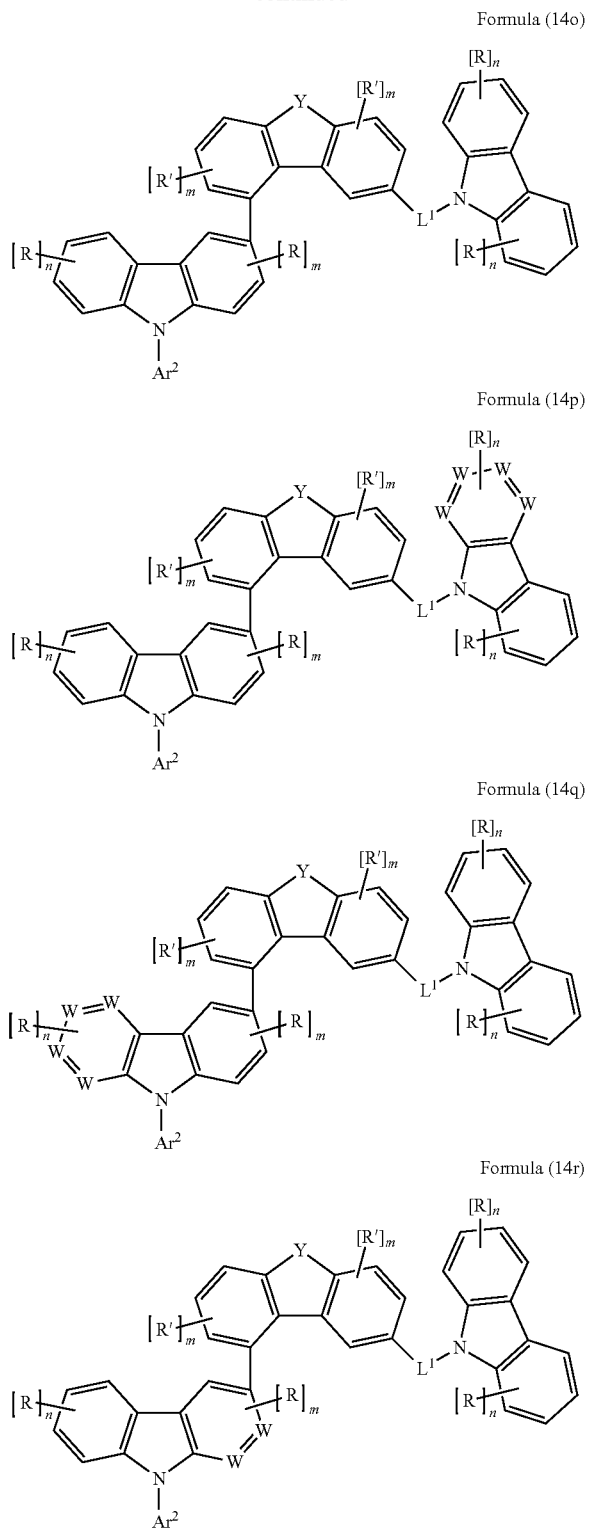

Formula (14o)

Formula (14p)

Formula (14q)

Formula (14r)

where the symbols and indices used have the definitions given above.

In a particularly preferred embodiment of the invention, both carbazole groups or carbazole derivatives are bonded via the 3 position, i.e. via the position para to the nitrogen atoms.

More preferably, the groups of the formula (7) or (8) or the preferred embodiments thereof, if present, are bonded in the para position to the nitrogen of the carbazole group to which the group is bonded.

More preferably, in a group of the formula (7), the single bond to the formula (1), (2), (3) or (4) is arranged in the para position to the nitrogen of the formula (7).

Particular preference is given to compounds of the formulae (1), (2), (3) or the preferred embodiments thereof, very particular preference to compounds of the formula (1) or the preferred embodiments thereof.

Very particular preference is given to compounds in which at least 2 adjacent W groups together are a group of the formula (5) or (6), preferably a group of the formula (5a) or (6a). Especially preferred are compounds in which at least 2 adjacent W groups together are a group of the formula (5), preferably a group of the formula (5a).

Preference is further given to compounds of the above-mentioned formulae in which Y is O.

In a further preferred embodiment of the invention, Z, if the compound contains a group of the formula (5), is O, NR where the R radical bonded to the nitrogen is not H, or $C(R)_2$, more preferably NR where the R radical bonded to the nitrogen is not H, or $C(R)_2$, and most preferably $C(R)_2$.

In a preferred embodiment of the invention, each of the carbazolyl derivative groups contains not more than one group of the formula (5) or formula (6).

When the compound of the invention contains a group of the formula (5), this may be bonded in various positions. This is shown hereinafter in schematic form with reference to preferred embodiments in which the A groups and the other W groups are CR, by the formulae (A) to (F):

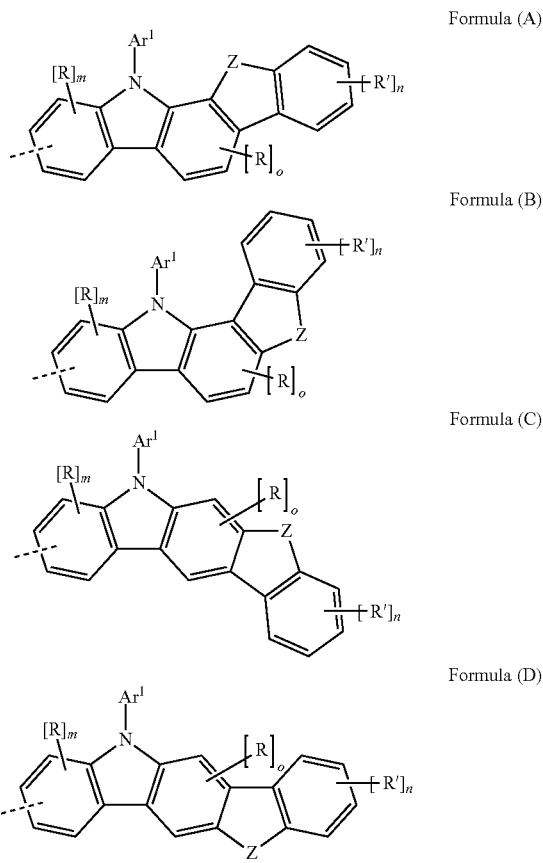

Formula (A)

Formula (B)

Formula (C)

Formula (D)

-continued

Formula (E)

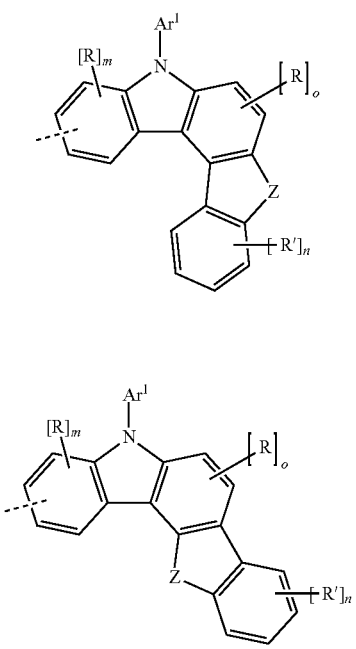

Formula (F)

Formula (I)

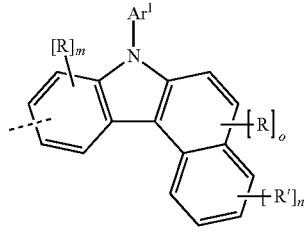

Formula (J)

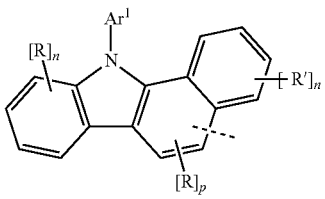

Formula (K)

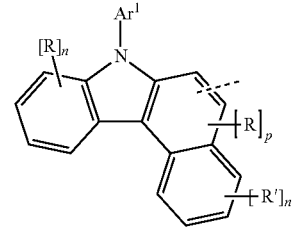

Formula (L)

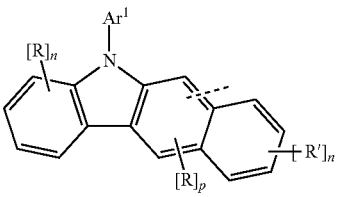

where the symbols and indices used have the definitions given above and the dotted bond represents the linkage in the compound of the invention where o is the same or different at each instance and is 0, 1 or 2. The same applies to the other carbazole derivatives which, rather than the $Ar^1$ group, contains an $Ar^2$ group bonded to the nitrogen. It is likewise possible for the bond to the compound of the invention to go via the nitrogen or via the middle of the three benzene groups rather than the dotted bond, in which case m is 0, 1, 2, 3 or 4 and, in the case of linkage via the middle benzene group, o is additionally 0 or 1.

Particular preference is given to groups of the formulae (B) and (C), especially formula (B).

When the compound of the invention contains a group of the formula (6), this may be bonded in various positions. This is shown hereinafter in schematic form with reference to preferred embodiments in which the A groups and the other W groups are CR, by the formulae (G) to (L):

Formula (G)

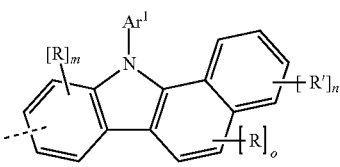

Formula (H)

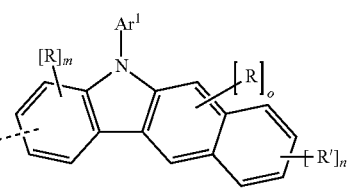

where the symbols and indices used have the definitions given above, p is 0 or 1, and the dotted bond represents the linkage in the compound of the invention. The same applies to the other carbazole derivative containing an $Ar^2$ group. It is likewise possible for the bond to the compound of the invention to go via the nitrogen instead of the dotted bond.

There follows a description of preferred embodiments of the $Ar^1$ and $Ar^2$ groups. As described above, the $Ar^1$ and $Ar^2$ groups are the same or different and are an aromatic ring system having 5 to 30 aromatic ring atoms or is a dibenzofuran or dibenzothiophene group, each of which may be substituted by one or more nonaromatic R radicals.

In a further preferred embodiment of the invention, the $Ar^1$ or $Ar^2$ group is an aromatic ring system having 6 to 24 aromatic ring atoms, preferably having 6 to 18 aromatic ring atoms, more preferably having 6 to 12 aromatic ring atoms, or is a dibenzofuran or dibenzothiophene group, where these groups may each be substituted by one or more nonaromatic R radicals, but are preferably unsubstituted. Examples of suitable and preferred $Ar^1$ or $Ar^2$ groups are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, 1-, 2-, 3- or 4-dibenzofuranyl and 1-, 2-, 3- or 4-dibenzothienyl, each of which may be substituted by one or more nonaromatic R radicals, but are preferably unsubstituted.

Examples of suitable Ar¹ or Ar² groups are the structures Ar¹-1 to Ar¹-19 or Ar²-1 to Ar²-19 listed below:
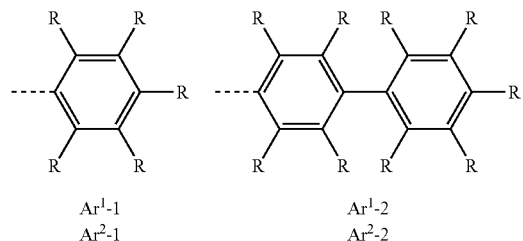
Ar¹-1
Ar²-1
Ar¹-2
Ar²-2
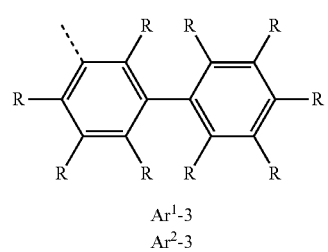
Ar¹-3
Ar²-3
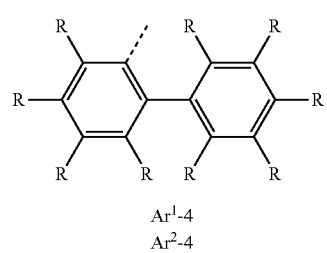
Ar¹-4
Ar²-4
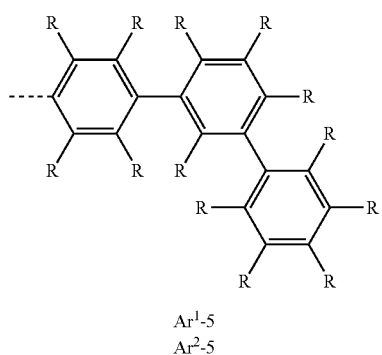
Ar¹-5
Ar²-5
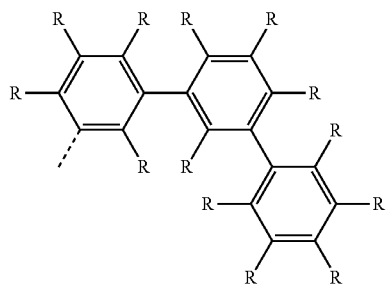
Ar¹-6
Ar²-6
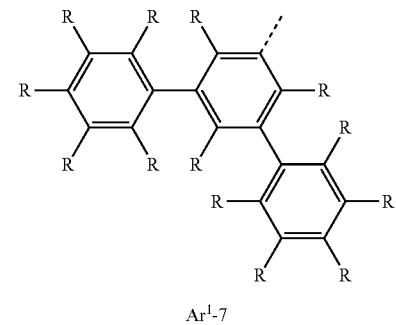
Ar¹-7
Ar²-7
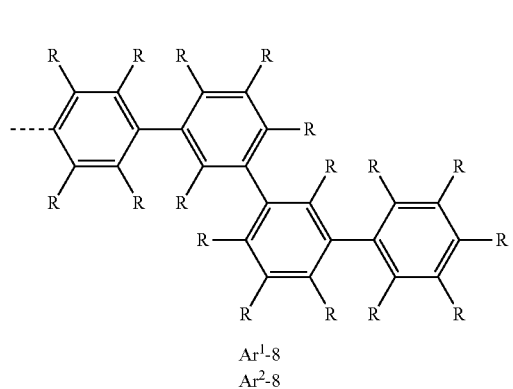
Ar¹-8
Ar²-8
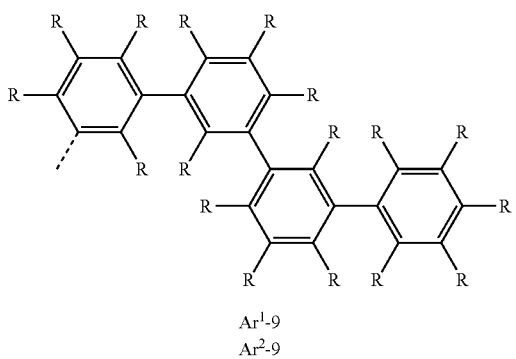
Ar¹-9
Ar²-9
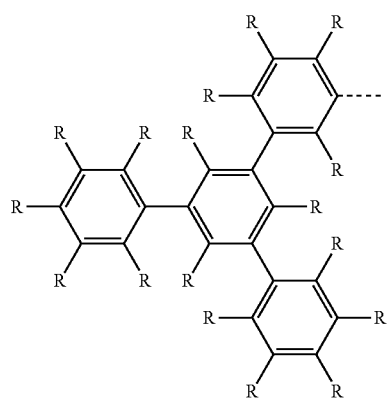
Ar¹-10
Ar²-10

-continued
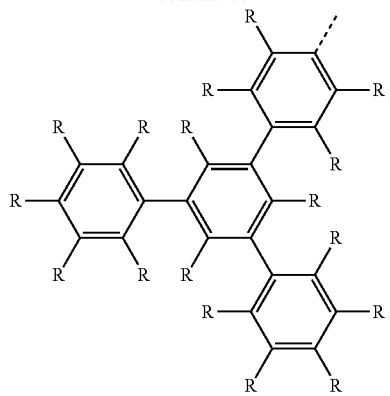
Ar¹-11
Ar²-11
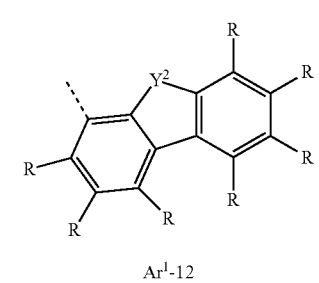
Ar¹-12
Ar²-12
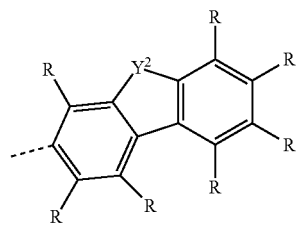
Ar¹-13
Ar²-13
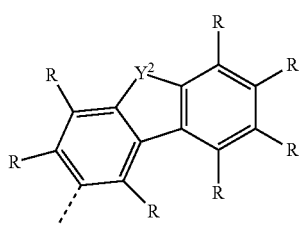
Ar¹-14
Ar²-14
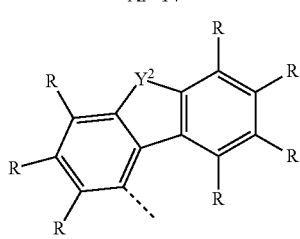
Ar¹-15
Ar²-15
-continued
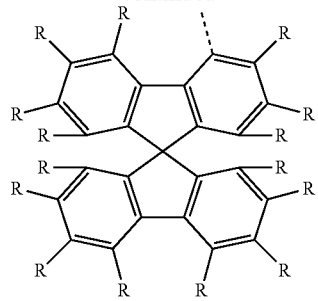
Ar¹-16
Ar²-16
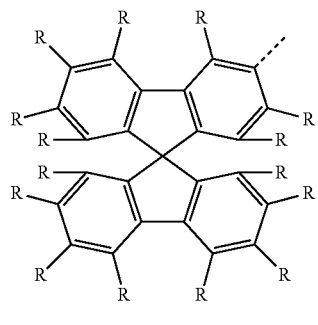
Ar¹-17
Ar²-17
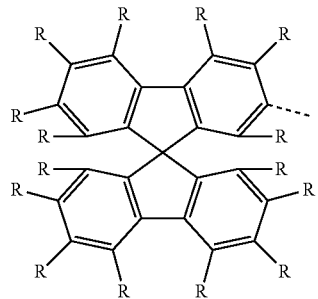
Ar¹-18
Ar²-18
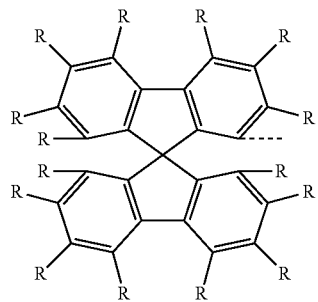
Ar¹-19
Ar²-19
where R has the definitions given above and is a nonaromatic group, the dotted bond represents the bond to the nitrogen atom and $Y^3$ is the same or different at each instance and is $CR_2$, O or S.

In a further preferred embodiment of the invention, in compounds of the formulae (13a) to (13p) and (14a) to (14r), the index n is the same or different at each instance and is 0, 1, 2 or 3, more preferably 0, 1 or 2 and even more preferably 0 or 1.

In yet a further preferred embodiment of the invention, in compounds of the formulae (13a) to (13p) and (14a) to (14r), the index m, if present, is the same or different at each instance and is 0, 1 or 2, more preferably 0 or 1 and even more preferably 0.

There follows a description of preferred substituents R or R'. R or R' is preferably selected from the group consisting of H, D, F, CN, $N(R^1)_2$, $C(=O)R^1$, $P(=O)(R^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, which may be substituted in each case by one or more $R^1$ radicals, where one or more nonadjacent $CH_2$ groups may be replaced by O and where one or more hydrogen atoms may be replaced by D or F, an aromatic or heteroaromatic ring system which has 5 to 24 aromatic ring atoms and may be substituted in each case by one or more $R^1$ radicals, but is preferably unsubstituted; at the same time, it is optionally possible for two R substituents bonded to the same carbon atom or to adjacent carbon atoms, or two R' substituent bonded to adjacent carbon atoms, to form a monocyclic or polycyclic, aliphatic, aromatic or heteroaromatic ring system which may be substituted by one or more $R^1$ radicals.

More preferably, these R or R' substituents are selected from the group consisting of H, D, F, CN, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which may be substituted in each case by one or more $R^1$ radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more nonaromatic $R^1$ radicals, but is preferably unsubstituted; at the same time, it is optionally possible for two R substituents bonded to the same carbon atom or to adjacent carbon atoms, or two R' substituents bonded to adjacent carbon atoms, to form a monocyclic or polycyclic aliphatic ring system which may be substituted by one or more $R^1$ radicals, but is preferably unsubstituted.

Most preferably, the R or R' substituents are selected from the group consisting of H and an aromatic or heteroaromatic ring system having 6 to 18 aromatic ring atoms, preferably having 6 to 13 aromatic ring atoms, each of which may be substituted by one or more nonaromatic $R^1$ radicals, but is preferably unsubstituted. Examples of suitable R or R' substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^1$ radicals, but are preferably unsubstituted. Suitable structures R are the same structures as depicted above for $Ar^1$-1 to $Ar^1$-19, in which case these R structures are substituted by $R^1$ rather than R.

When Z in the structure of the formula (5) is NR, it is preferable when the R radical bonded to this nitrogen atom is the same or different at each instance and is an aromatic or heteroaromatic ring system which has 5 to 24 aromatic ring atoms and may be substituted in each case by one or more $R^1$ radicals, more preferably an aromatic or heteroaromatic ring system which has 6 to 18 aromatic ring atoms and may be substituted by one or more $R^1$ radicals. Examples of suitable R substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by an $R^1$ radical other than H or D. These groups may each be substituted by one or more $R^1$ radicals, but are preferably unsubstituted. Suitable structures R are the same structures as depicted above for $Ar^1$-1 to $Ar^1$-19, in which case these R structures are substituted by $R^1$ rather than R.

When Z in the structure of the formula (5) is $CR_2$, it is preferable when the R radicals bonded to this carbon atom are the same or different at each instance and are an alkyl group which has 1 to 10 carbon atoms and may be substituted by one or more $R^1$ radicals, or an aromatic or heteroaromatic ring system which has 5 to 24 aromatic ring atoms and may be substituted in each case by one or more $R^1$ radicals, more preferably an alkyl group having 1, 2, 3 or 4 carbon atoms or an aromatic or heteroaromatic ring system which has 6 to 18 aromatic ring atoms and may be substituted by one or more $R^1$ radicals. It is also possible here for the two R radicals to form a ring system with one another.

In a further preferred embodiment of the invention, $R^1$ is the same or different at each instance and is selected from the group consisting of H, D, F, CN, an aliphatic hydrocarbyl radical having 1 to 6 carbon atoms, preferably having 1, 2, 3 or 4 carbon atoms, or an aromatic or heteroaromatic ring system having 5 to 30 aromatic ring atoms, preferably having 5 to 24 aromatic ring atoms, more preferably having 5 to 13 aromatic ring atoms, which may be substituted by one or more alkyl groups each having 1 to 4 carbon atoms, but is preferably unsubstituted.

It is further preferable that, when two adjacent A in one of the above formulae or the preferred embodiments are CR' or $CR^1$, these do not form a monocyclic or polycyclic, aliphatic, aromatic or heteroaromatic ring system. Preferably, the aromatic or heteroaromatic ring systems formed by the formulae (5) or (6), or the formulae (5a) or (6a), are the only aromatic or heteroaromatic ring systems formed by adjacent substituents.

It is further preferable when the aromatic or heteroaromatic R or R' or $R^1$ or $R^2$ or $Ar^1$ or $Ar^2$ groups in the compound of the invention do not have any aryl or heteroaryl groups having more than two aromatic six-membered rings fused directly to one another.

The abovementioned preferences can occur individually or together. It is preferable when the abovementioned preferences occur together.

Examples of suitable compounds of the invention are the structures shown below:
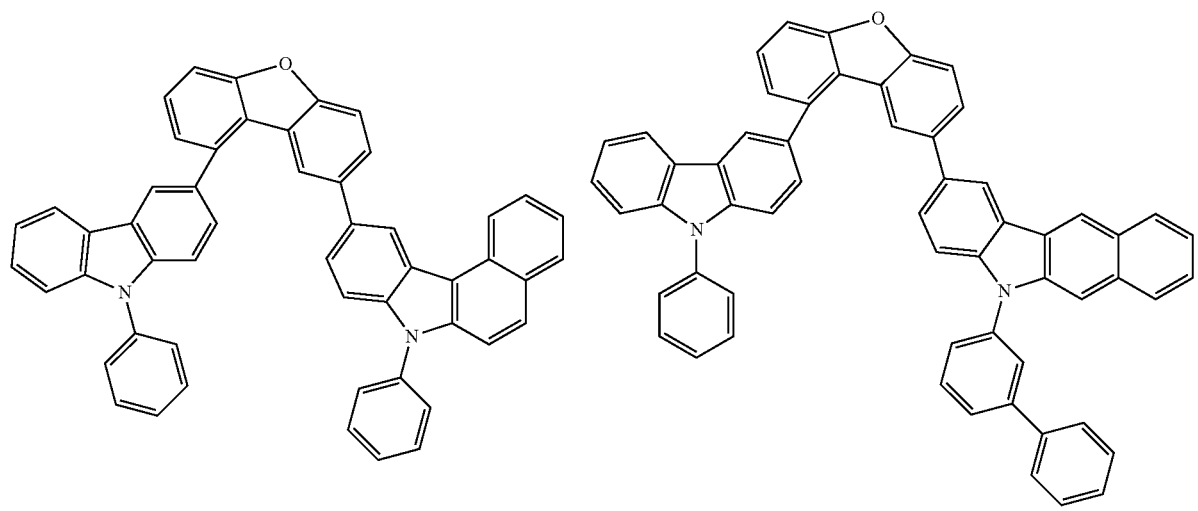
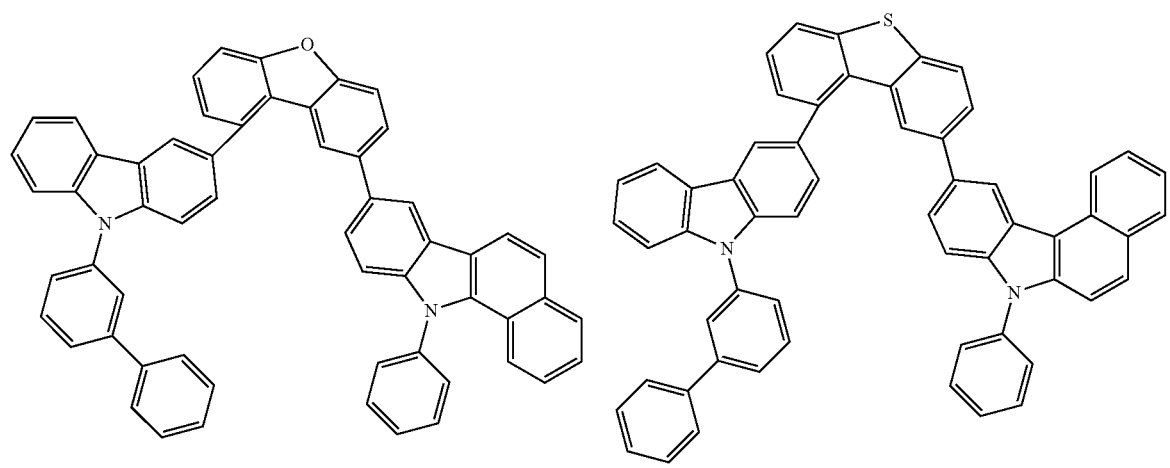
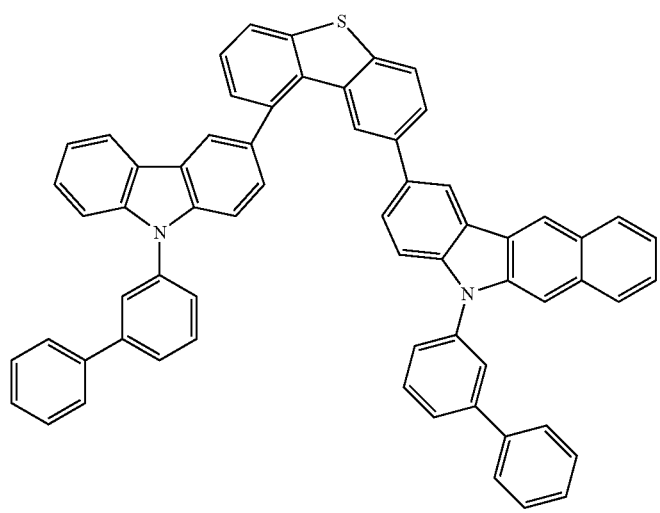

-continued
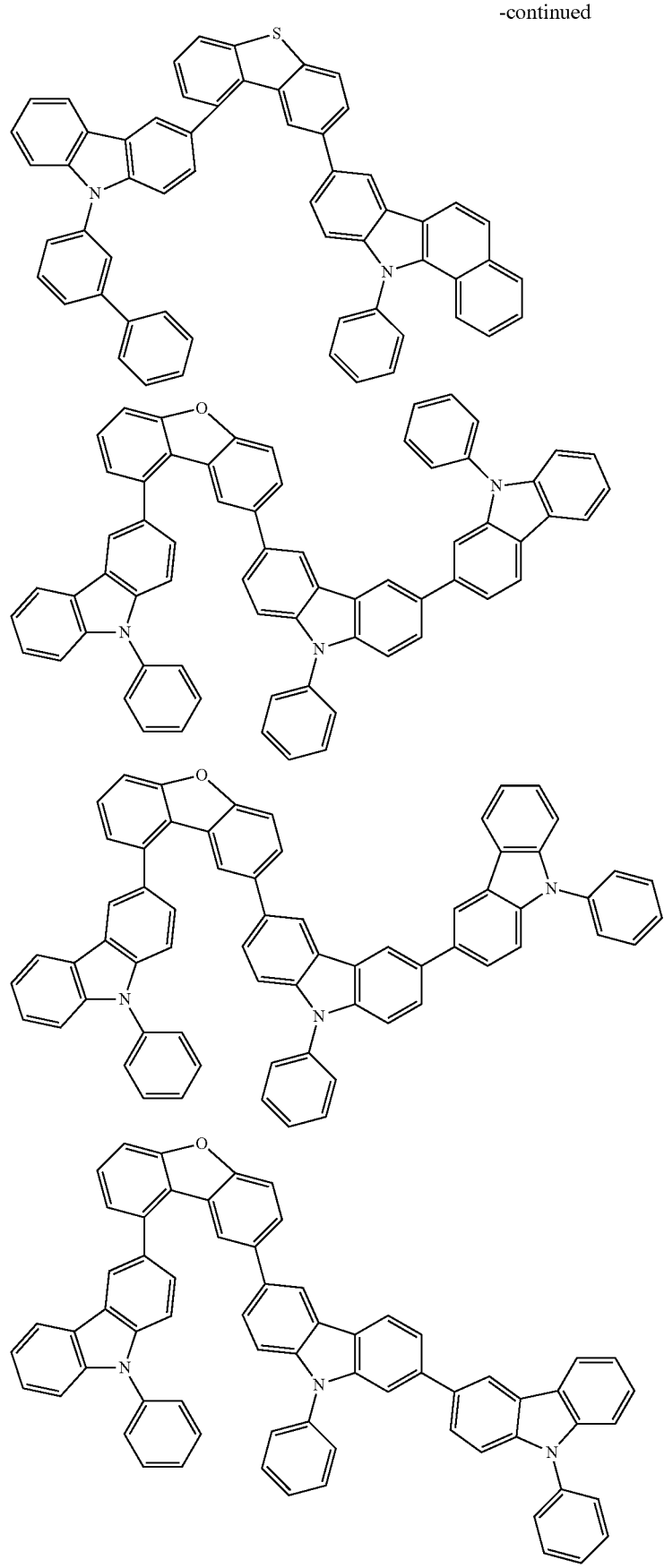

-continued
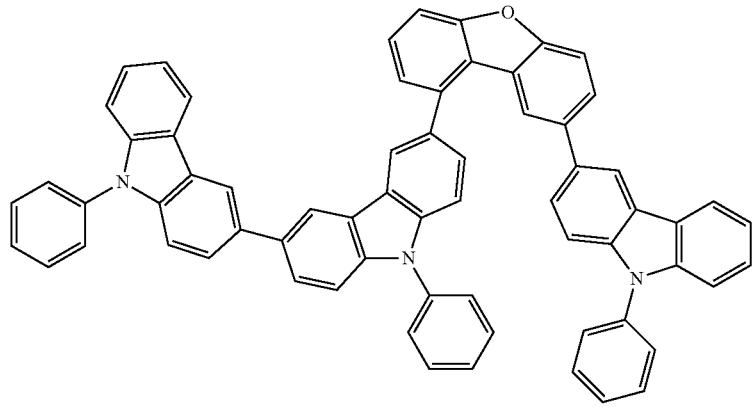
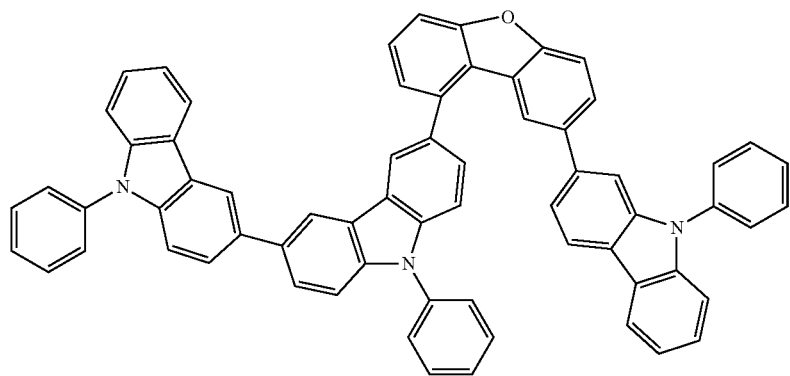
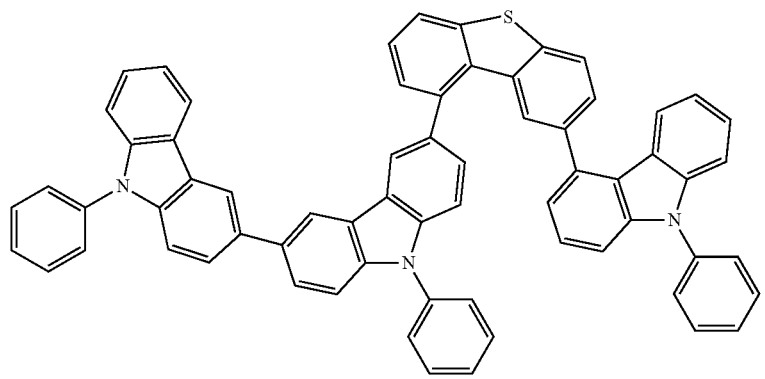
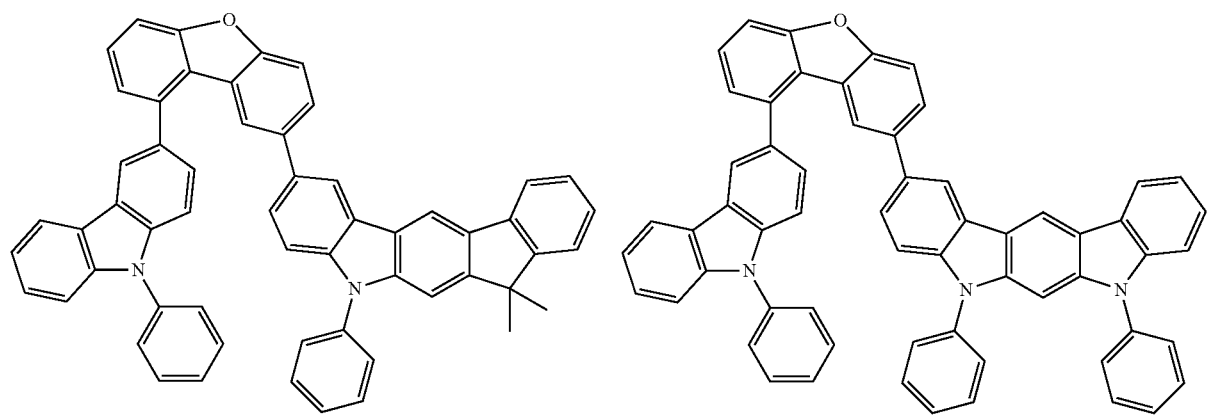

33 34
-continued
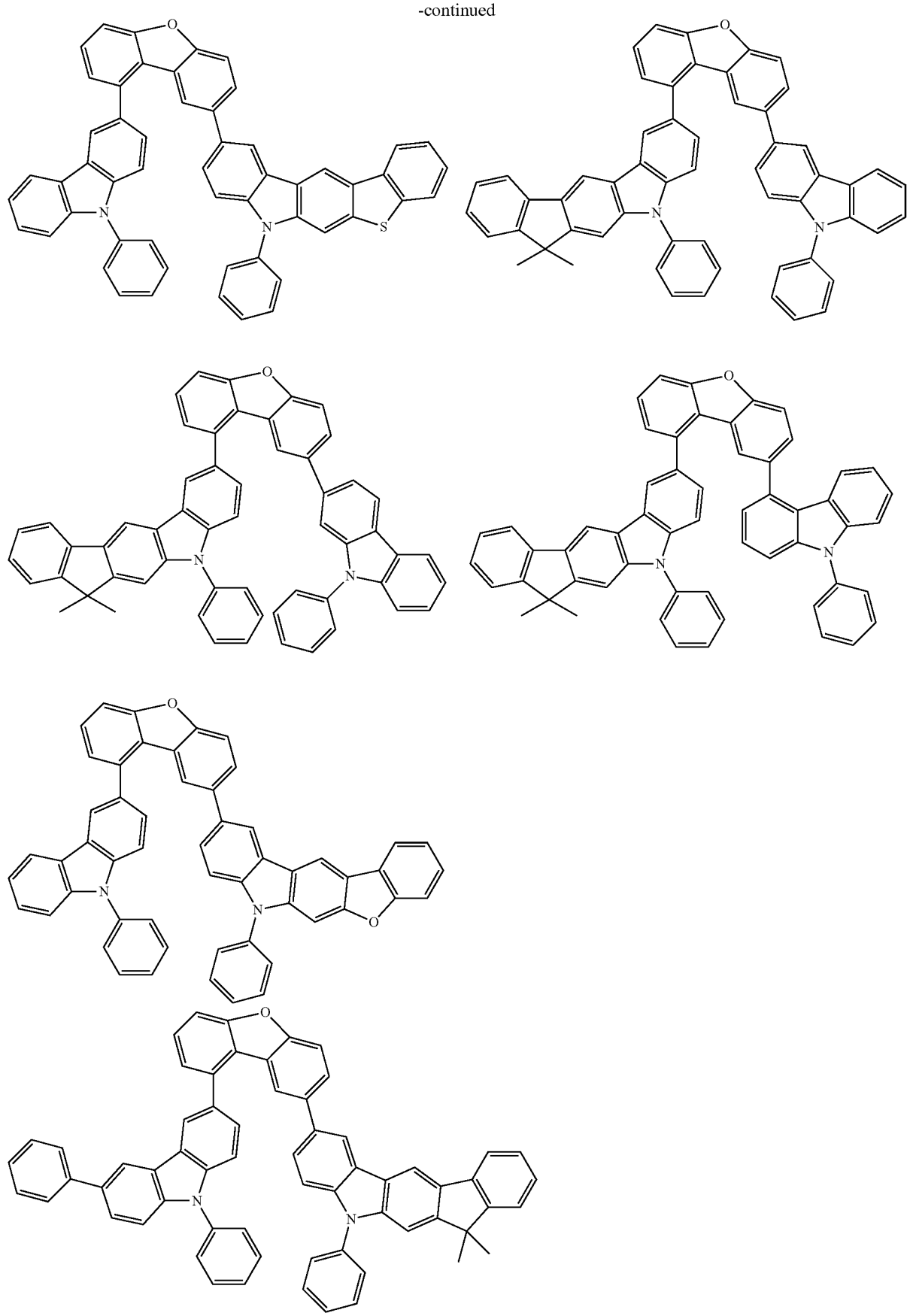

35
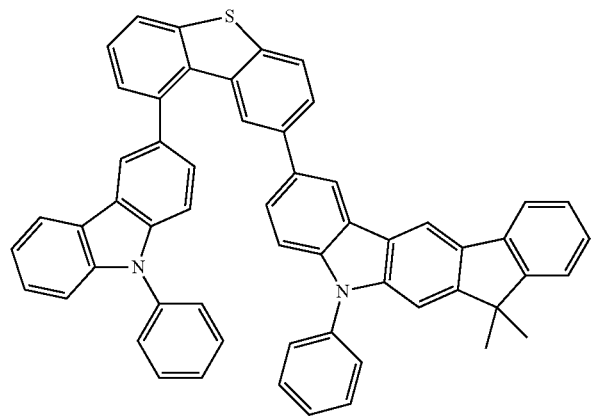
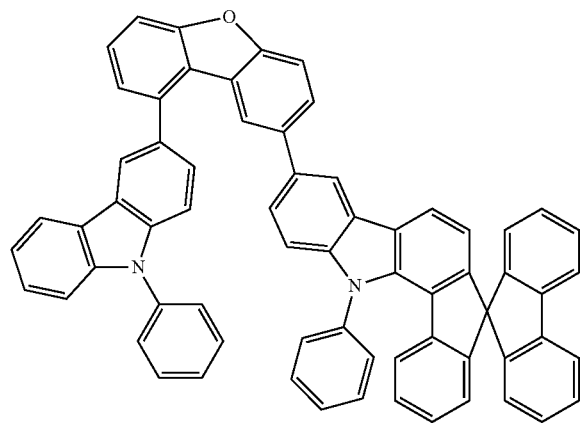
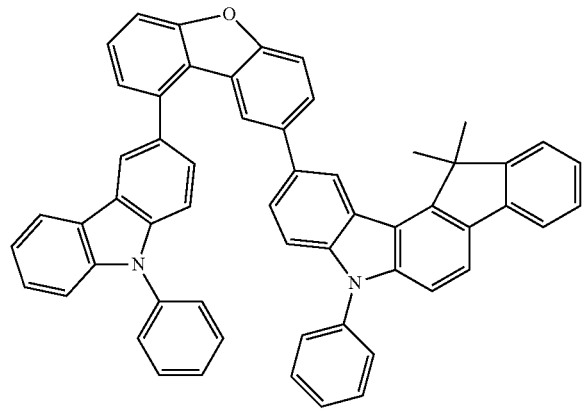
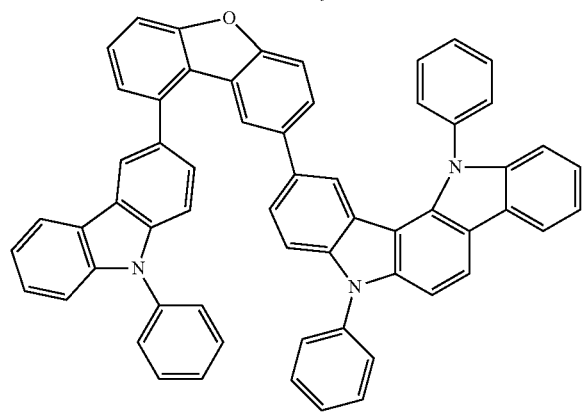
36
-continued
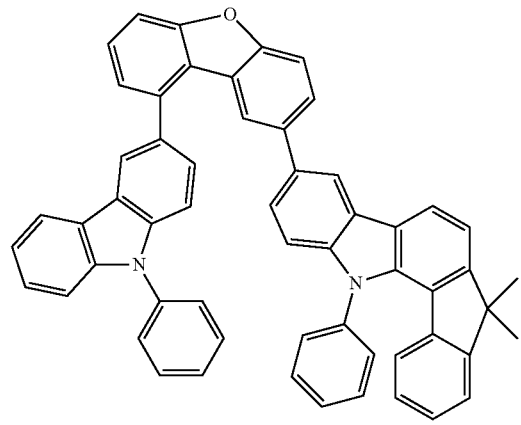
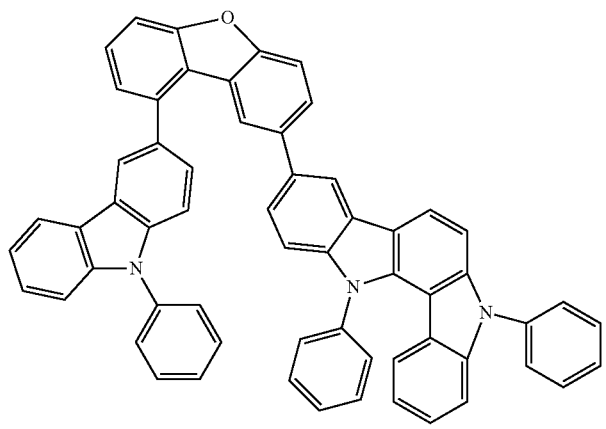
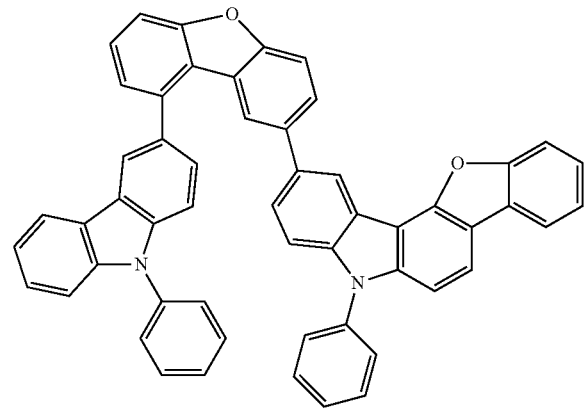
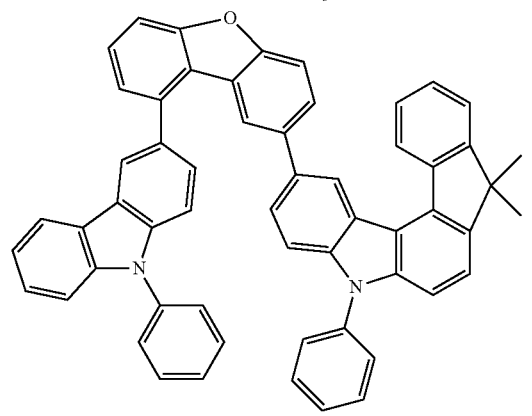

-continued
| 37 | 38 |
|---|---|
| 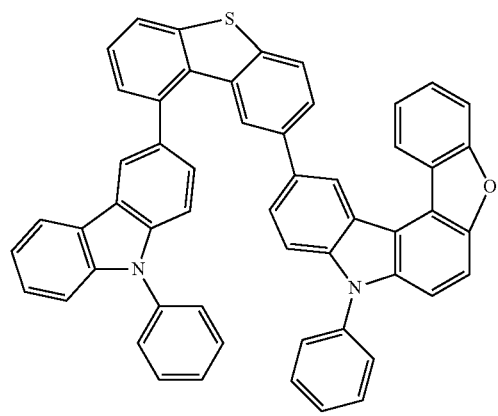 | 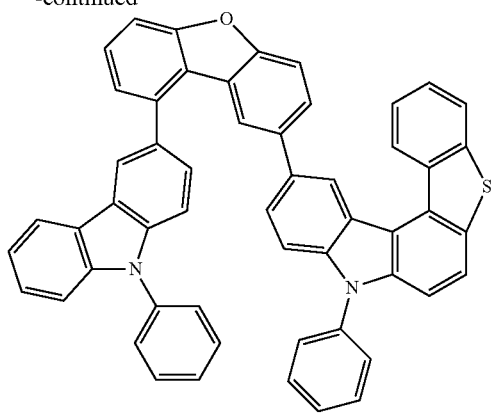 |
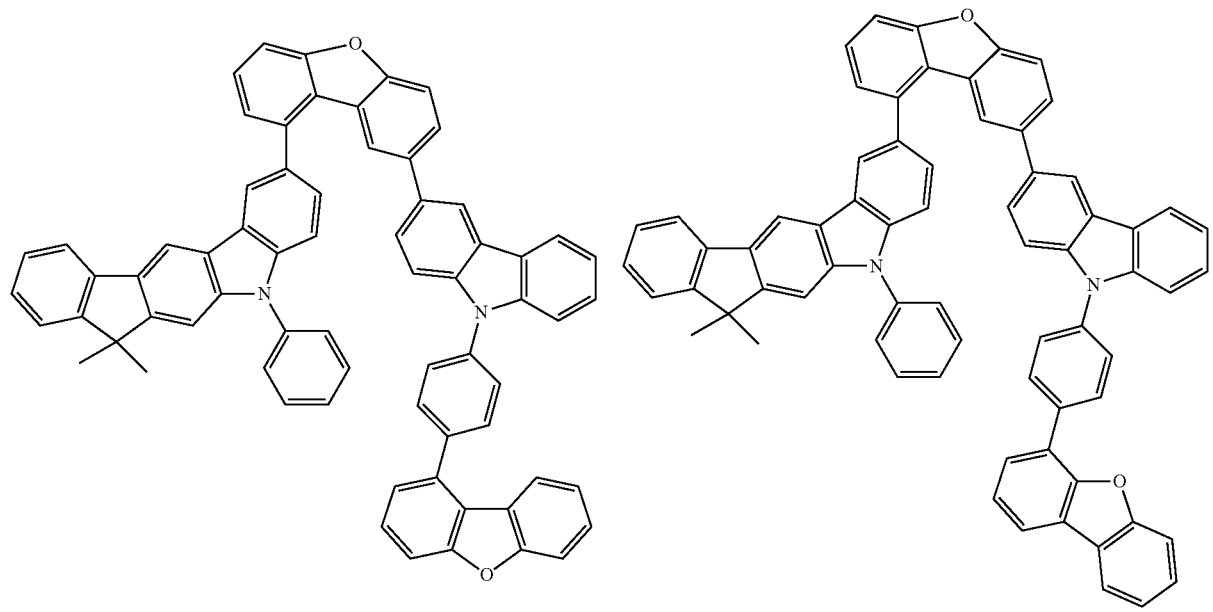
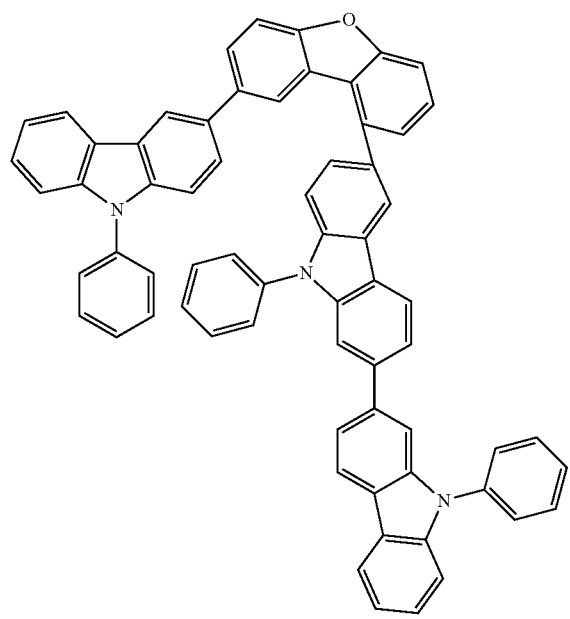

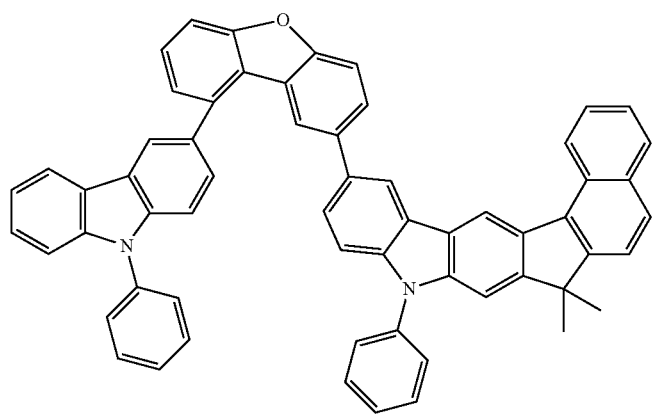
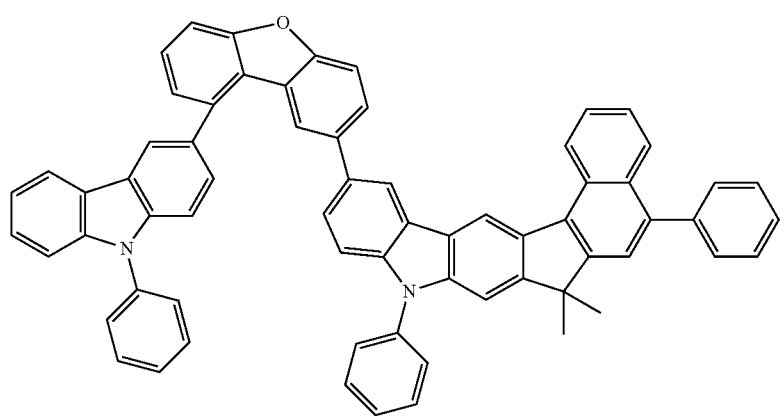
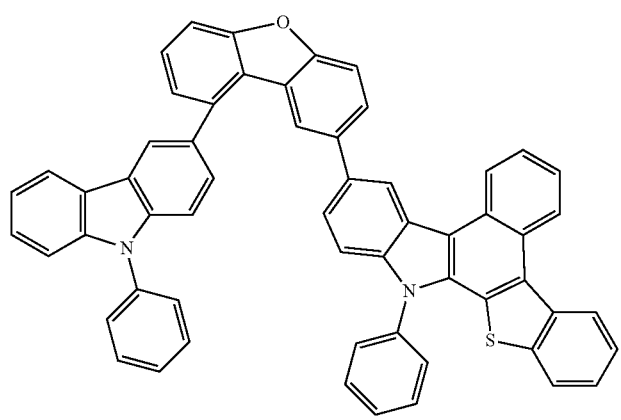
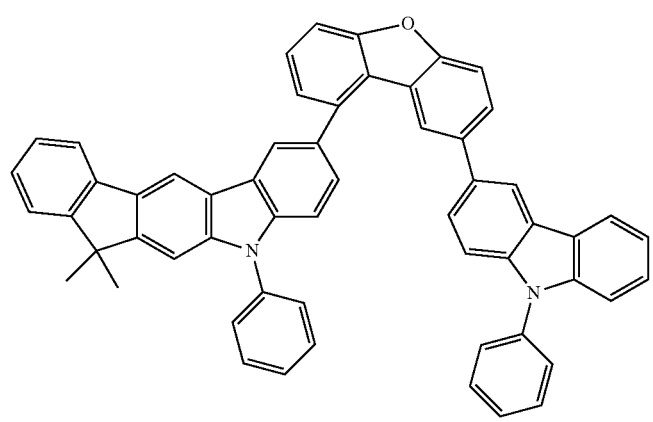

-continued
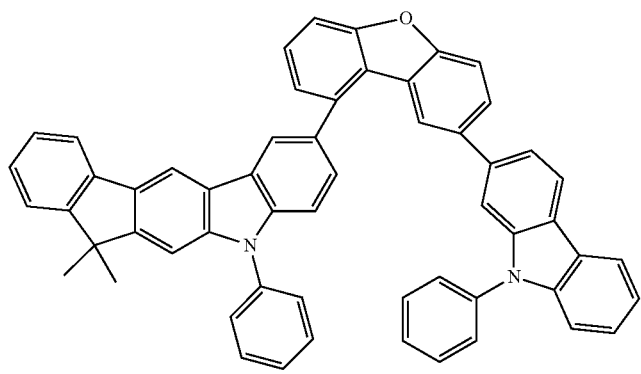
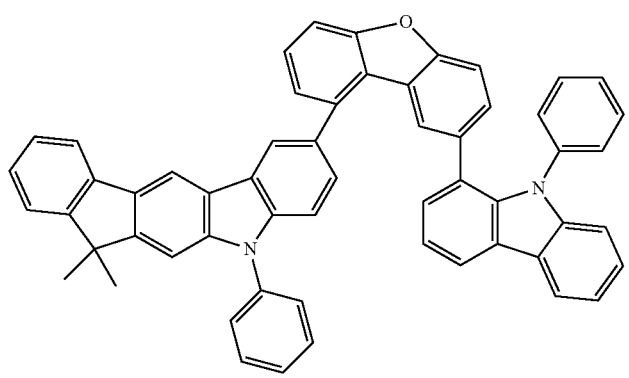
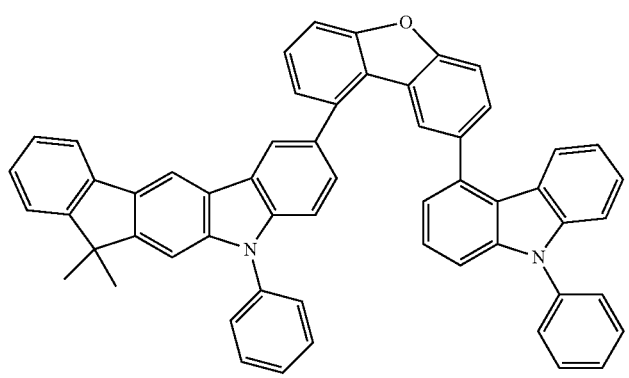
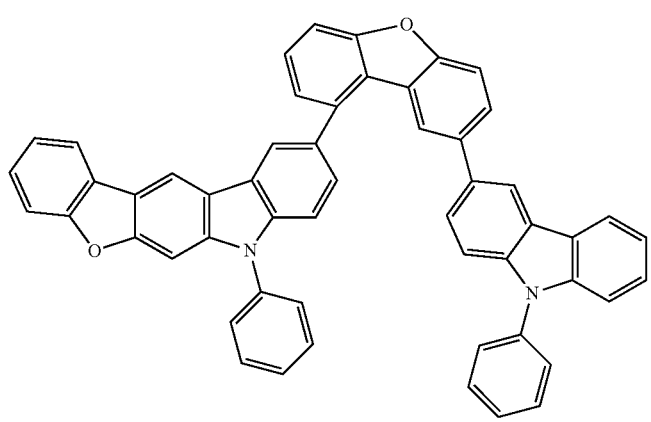

-continued
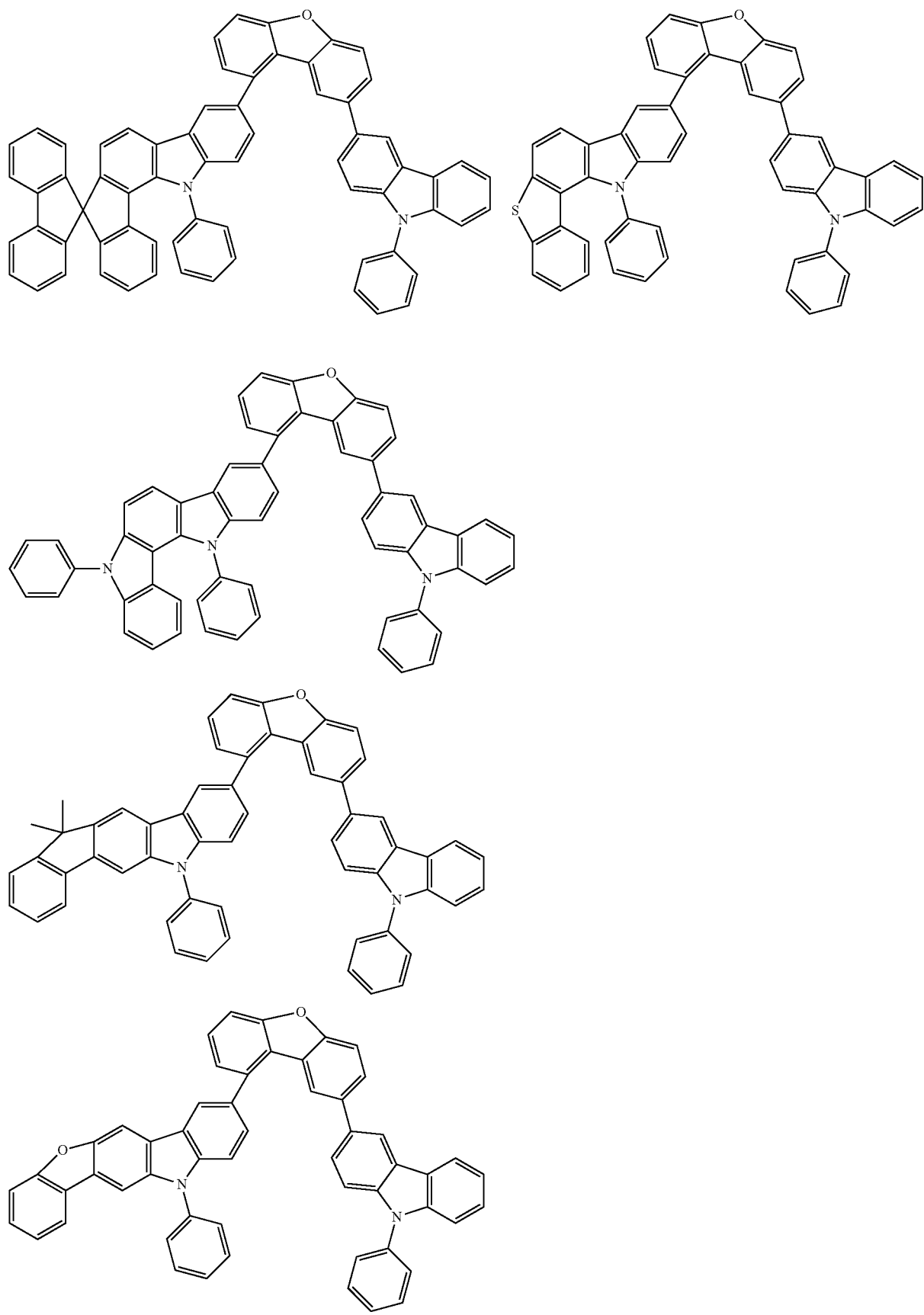

-continued
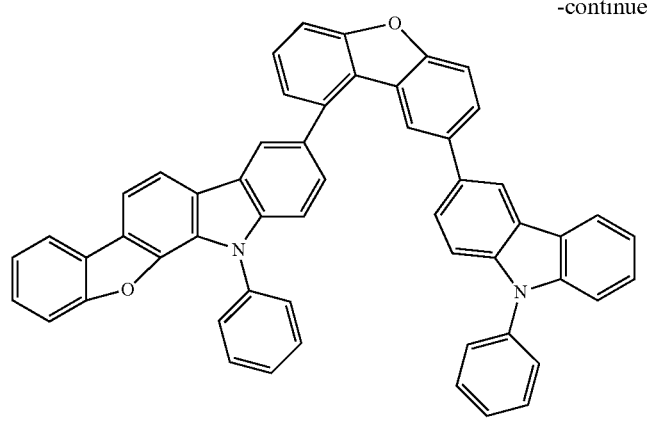
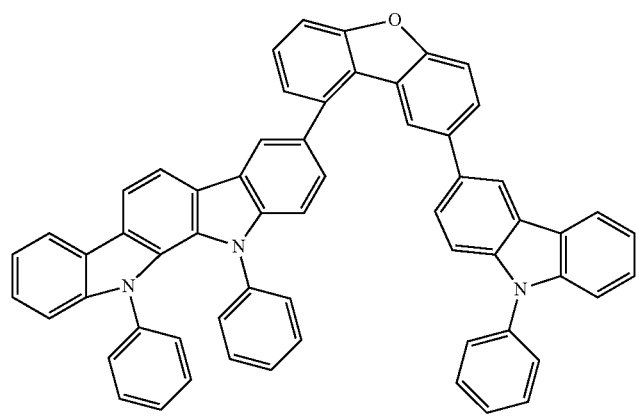
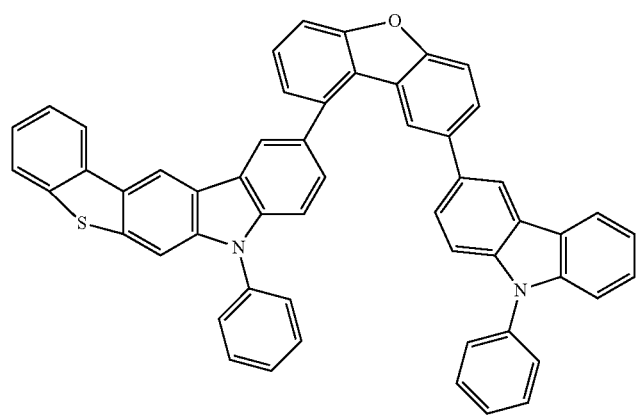
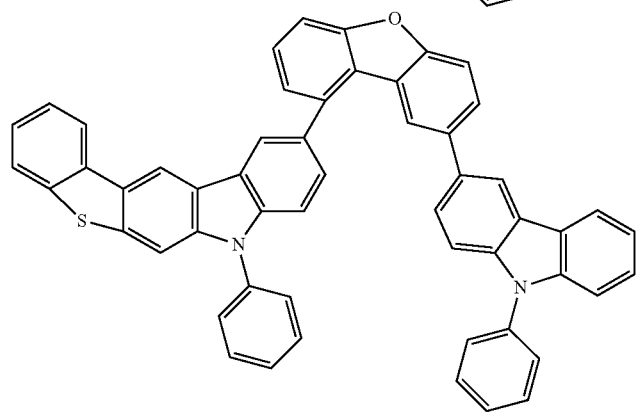

-continued
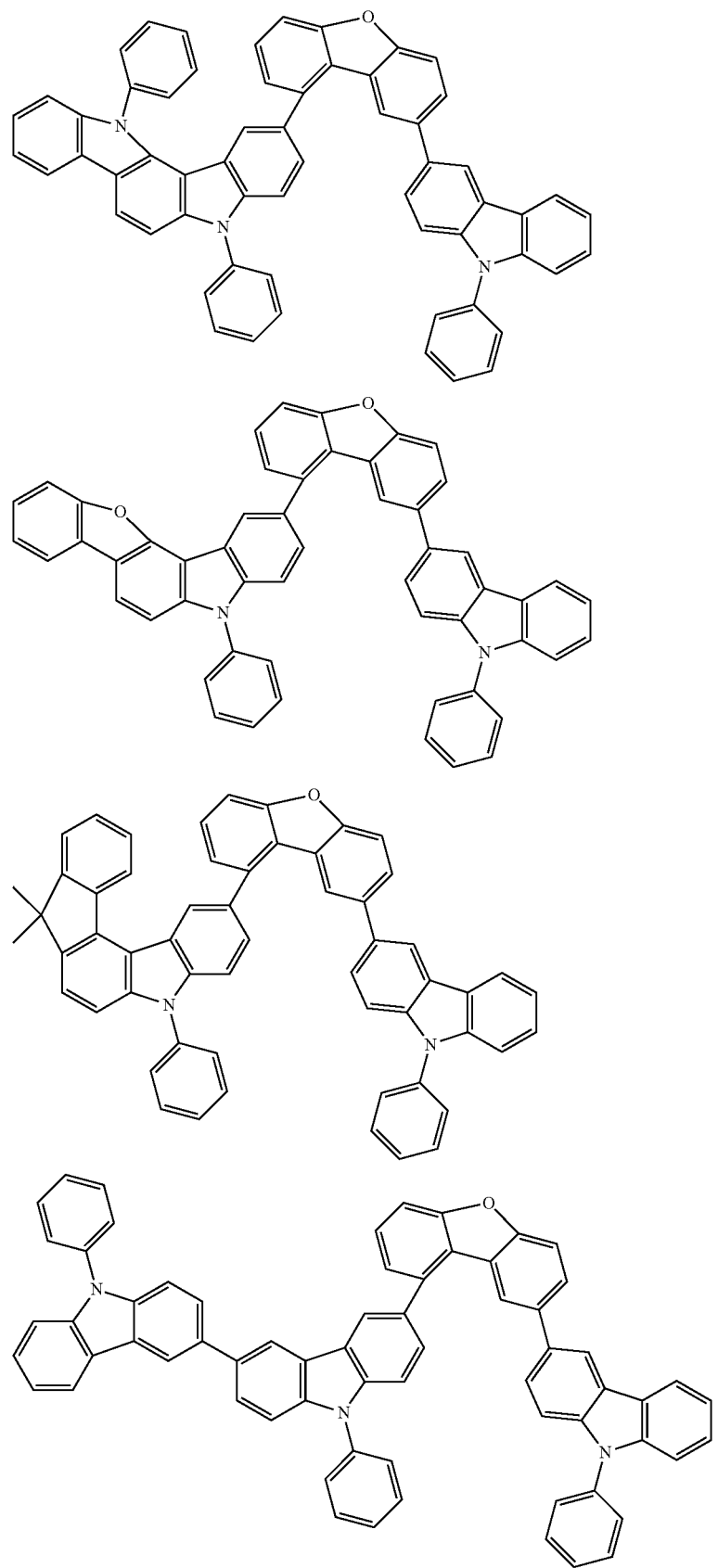

-continued
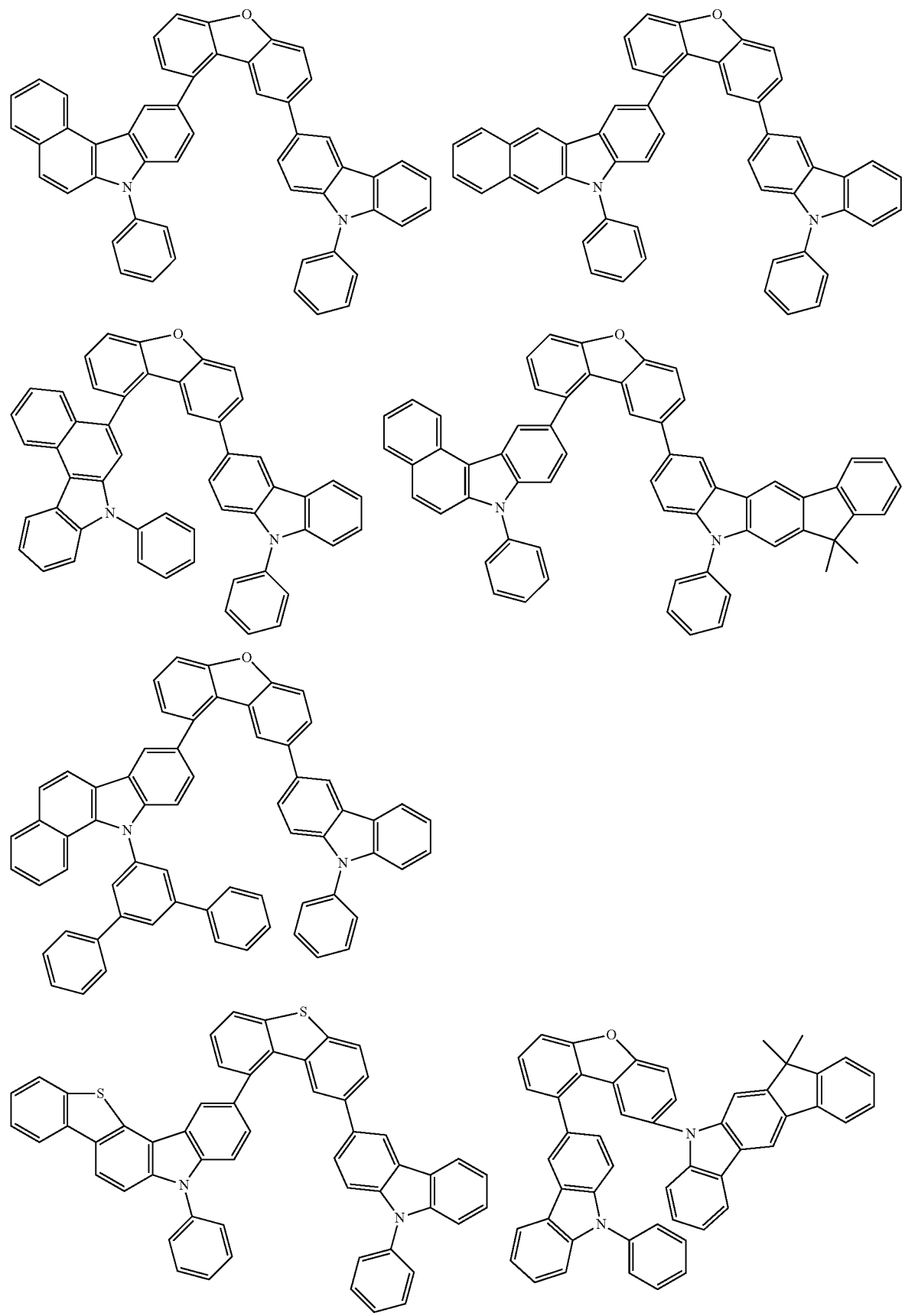

-continued
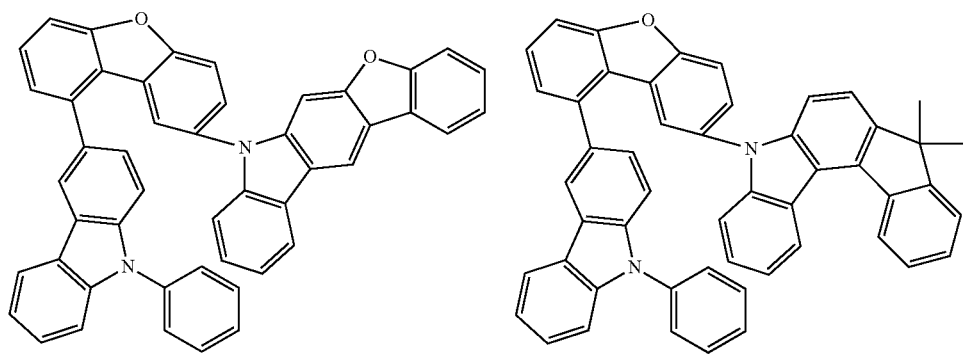
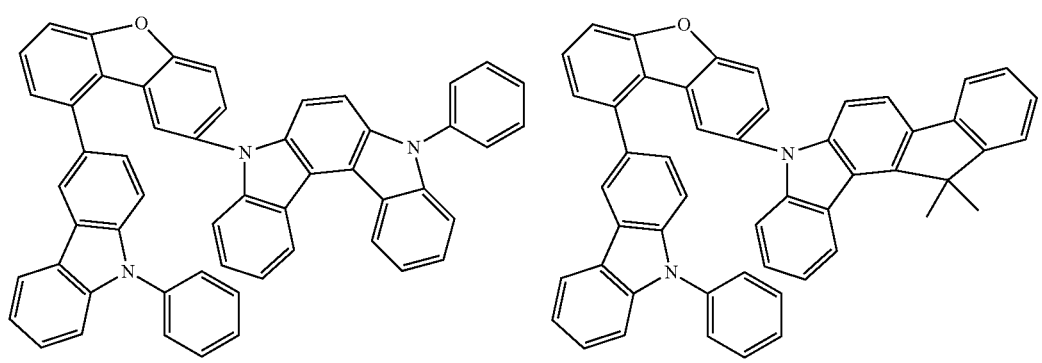
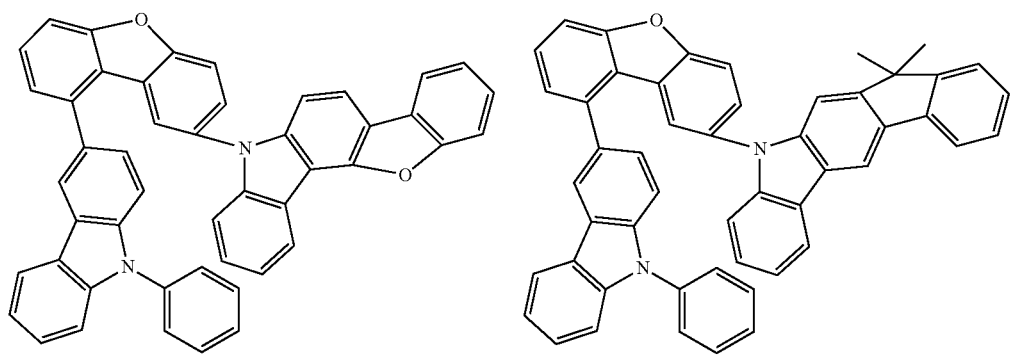
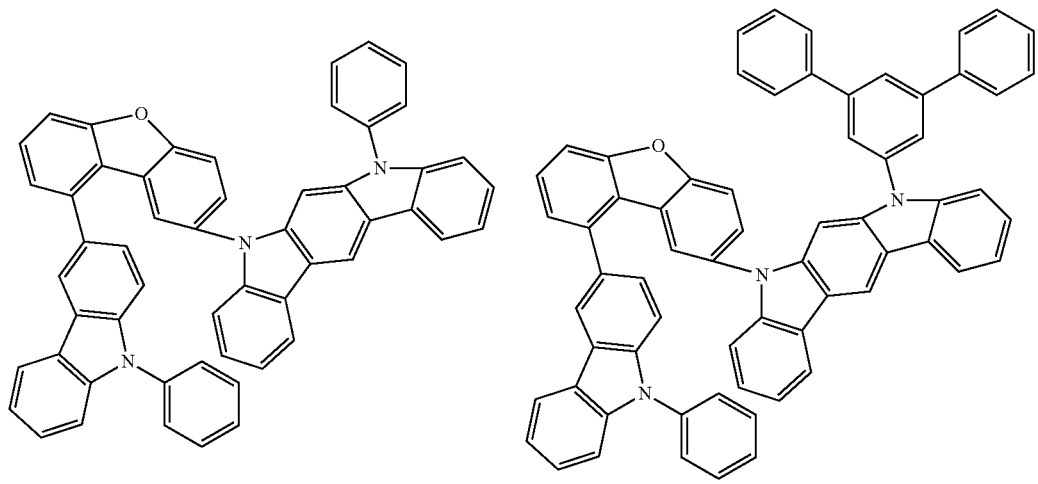

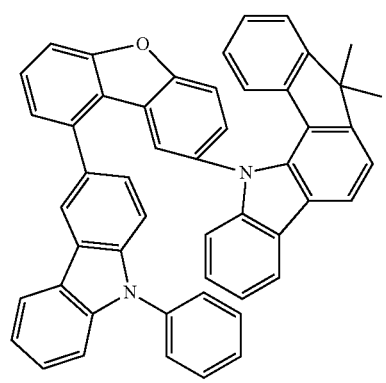
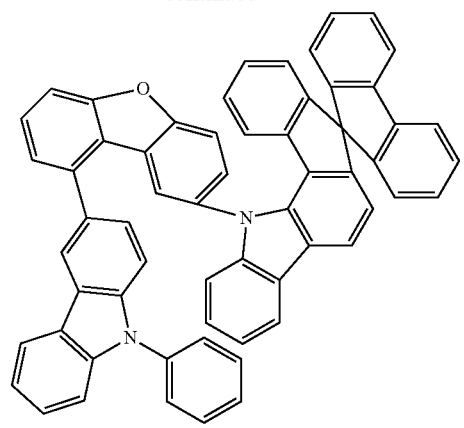
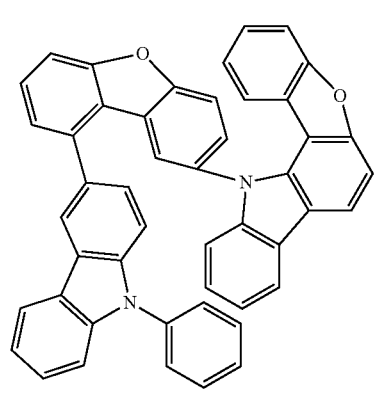
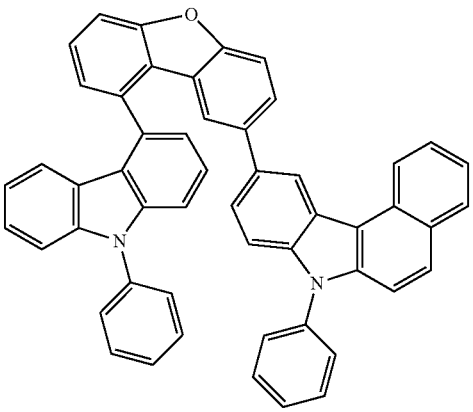
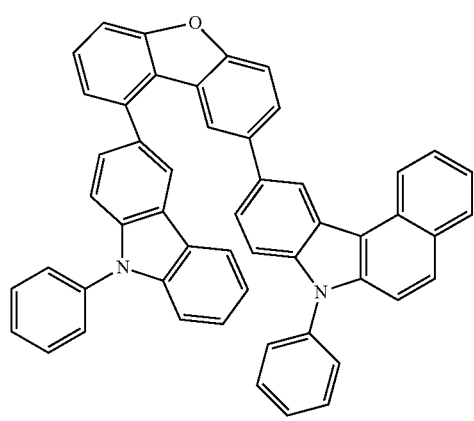
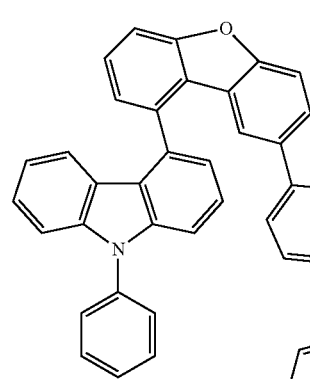
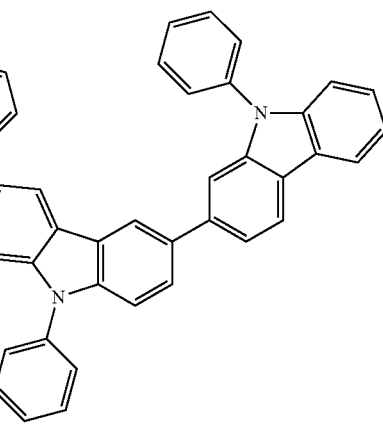

-continued
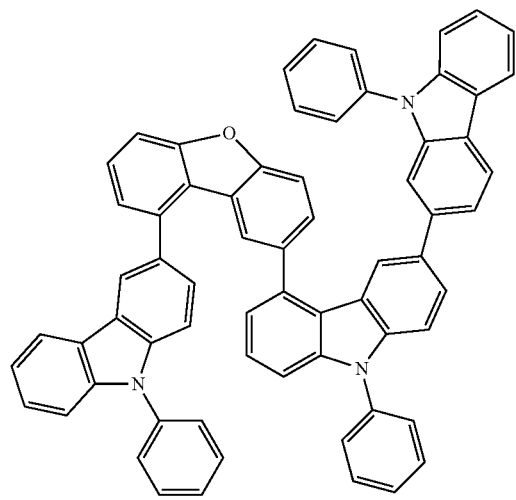
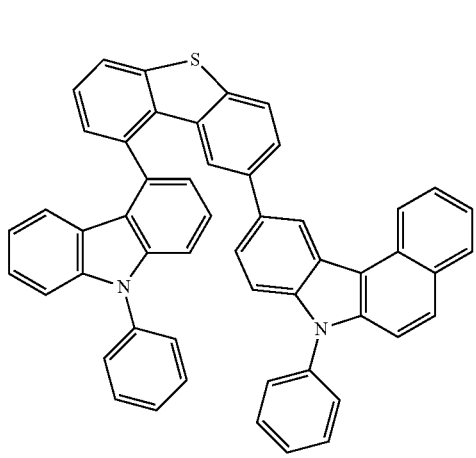
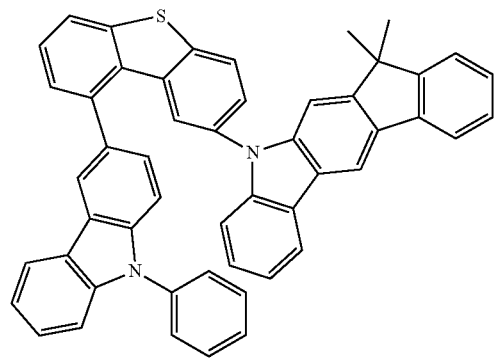
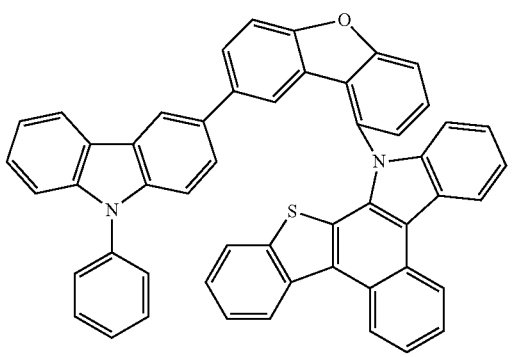
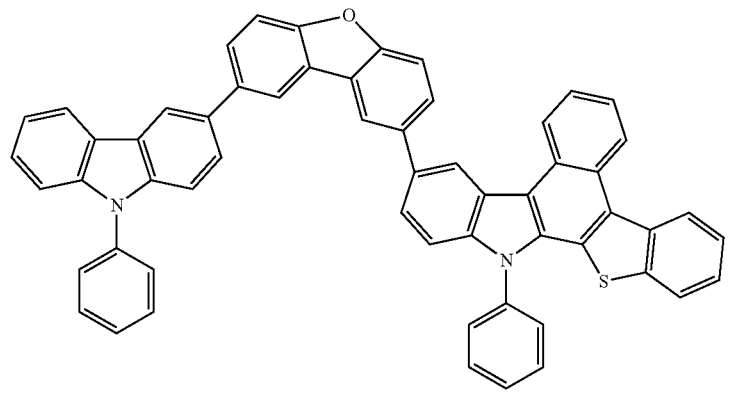
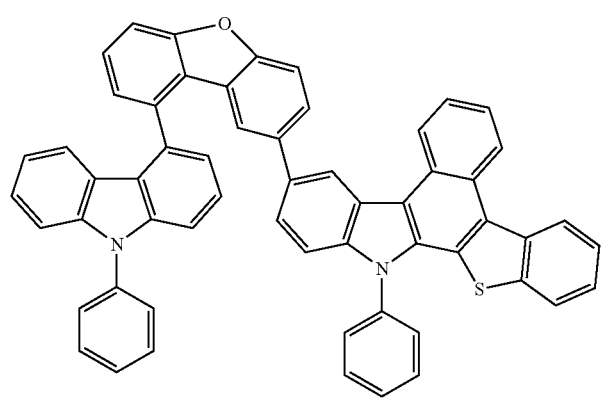
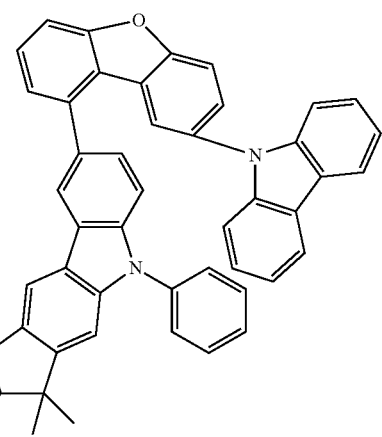

57
-continued
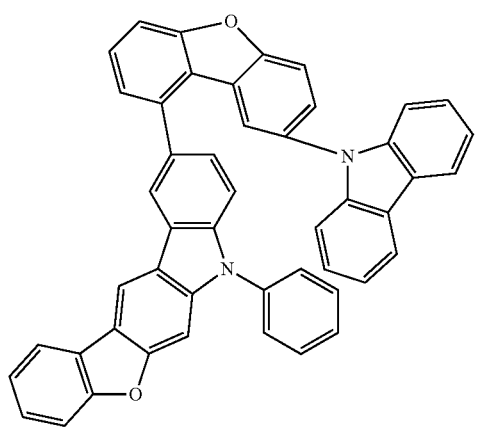
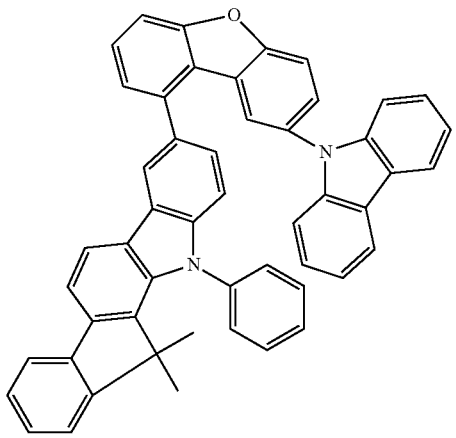
58
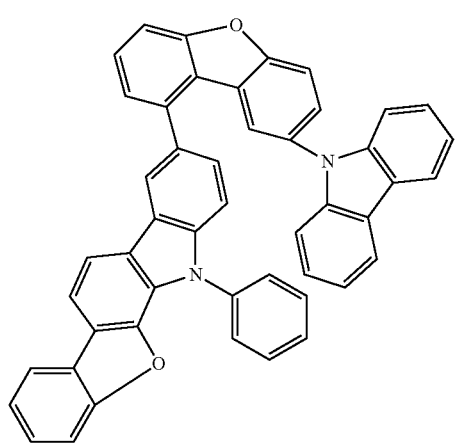
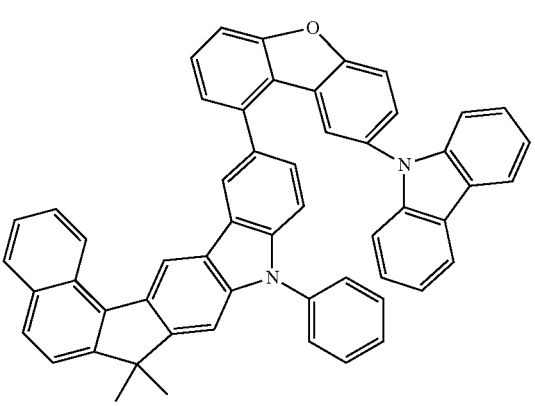
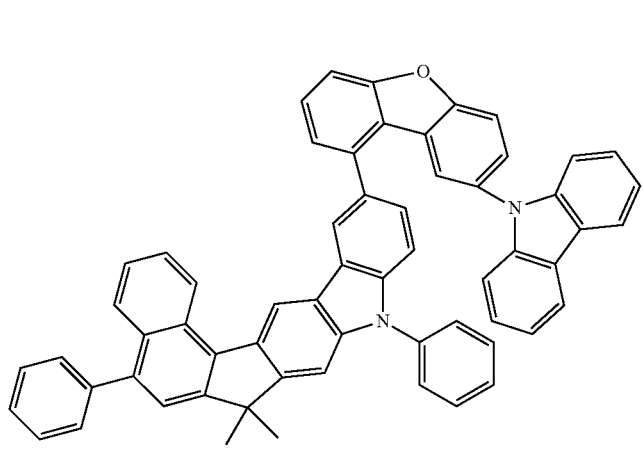
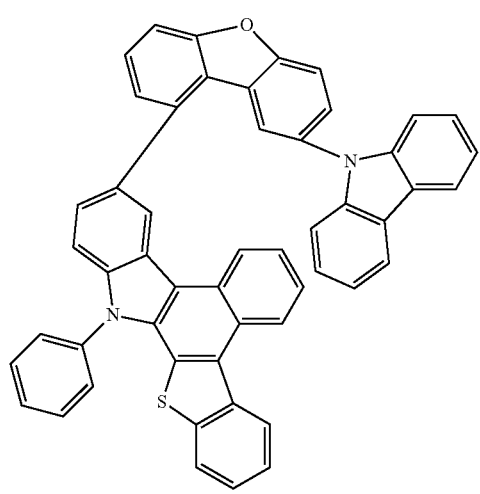

-continued
| 59 | 60 |
|---|---|
| 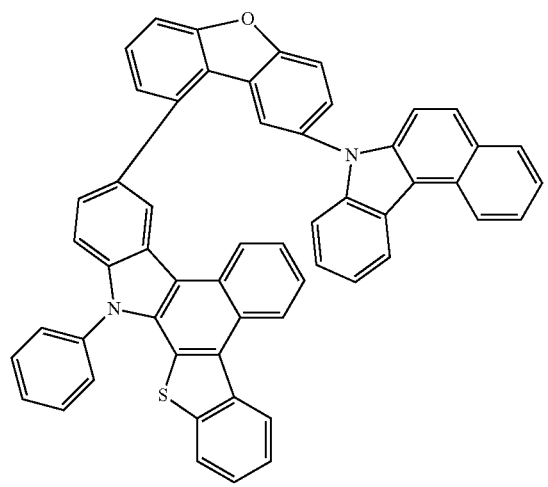 | 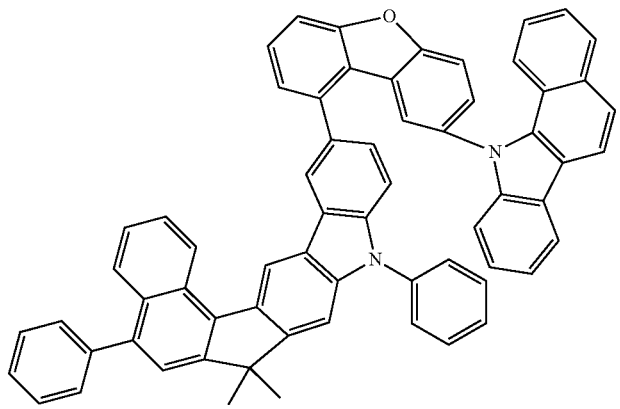 |
| 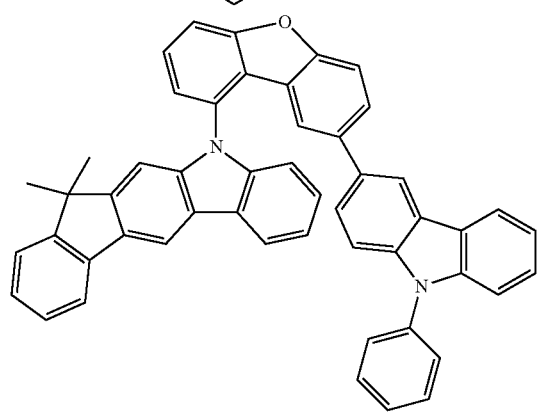 | 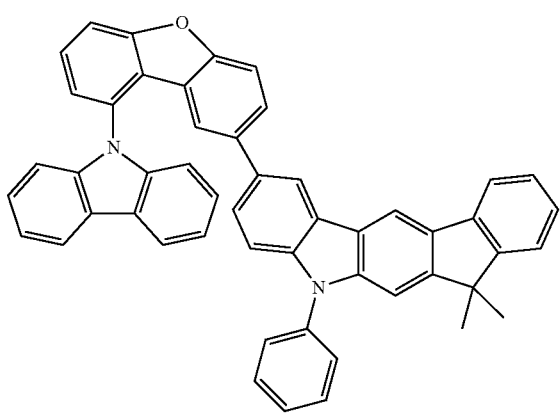 |
| 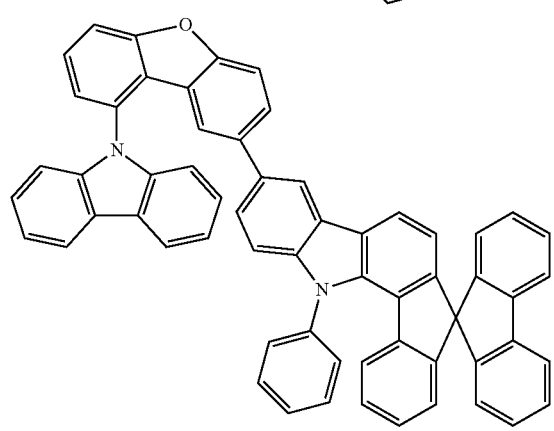 | 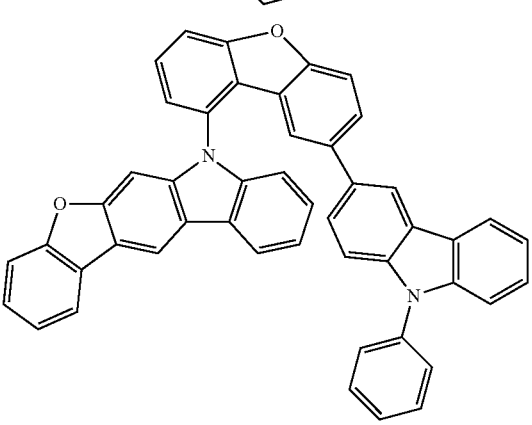 |
| 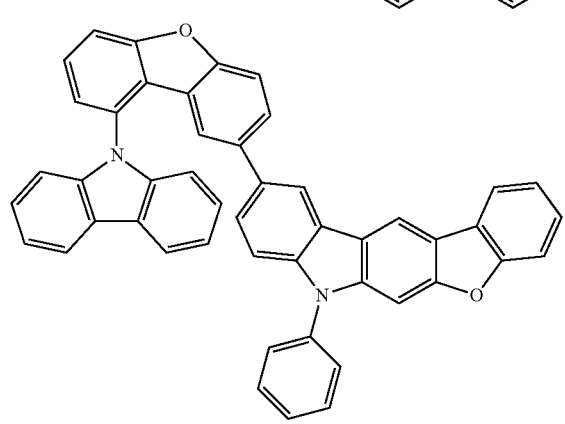 | 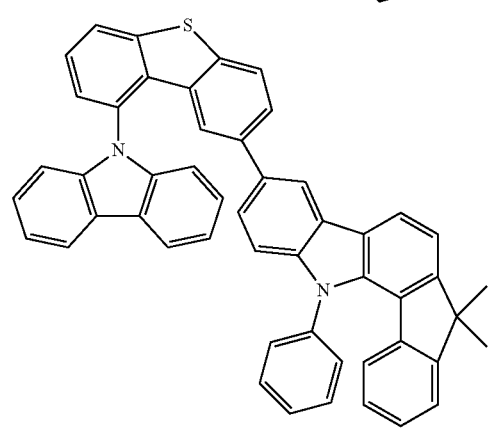 |

61 62
-continued
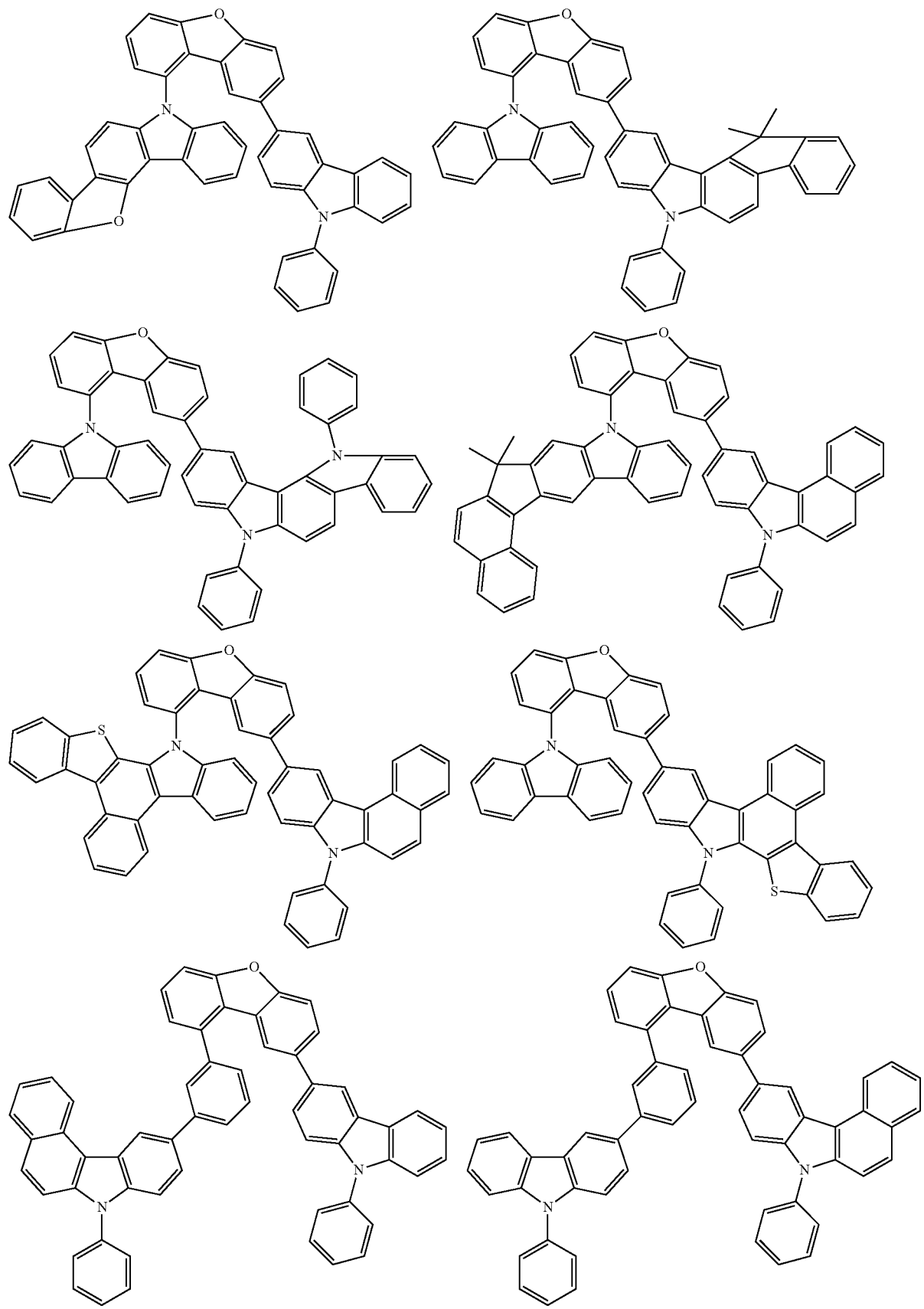

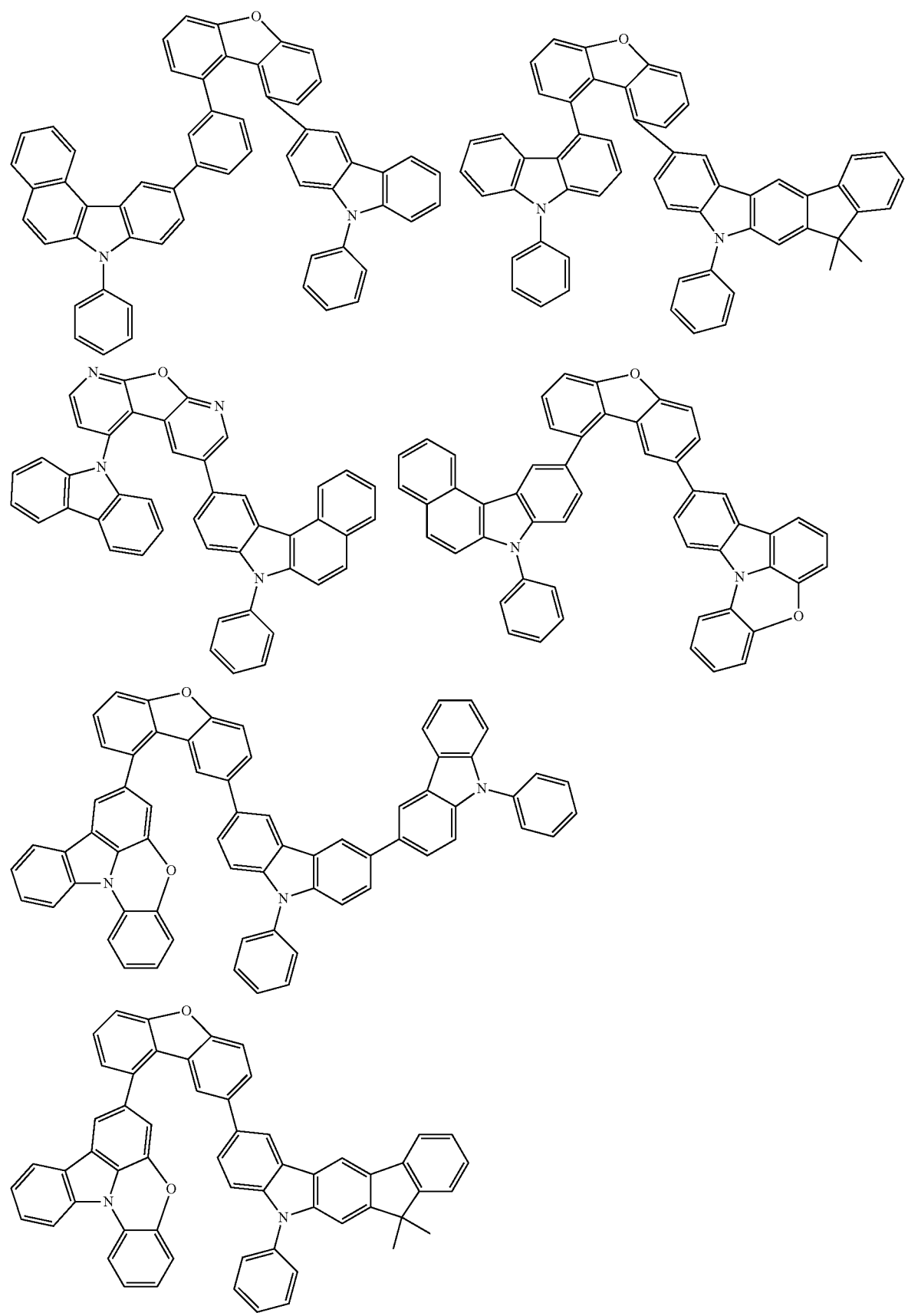

-continued
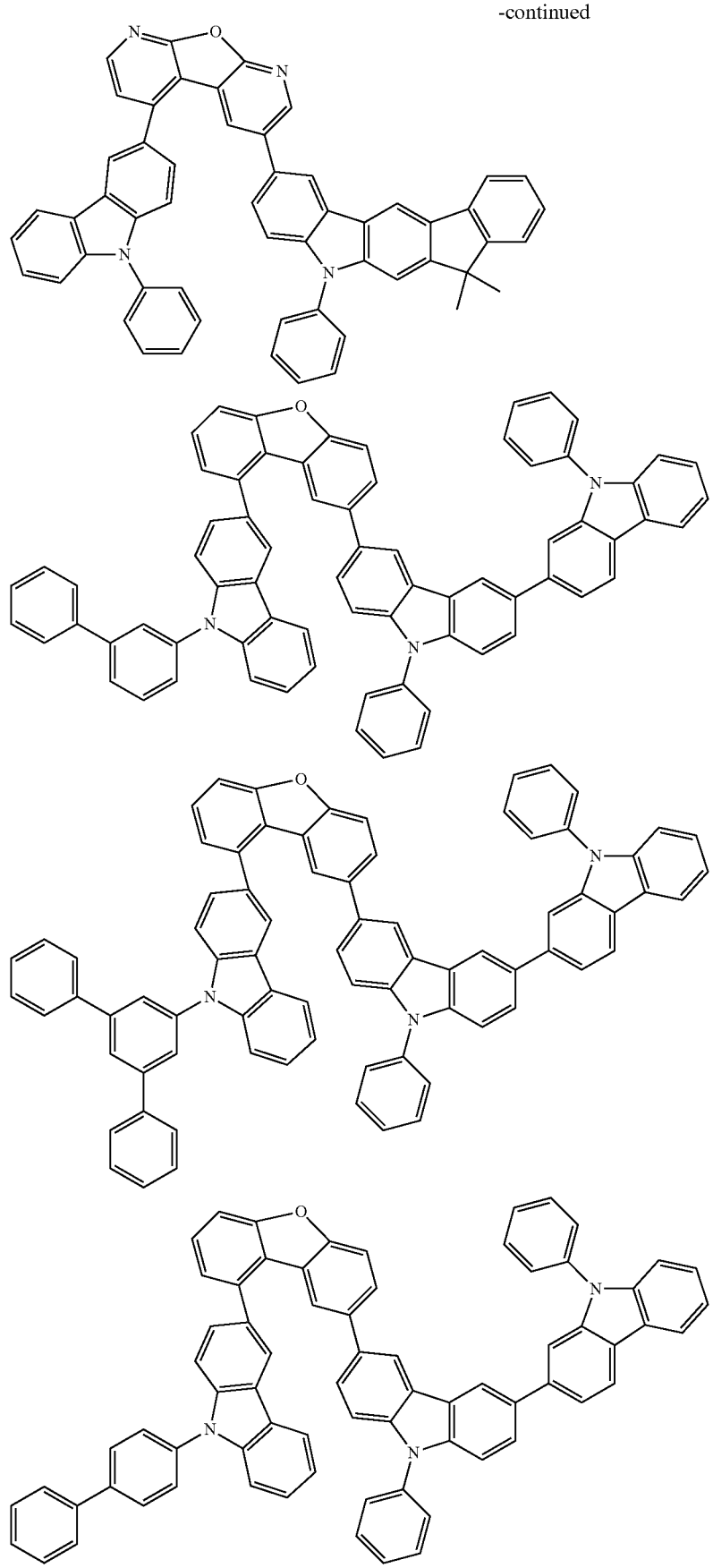

-continued
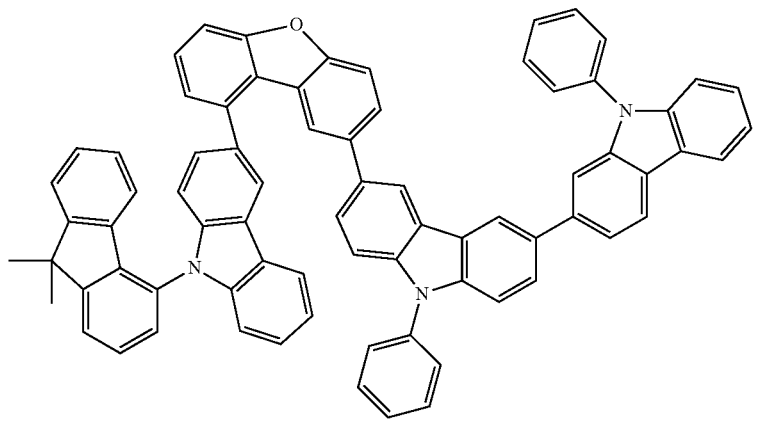
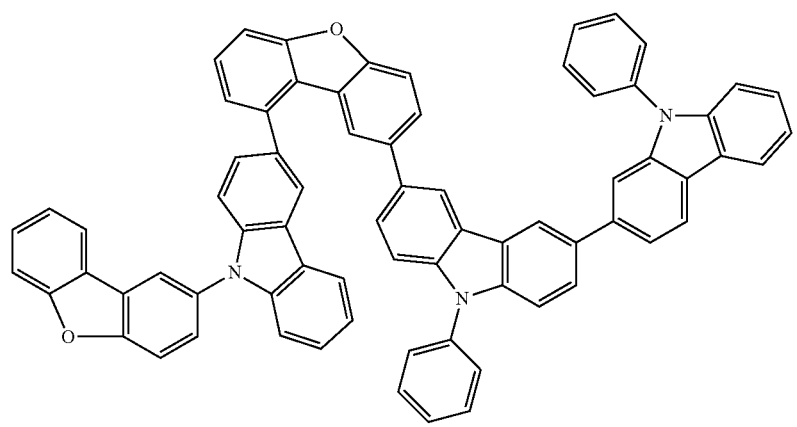
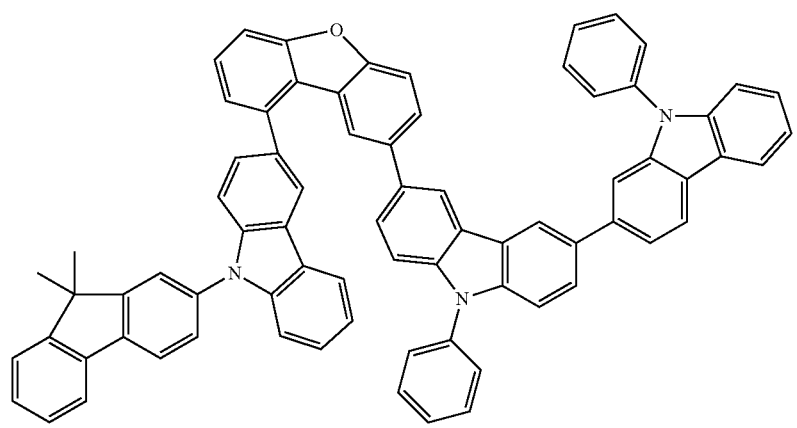

-continued
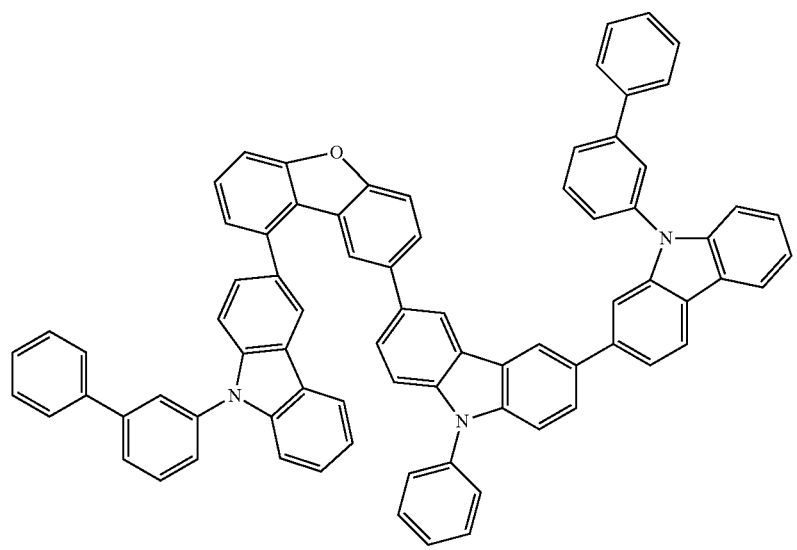
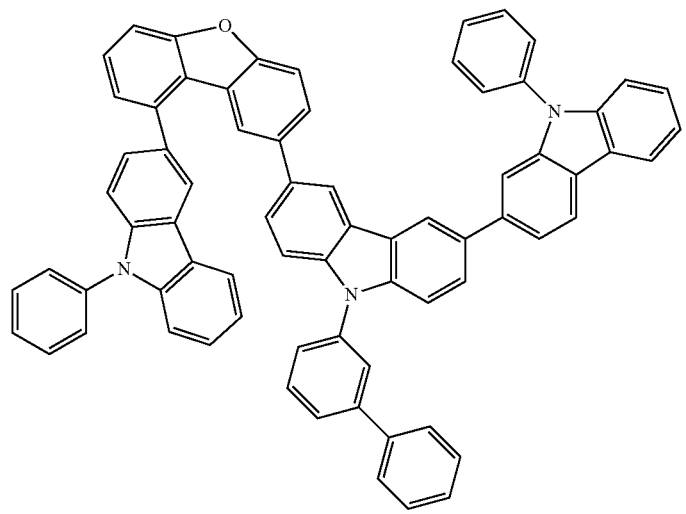
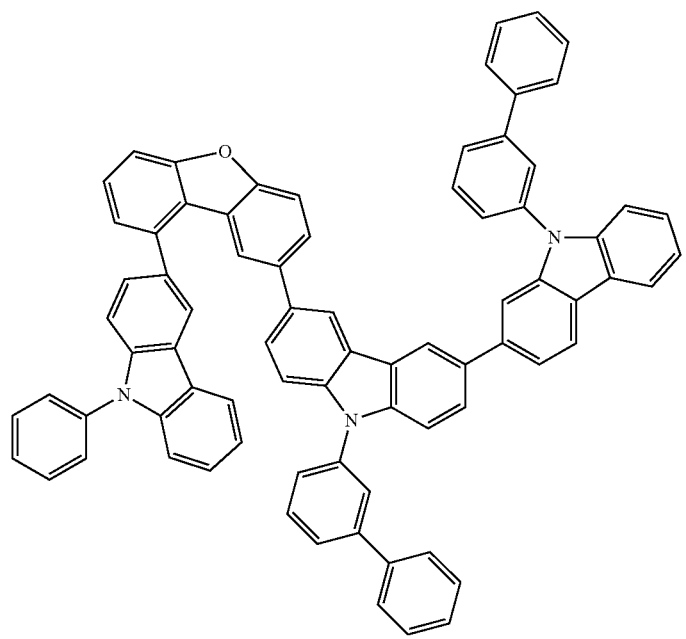

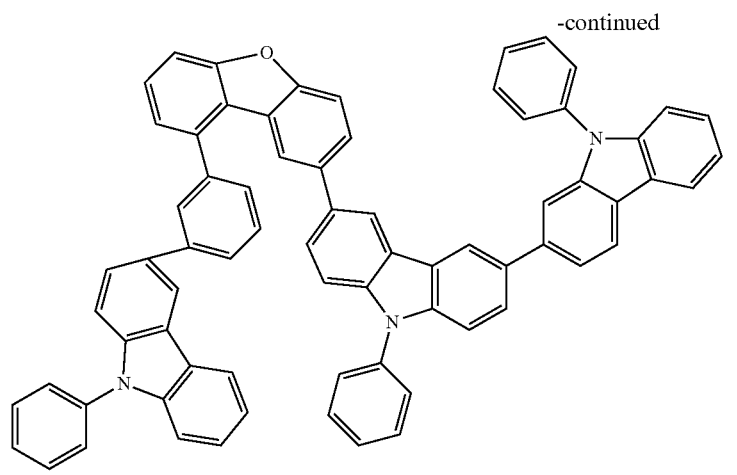

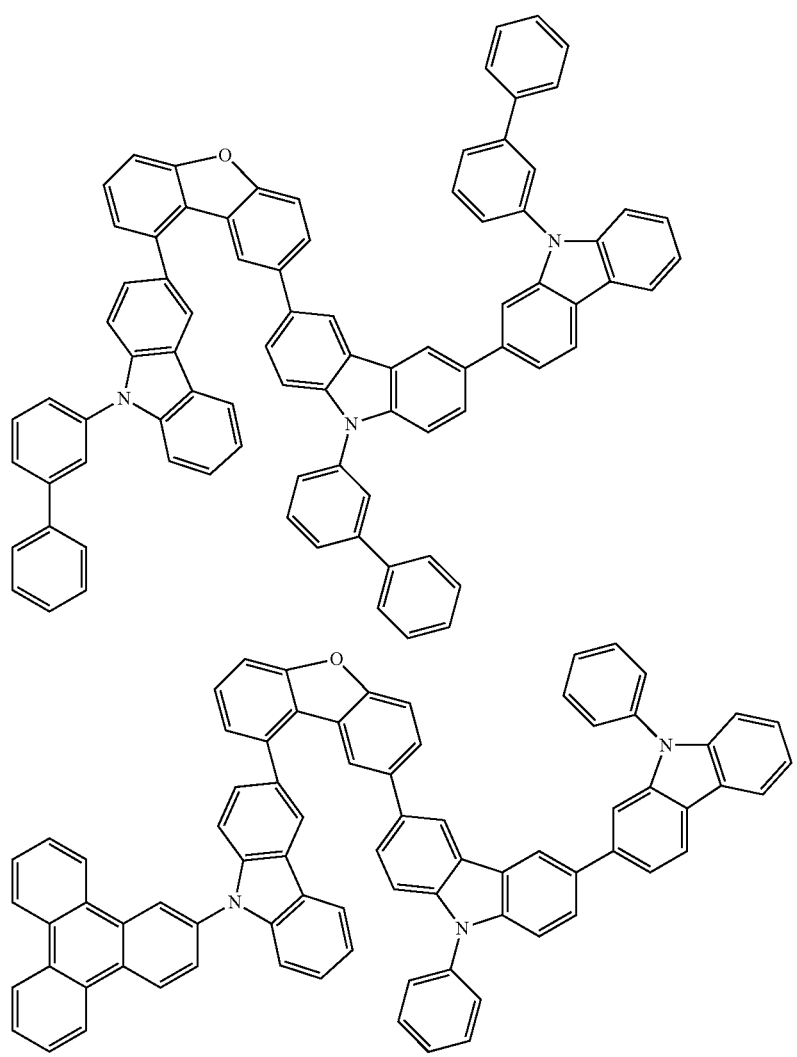

The compounds of the invention can be prepared by synthesis steps known to those skilled in the art, for example bromination, Suzuki coupling, Ullmann coupling, Hartwig-Buchwald coupling, etc. A suitable synthesis method is shown in general terms in Scheme 2 below: Scheme 1 shows the synthesis of the 1-bromo-substituted dibenzofuran which is used as reactant. Scheme 2 shows the functionalization of the dibenzofuran in the 8 position, and the conversion to the compounds of the invention.

Scheme 1

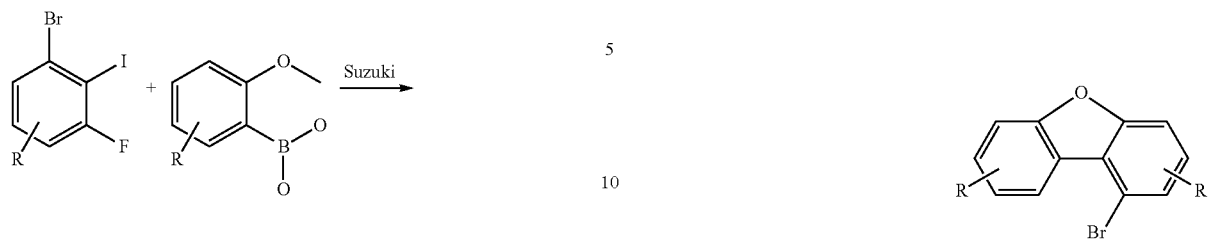

Scheme 2

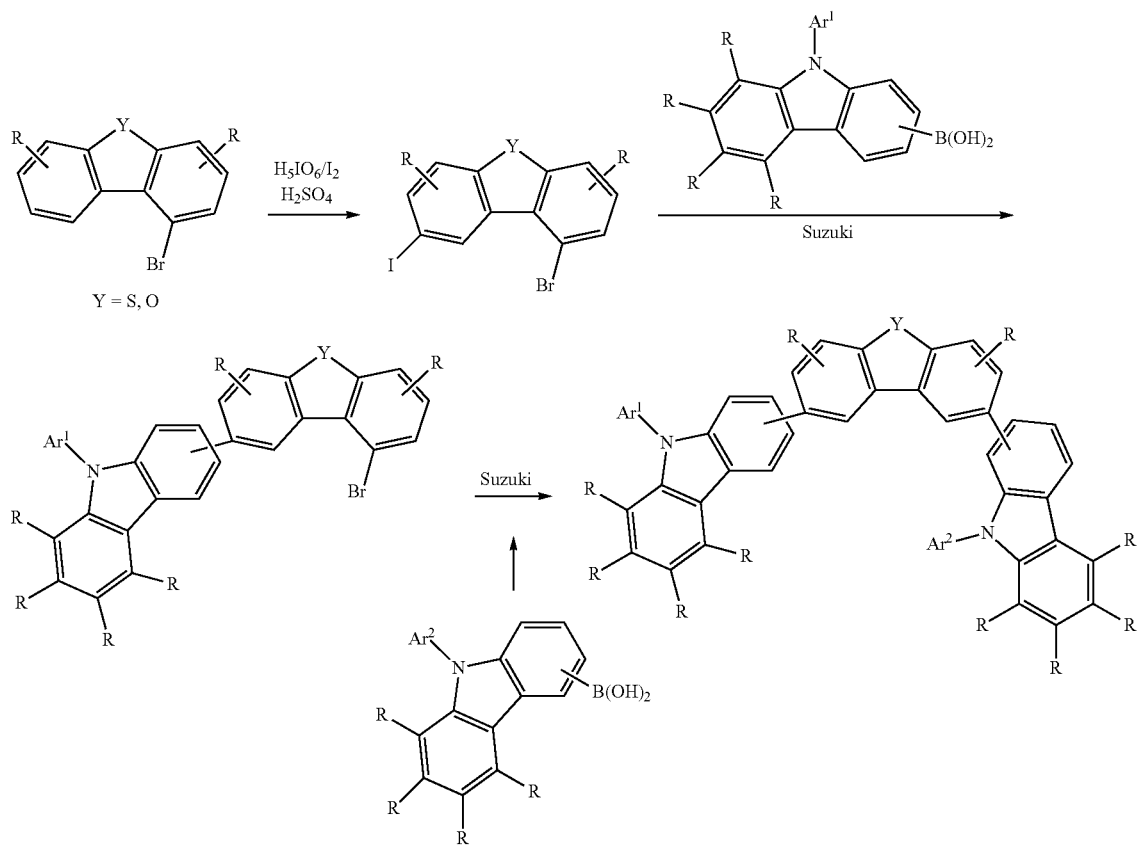

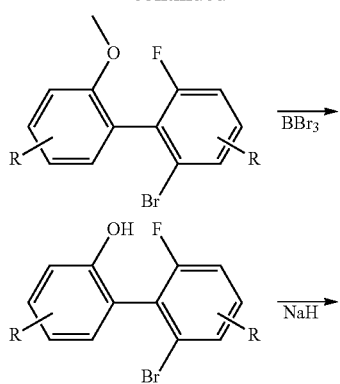

The present invention therefore further provides a process for preparing the compounds of the invention by reacting an optionally substituted 1,8-dihalodibenzofuran or 1,8-dihalodibenzothiophene or a corresponding derivative having one or more nitrogen atoms in the base skeleton with a carbazole derivative, followed by reaction with the other carbazole derivative, where the reactions with the carbazole derivatives are each C—C couplings or C—N couplings, especially Suzuki couplings or Hartwig-Buchwald couplings.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane, 2-methylbiphenyl, 3-methylbiphenyl, 1-methylnaphthalene, 1-ethylnaphthalene, ethyl octanoate, diethyl sebacate, octyl octanoate, heptylbenzene, menthyl isovalerate, cyclohexyl hexanoate or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. Suitable emitting compounds and further matrix materials are listed at the back in connection with the organic electroluminescent device. The further compound may also be polymeric.

The compounds of the invention and mixtures are suitable for use in an electronic device. An electronic device is understood to mean a device containing at least one layer containing at least one organic compound.

This component may also comprise inorganic materials or else layers formed entirely from inorganic materials.

The present invention therefore further provides for the use of the compounds or mixtures of the invention in an electronic device, especially in an organic electroluminescent device.

The present invention still further provides an electronic device comprising at least one of the above-detailed compounds or mixtures of the invention. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemical cells (LECs), organic laser diodes (O-lasers) and organic plasmon emitting devices, preferably organic electroluminescent devices (OLEDs, PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission. Also preferred are tandem OLEDs. These may be fluorescent or phosphorescent emission layers or else hybrid systems in which fluorescent and phosphorescent emission layers are combined with one another. A white-emitting electroluminescent device can be used, for example, for lighting applications, but also in combination with a colour filter for full-colour displays.

The compound of the invention according to the above-detailed embodiments may be used in different layers, according to the exact structure. Preference is given to an organic electroluminescent device containing a compound of formulae (1), (2), (3) or (4) or according to the preferred embodiments as matrix material for fluorescent or phosphorescent emitters or for emitters that exhibit TADF (thermally activated delayed fluorescence), especially for phosphorescent emitters, and/or as electron transport or hole blocker material in an electron transport layer and/or in a hole-blocking layer, according to the exact substitution. In this context, the above-detailed preferred embodiments also apply to the use of the materials in organic electronic devices.

In a preferred embodiment of the invention, the compound of formulae (1), (2), (3) or (4) or according to the preferred embodiments is used as matrix material for a phosphorescent compound in an emitting layer. In this case, the organic electroluminescent device may contain an emitting layer, or it may contain a plurality of emitting layers, where at least one emitting layer contains at least one compound of the invention as matrix material.

When the compound of formulae (1), (2), (3) or (4) or according to the preferred embodiments is used as matrix material for an emitting compound in an emitting layer, it is preferably used in combination with one or more phosphorescent materials (triplet emitters). Phosphorescence in the context of this invention is understood to mean luminescence from an excited state having spin multiplicity>1, especially from an excited triplet state. In the context of this application, all luminescent transition metal complexes and luminescent lanthanide complexes, especially all luminescent iridium, platinum and copper complexes, shall be regarded as phosphorescent compounds.

The mixture of the compound of formulae (1), (2), (3) or (4) or according to the preferred embodiments and the emitting compound contains between 99% and 1% by volume, preferably between 98% and 10% by volume, more preferably between 97% and 60% by volume and especially between 95% and 80% by volume of the compound of formulae (1), (2), (3) or (4) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material. If the compounds are processed from solution, preference is given to using the corresponding amounts in % by weight rather than the above-specified amounts in % by volume.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439 and the as yet unpublished applications EP 16179378.1 and EP 16186313.9. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

A further preferred embodiment of the present invention is the use of the compound of formulae (1), (2), (3) or (4) or according to the preferred embodiments as matrix material for a phosphorescent emitter in combination with a further matrix material. In a preferred embodiment of the invention, the further matrix material is a hole-transporting compound. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer.

Suitable matrix materials for the compounds of the invention are ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, combinations of triazines and carbazoles, for example according to WO 2011/057706 or WO 2014/015931, indolocarbazole derivatives, for example according to WO 2007/063754 or WO 2008/056746, indenocarbazole derivatives, for example according to WO 2010/136109, WO 2011/000455, WO 2013/041176 or WO 2013/056776, spiroindenocarbazole derivatives, for example according to WO 2014/094963 or WO 2015/124255, azacarbazoles, for example according to EP 1617710, EP 1617711, EP 1731584, JP 2005/347160, bipolar matrix materials, for example according to WO 2007/137725, lactams, for example according to WO 2011/116865, WO 2011/137951, WO 2013/064206 or WO 2014/056567, silanes, for example according to WO 2005/111172, azaboroles or boronic esters, for example according to WO 2006/117052 or WO 2013/091762, diazasilole derivatives, for example according to WO 2010/054729, diazaphosphole derivatives, for example according to WO 2010/054730, triazine derivatives, for example according to WO 2010/015306, WO 2007/063754, WO 2008/056746 or WO 2014/023388, zinc complexes, for example according to EP 652273 or WO 2009/062578, dibenzofuran derivatives, for example according to WO 2009/148015, WO 2015/169412, WO 2016/015810, WO 2016/023608 or WO 2017/076485, bridged carbazole derivatives, for example according to US 2009/0136779, WO 2010/050778, WO 2011/042107 or WO 2011/088877, or triphenylene derivatives, for example according to WO 2012/048781. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams, triazine derivatives and carbazole derivatives.

Preferred triarylamine derivatives which are used as co-host materials together with the compounds of the invention are selected from the compounds of the following formula (15):

Formula (15)

where Ar is the same or different at each instance and is an aromatic or heteroaromatic ring system which has 5 to 40 aromatic ring atoms and may be substituted in each case by one or more R radicals, but is preferably unsubstituted. Preferably, the Ar groups are the same or different at each instance and are selected from the abovementioned $Ar^1$-1 to $Ar^1$-19 groups, where $Y^3$ is NR', O, S or $C(R')_2$.

In a preferred embodiment of the compounds of the formula (15), at least one Ar group is selected from a biphenyl group, which may be an ortho-, meta- or para-biphenyl group. In a further preferred embodiment of the compounds of the formula (15), at least one Ar group is selected from a fluorene group or spirobifluorene group, where these groups may each be bonded to the nitrogen atom in the 1, 2, 3 or 4 position. In yet a further preferred embodiment of the compounds of the formula (15), at least one Ar group is selected from a phenylene or biphenyl group, where the group is an ortho-, meta- or para-bonded group, substituted by a dibenzofuran group, a dibenzothiophene group or a carbazole group, especially a dibenzofuran group, where the dibenzofuran or dibenzothiophene group is bonded to the phenylene or biphenyl group via the 1, 2, 3 or 4 position and where the carbazole group is bonded to the phenylene or biphenyl group via the 1, 2, 3 or 4 position or via the nitrogen atom.

In a particularly preferred embodiment of the compounds of the formula (15), one Ar group is selected from a fluorene or spirobifluorene group, especially a 4-fluorene or 4-spirobifluorene group, and one Ar group is selected from a biphenyl group, especially a para-biphenyl group, or a fluorene group, especially a 2-fluorene group, and the third Ar group is selected from a para-phenylene group or a para-biphenyl group, substituted by a dibenzofuran group, especially a 4-dibenzofuran group, or a carbazole group, especially an N-carbazole group or an N-phenyl-3-carbazole group.

Preferred indenocarbazole derivatives which are used as co-host materials together with the compounds of the invention are selected from the compounds of the following formula (16):

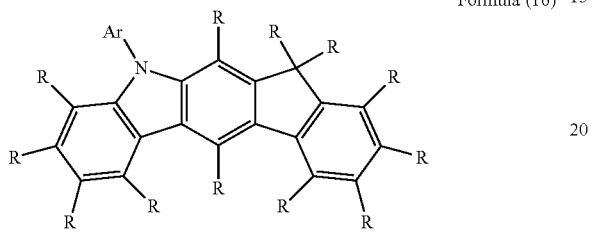

Formula (16)

where Ar and R have the definitions listed above. Preferred embodiments of the Ar group are the structures $Ar^1$-1 to $Ar^1$-19 listed above where $Y^3$ is NR', O, S or $C(R')_2$.

A preferred embodiment of the compounds of the formula (16) is the compounds of the following formula (16a):

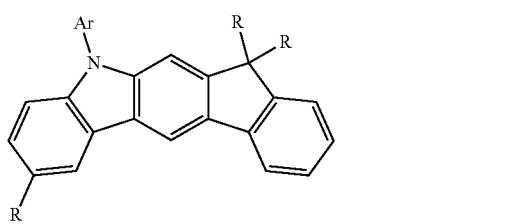

Formula (16a)

where Ar and R have the definitions given above. The two R groups bonded to the indeno carbon atom here are preferably the same or different and are each an alkyl group having 1 to 4 carbon atoms, especially methyl groups, or an aromatic ring system having 6 to 12 carbon atoms, especially phenyl groups, which may also form a ring system with one another. More preferably, the two R groups are bonded to the indeno carbon atom are methyl groups. Further preferably, the R substituent bonded to the indenocarbazole base skeleton in formula (16a) is H or a carbazole group which may be bonded to the indenocarbazole base skeleton via the 1, 2, 3 or 4 position or via the nitrogen atom, especially via the 3 position.

Preferred 4-spirocarbazole derivatives which are used as co-host materials together with the compounds of the invention are selected from the compounds of the following formula (17):

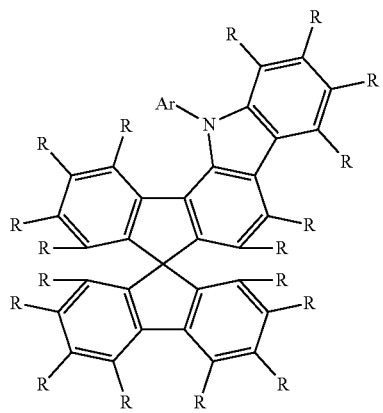

Formula (17)

where Ar and R have the definitions listed above. Preferred embodiments of the Ar group are the structures $Ar^1$-1 to $Ar^1$-19 listed above where $Y^3$ is NR', O, S or $C(R')_2$.

A preferred embodiment of the compounds of the formula (17) is the compounds of the following formula (17a):

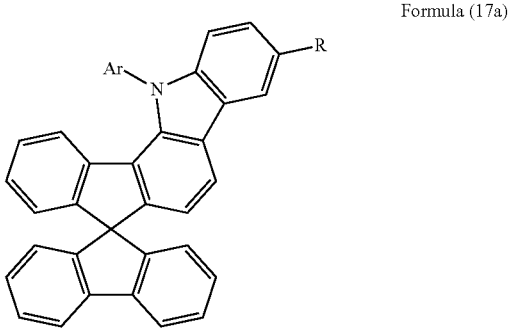

Formula (17a)

where Ar and R have the definitions given above.

Preferred lactams which are used as co-host materials together with the compounds of the invention are selected from the compounds of the following formula (18):

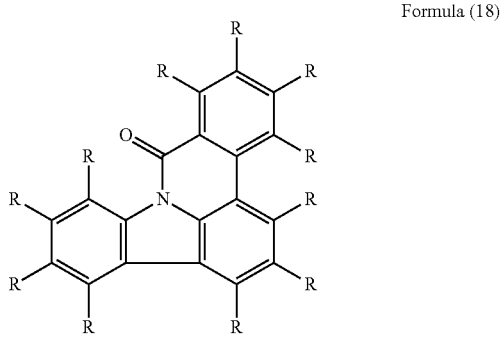

Formula (18)

where R has the definitions listed above.

A preferred embodiment of the compounds of the formula (18) is the compounds of the following formula (18a):

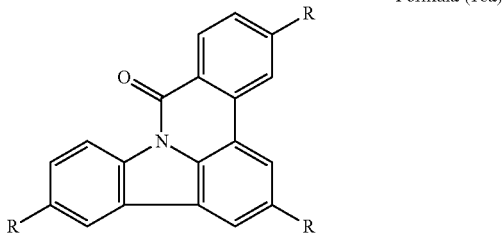

Formula (18a)

where R has the definitions given above. Preferably, R here is the same or different at each instance and is H or an aromatic or heteroaromatic ring system which has 5 to 40 aromatic ring atoms and which may be substituted by one or more $R^1$ radicals. Most preferably, the R substituents are selected from the group consisting of H and an aromatic or heteroaromatic ring system having 6 to 18 aromatic ring atoms, preferably having 6 to 13 aromatic ring atoms, each of which may be substituted by one or more nonaromatic $R^1$ radicals, but is preferably unsubstituted. Examples of suitable R substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spiro-bifluorenyl, pyridyl, pyrimidinyl, 1-, 2-, 3- or 4-dibenzofuranyl, 1-, 2-, 3- or 4-dibenzothienyl and 1-, 2-, 3- or 4-carbazolyl, each of which may be substituted by one or more $R^1$ radicals, but are preferably unsubstituted. Suitable structures R are the same structures as depicted above for $Ar^1$-1 to $Ar^1$-19, where these structures are substituted by $R^1$ rather than R and $Y^3$ is NR', 0, S or $C(R')_2$.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole blocker or electron transport layer. This is especially true when the compounds are substituted by electron-transporting groups. In addition, it is possible to use the compounds of the invention in a hole transport, hole injection or exciton blocker layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formulae (1), (2), (3) or (4) or according to the preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example inkjet printing, LITI (light-induced thermal imaging, thermal transfer printing), screen printing, flexographic printing, offset printing or nozzle printing. For this purpose, soluble compounds are needed, which are obtained, for example, through suitable substitution.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied by those skilled in the art without exercising inventive skill to organic electroluminescent devices comprising the compounds of the invention.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

The invention is now illustrated in detail by the examples which follow, without any intention of restricting it thereby.

EXAMPLES

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

a) 6-Bromo-2-fluoro-2'-methoxybiphenyl

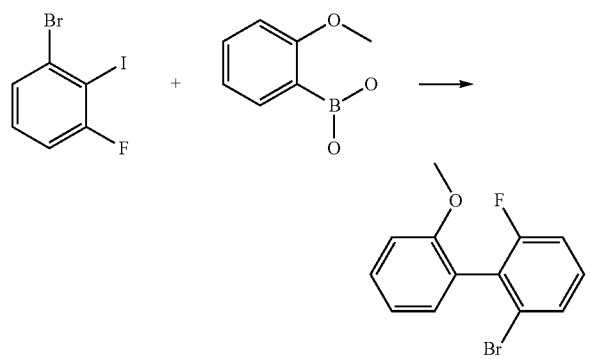

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water, and degassed. 9.3 g (13.3 mmol) of bis(triphenylphosphine)palladium(II) chloride and 1 g (20 mmol) of hydrazinium hydroxide are added. The reaction mixture is stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 155 g (553 mmol), 83% of theory.

The following compound is prepared in an analogous manner:

| | Reactant 1 | Reactant 2 | Product | Yield |
|---|---|---|---|---|
| a1 | [1000576-09-9] | | | 92% |

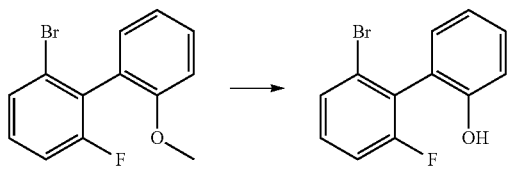 [SMILES: COc1ccccc1-c1c(F)cccc1Br ; Oc1ccccc1-c1c(F)cccc1Br]

b) 6'-Bromo-2'-fluorobiphenyl-2-ol 112 g (418 mmol) of 6-bromo-2-fluoro-2'-methoxybiphenyl are dissolved in 2 l of dichloromethane and cooled to 5° C. 41.01 ml (431 mmol) of boron tribromide are added dropwise to this solution within 90 min, and stirring of the mixture continues overnight. The mixture is subsequently admixed gradually with water, and the organic phase is washed three times with water, dried over $Na_2SO_4$ and concentrated by rotary evaporation and purified by chromatography. Yield: 104 g (397 mmol), 98% of theory.

The following compound is prepared in an analogous manner:

| | Reactant 1 | Product | Yield |
|---|---|---|---|
| b1 | | | 92% |

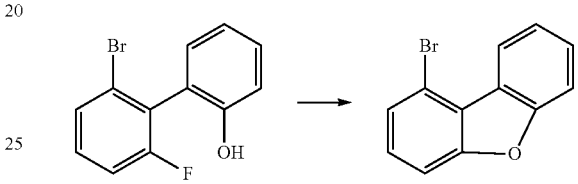

c) 1-Bromodibenzofuran 111 g (416 mmol) of 6'-bromo-2'-fluorobiphenyl-2-ol are dissolved in 2 l of DMF (max. 0.003% $H_2O$) SeccoSolv® and cooled to 5° C. 20 g (449 mmol) of sodium hydride (60% suspension in paraffin oil) are added to this solution in portions, once the addition has ended the mixture is stirred for 20 min, and then the mixture is heated to 100° C. for 45 min. After cooling, 500 ml of ethanol are added gradually to the mixture, which is concentrated by rotary evaporation and then purified by chromatography. Yield: 90 g (367 mmol), 88.5% of theory.

The following compound is prepared in an analogous manner:

| | Reactant 1 | Product | Yield |
|---|---|---|---|
| c1 | | | 81% | d) 1-Bromo-8-iododibenzofuran e) 3-(9-Bromodibenzofuran-2-yl)-9-phenyl-9H-carbazole

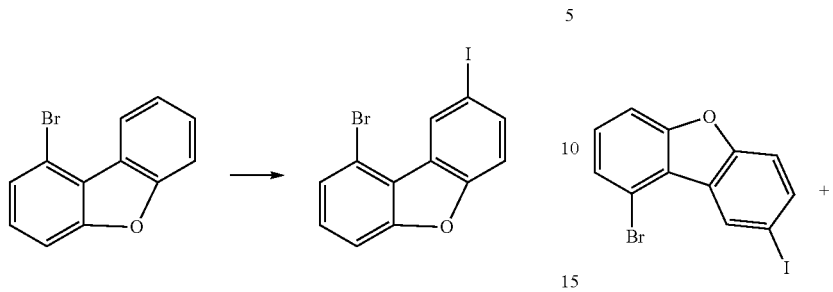

20 g (80 mmol) of 1-bromodibenzofuran, 2.06 g (40.1 mmol) of iodine, 3.13 g (17.8 mmol) of iodic acid, 80 ml of acetic acid and 5 ml of sulphuric acid and 5 ml of water and 2 ml of chloroform are stirred at 65° C. for 3 h. After cooling, the mixture is admixed with water, and the precipitated solids are filtered off with suction and washed three times with water. The residue is recrystallized from toluene and from dichloromethane/heptane. The yield is 25.6 g (68 mmol), corresponding to 85% of theory.

The following compounds are prepared in an analogous manner:

| | Reactant 1 | Product | Yield |
|---|---|---|---|
| d1 | [65642-94-6] | | 81% |
| d2 | | | 67% |

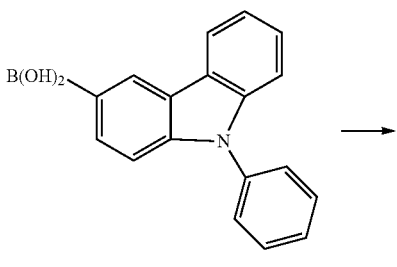

58 g (156 mmol) of 1-bromo-8-iododibenzofuran, 50 g (172 mmol) of N-phenylcarbazole-3-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The yield is 48 g (89 mmol), corresponding to 64% of theory.

The following compounds are prepared in an analogous manner:

| | Reactant 1 | Reactant 2 | Product | Yield |
|---|---|---|---|---|
| e1 | | [1807978-29-5] | | 67% |
| e2 | | [1807910-31-1] | | 65% |
| e3 | | [1001911-63-2] | | 62% |

-continued
| Reactant 1 | Reactant 2 | Product | Yield |
|---|---|---|---|
| e4 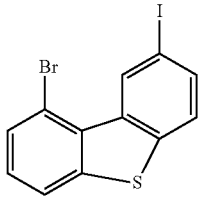 [SMILES: Brc1cccc2sc3ccc(I)cc3c12] d1 | 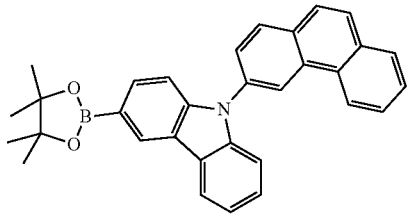 [1801609-54-0] | 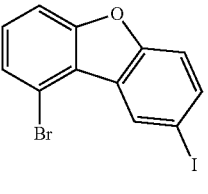 [SMILES: Brc1cccc2oc3ccc(I)cc3c12] | 63% |
| e5 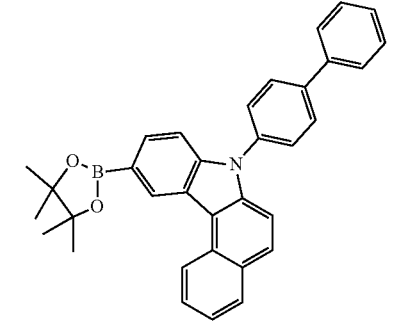 | 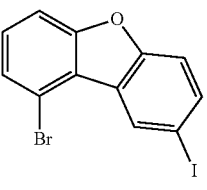 [SMILES: Brc1cccc2oc3ccc(I)cc3c12] 1493716-02-1] | 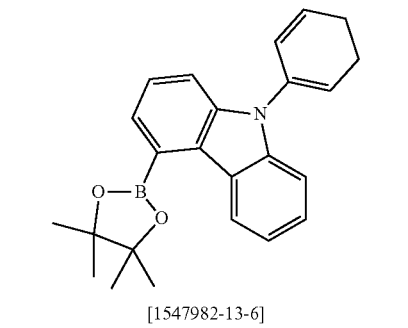 [SMILES: CC1(C)OB(c2cccc3c2c2ccccc2n3C2=CCCC=C2)OC1(C)C] | 61% |
| e6 | | | 60% |

-continued
| | Reactant 1 | Reactant 2 | Product | Yield |
|---|---|---|---|---|
| e7 | 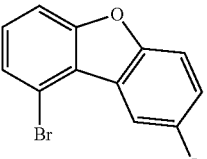 | 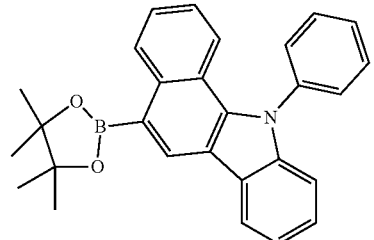<br>[1493715-37-9] | 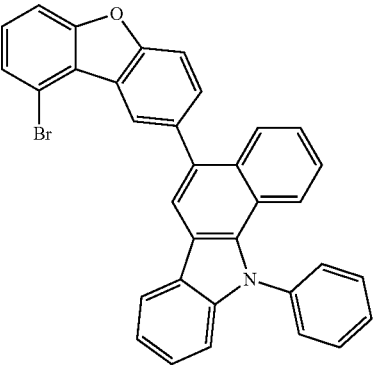 [SMILES: Brc1cccc2oc3ccc(-c4cc5c6ccccc6n(-c6ccccc6)c5c5ccccc45)cc3c12] | 56% |
| e8 | 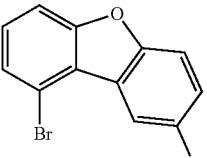 | 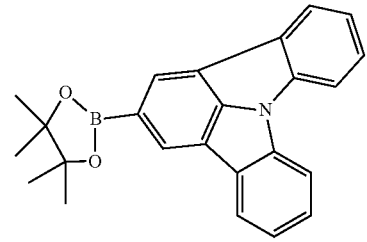<br>[1369369-44-7] | 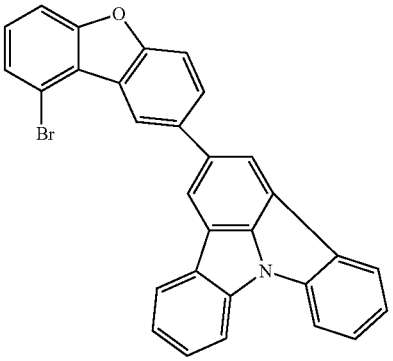 [SMILES: Brc1cccc2oc3ccc(-c4cc5c6ccccc6n6c7ccccc7c(c4)c56)cc3c12] | 54% |
| e9 | 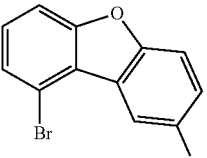 | 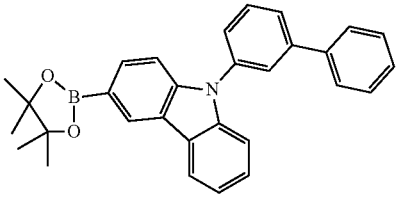<br>[1416814-68-0] | 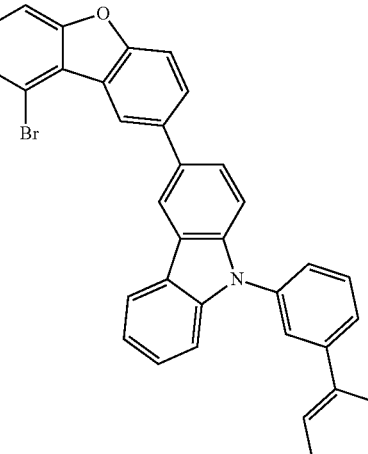 | 68% |
| e10 | 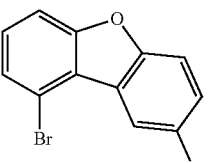 | 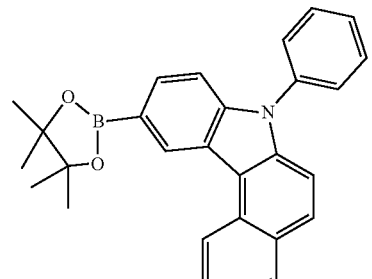<br>[1246562-39-9] | 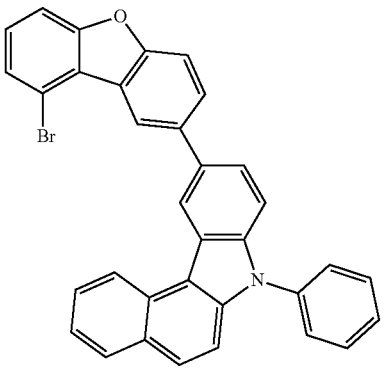 [SMILES: Brc1cccc2oc3ccc(-c4ccc5c(c4)c4c6ccccc6ccc4n5-c4ccccc4)cc3c12] | 67% |

-continued
| Reactant 1 | Reactant 2 | Product | Yield |
|---|---|---|---|
| e11 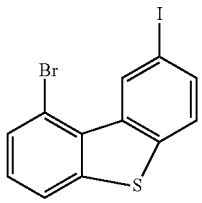 [SMILES: Brc1cccc2sc3ccc(I)cc3c12] | 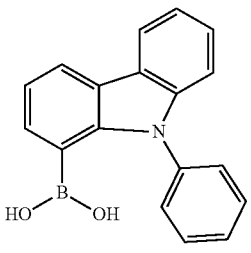 [1333002-41-7] | 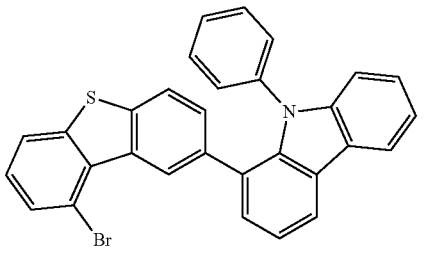 [SMILES: Brc1cccc2sc3ccc(-c4cccc5c6ccccc6n(-c6ccccc6)c45)cc3c12] | 57% |
| e12 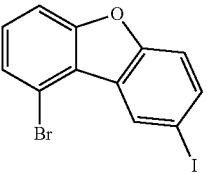 [SMILES: Brc1cccc2oc3ccc(I)cc3c12] | 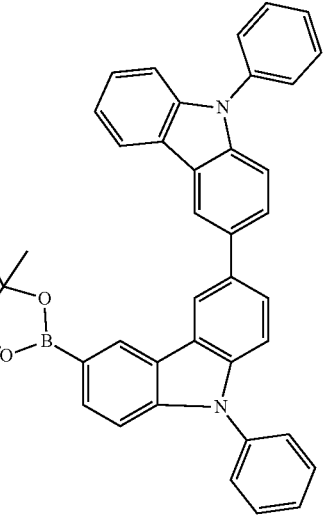 [1572537-61-1] | 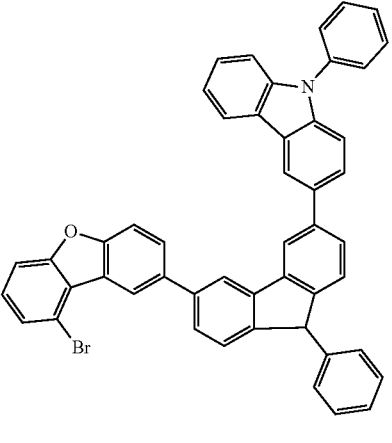 | 60% |
| e13 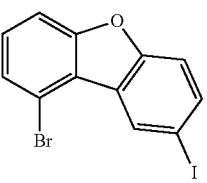 [SMILES: Brc1cccc2oc3ccc(I)cc3c12] | 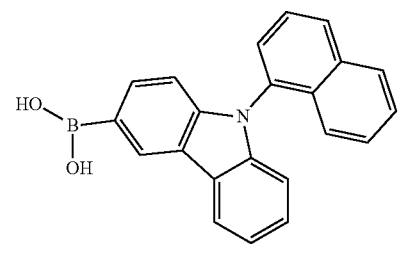 [1133057-97-2] | 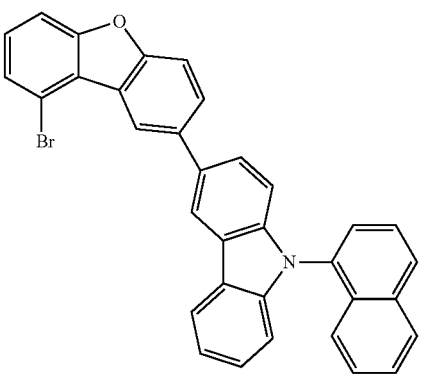 [SMILES: Brc1cccc2oc3ccc(-c4ccc5c(c4)c4ccccc4n5-c4cccc5ccccc45)cc3c12] | 63% |

-continued
| | Reactant 1 | Reactant 2 | Product | Yield |
|---|---|---|---|---|
| e14 |  | 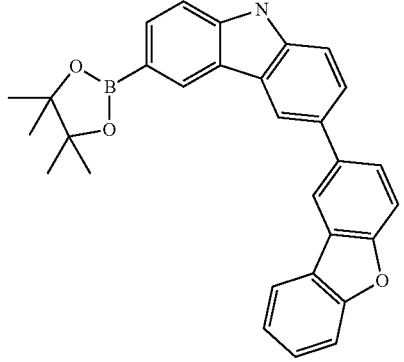 [1582802-01-4] | 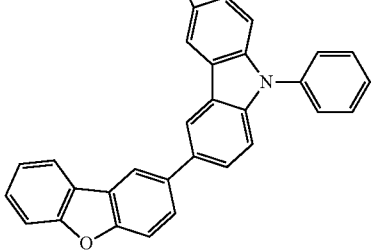 | 63% |
| e15 | 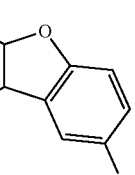 | 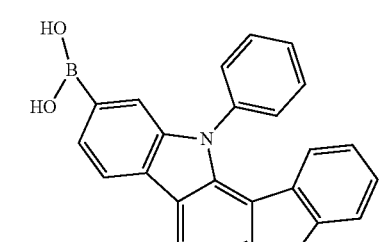 [1628070-74-5] | 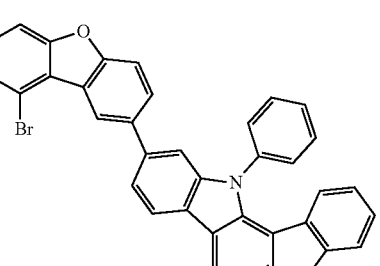 | 59% |
| e16 | 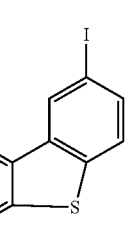 | 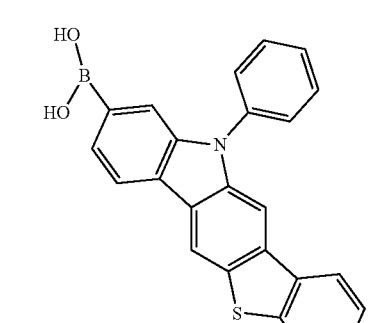 [1628070-49-4] | 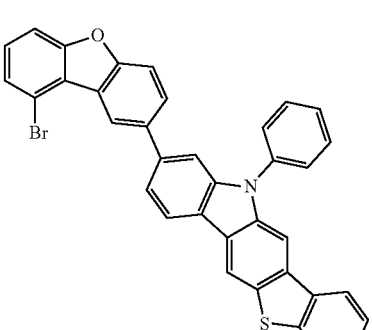 | 71% |
| e17 | 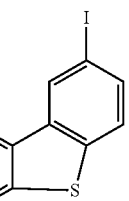 | 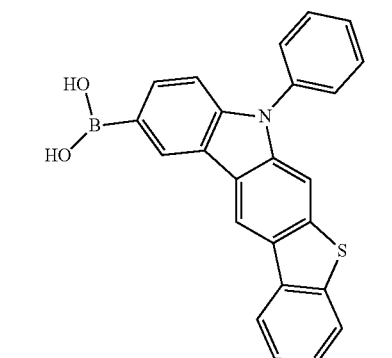 [1612243-83-0] | 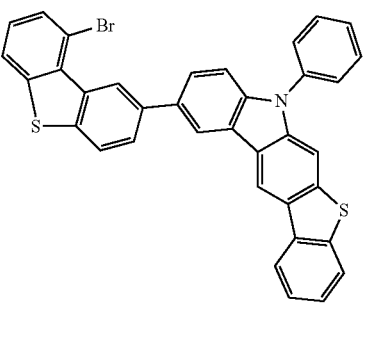 [SMILES: Brc1cccc2sc3ccc(-c4ccc5c(c4)c4cc6c(cc4n5-c4ccccc4)sc4ccccc46)cc3c12] | 70% |

-continued
| | Reactant 1 | Reactant 2 | Product | Yield |
|---|---|---|---|---|
| e18 | 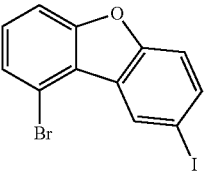 [SMILES: Brc1cccc2oc3ccc(I)cc3c12] | 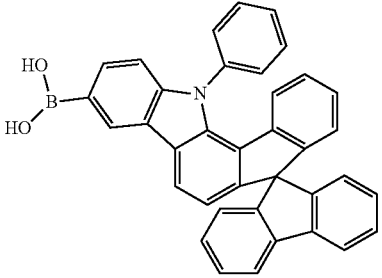 [1616232-07-5] | 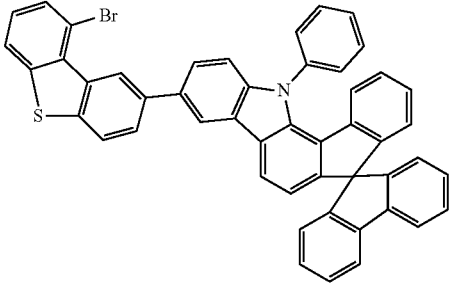 [SMILES: Brc1cccc2sc3ccc(-c4ccc5c(c4)c4ccc6c(c4n5-c4ccccc4)-c4ccccc4C64c5ccccc5-c5ccccc54)cc3c12] | 65% |
| e19 | 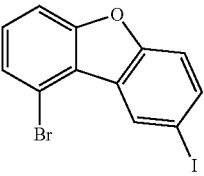 [SMILES: Brc1cccc2oc3ccc(I)cc3c12] | 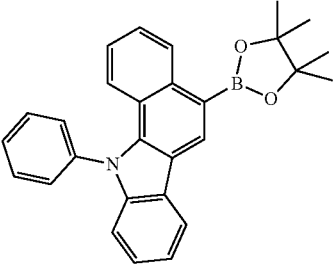 [1493715-37-9] | 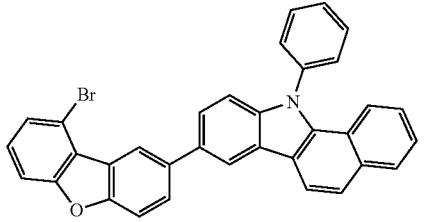 [SMILES: Brc1cccc2oc3ccc(-c4ccc5c(c4)c4ccc6ccccc6c4n5-c4ccccc4)cc3c12] | 75% |
| e20 | 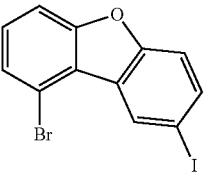 [SMILES: Brc1cccc2oc3ccc(I)cc3c12] | 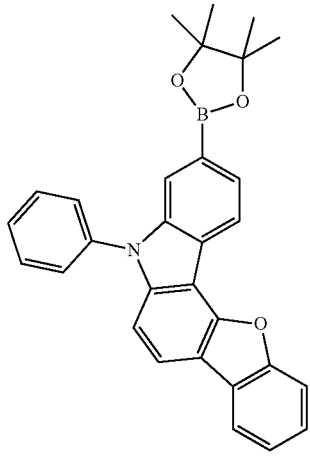 [1391729-62-6] | 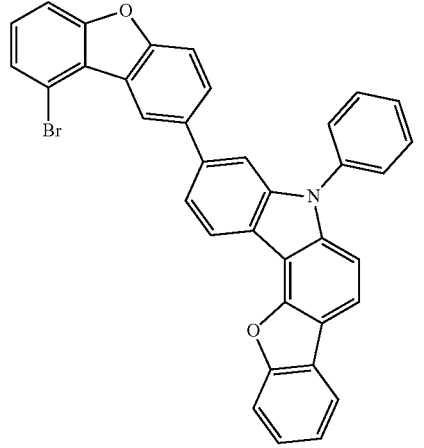 [SMILES: Brc1cccc2oc3ccc(-c4ccc5c6c7oc8ccccc8c7ccc6n(-c6ccccc6)c5c4)cc3c12] | 71% |
| e21 | 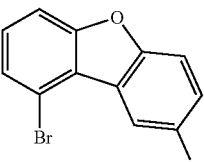 | 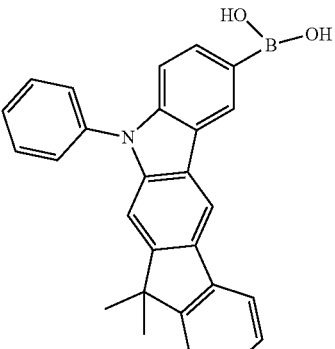 [1379585-25-7] | 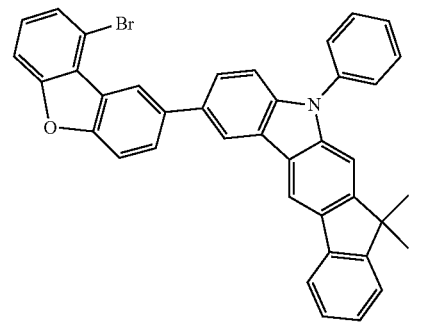 [SMILES: CC1(C)c2ccccc2-c2cc3c4cc(-c5ccc6oc7cccc(Br)c7c6c5)ccc4n(-c4ccccc4)c3cc21] | 72% |

-continued
| | Reactant 1 | Reactant 2 | Product | Yield |
|---|---|---|---|---|
| e22 | 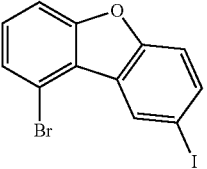 [SMILES: Brc1cccc2oc3ccc(I)cc3c12] | 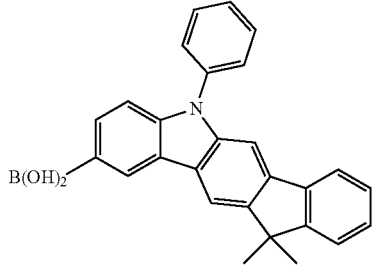
[1373359-70-6] | 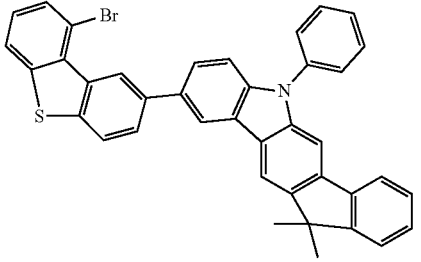 [SMILES: CC1(C)c2ccccc2-c2cc3c(cc21)c1cc(-c2ccc4sc5cccc(Br)c5c4c2)ccc1n3-c1ccccc1] | 70% |
| e23 | 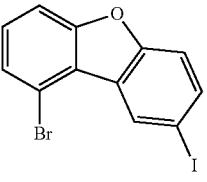 [SMILES: Brc1cccc2oc3ccc(I)cc3c12] | 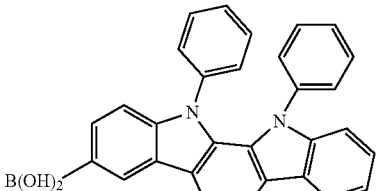
[1373359-67-1] | 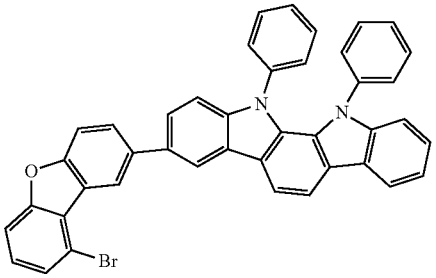 [SMILES: Brc1cccc2oc3ccc(-c4ccc5c(c4)c4ccc6c7ccccc7n(-c7ccccc7)c6c4n5-c4ccccc4)cc3c12] | 77% |
| e24 | 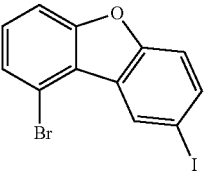 [SMILES: Brc1cccc2oc3ccc(I)cc3c12] | 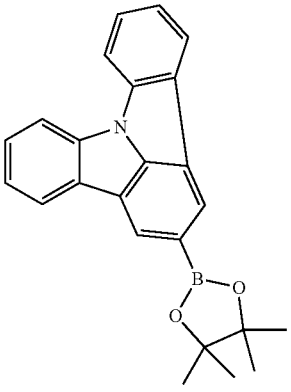
[1369369-44-7] | 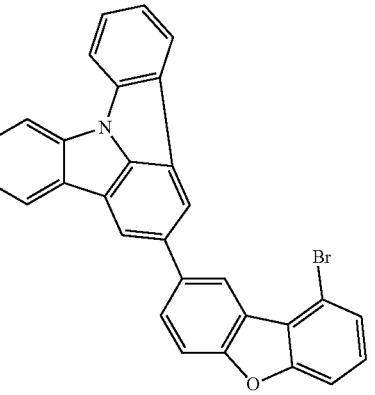 | 74% |
| e25 | 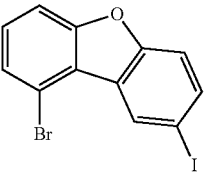 [SMILES: Brc1cccc2oc3ccc(I)cc3c12] | 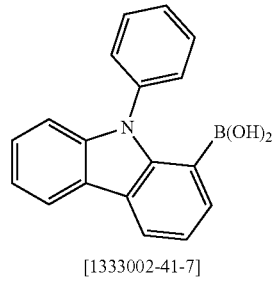 [SMILES: OB(O)c1cccc2c3ccccc3n(-c3ccccc3)c12]
[1333002-41-7] | 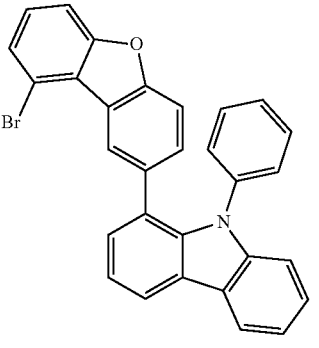 [SMILES: Brc1cccc2oc3ccc(-c4cccc5c6ccccc6n(-c6ccccc6)c45)cc3c12] | 62% |

-continued

| Reactant 1 | Reactant 2 | Product | Yield |
|---|---|---|---|
| e26 | [1313395-20-8] | | 67% |
| e27 | [1267981-76-9] | | 66% |
| e28 | [419536-33-7] | | 63% | f) 2,12-Dimethyl-10-phenyl-7-[8-(9-phenyl-9H-carbazol-3-yl)dibenzofuran 1-yl]-10,12-dihydro-10-aza-indeno[2,1-b]fluorene

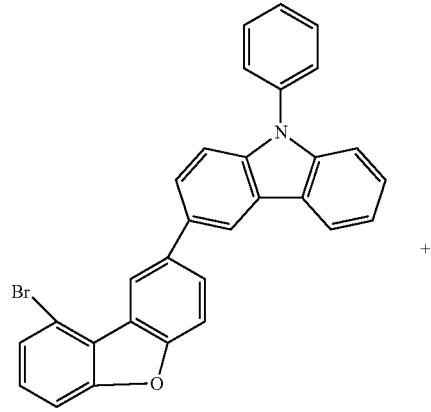

+

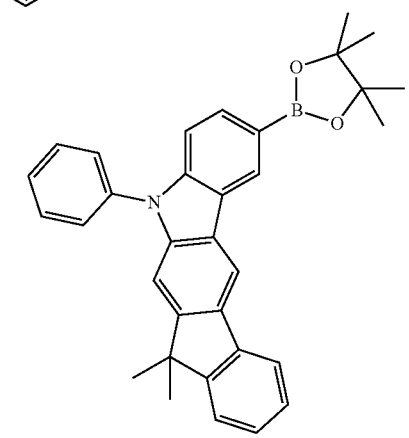

[1357150-79-8]

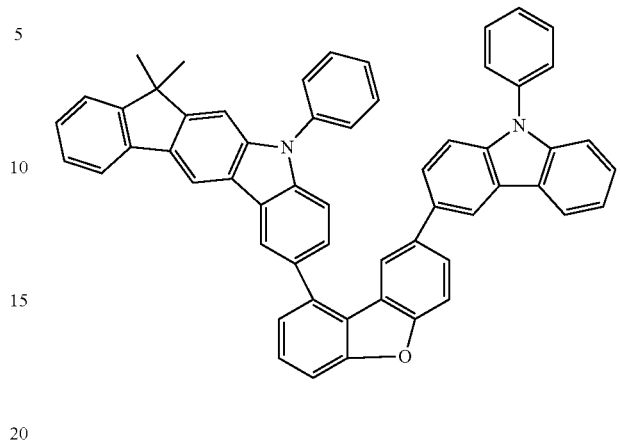

83 g (156 mmol) of 3-(9-bromodibenzofuran-2-yl)-9-phenyl-9H-carbazole, 90 g (172 mmol) of 5,7-dihydro-7,7-dimethyl-5-phenyl-2-(4,4,5,5-tetramethyl-1,3,2-dioxaborolan-2-yl)indeno[2,1-b]carbazole and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml each time of water and then concentrated to dryness. The residue is recrystallized five times from DMF and finally fractionally sublimed twice (p about $10^{-6}$ mbar, T=350-370° C.). Yield: 92 g (120 mmol), 70% of theory; purity: 99.9% by HPLC.

The following compounds are prepared in an analogous manner:

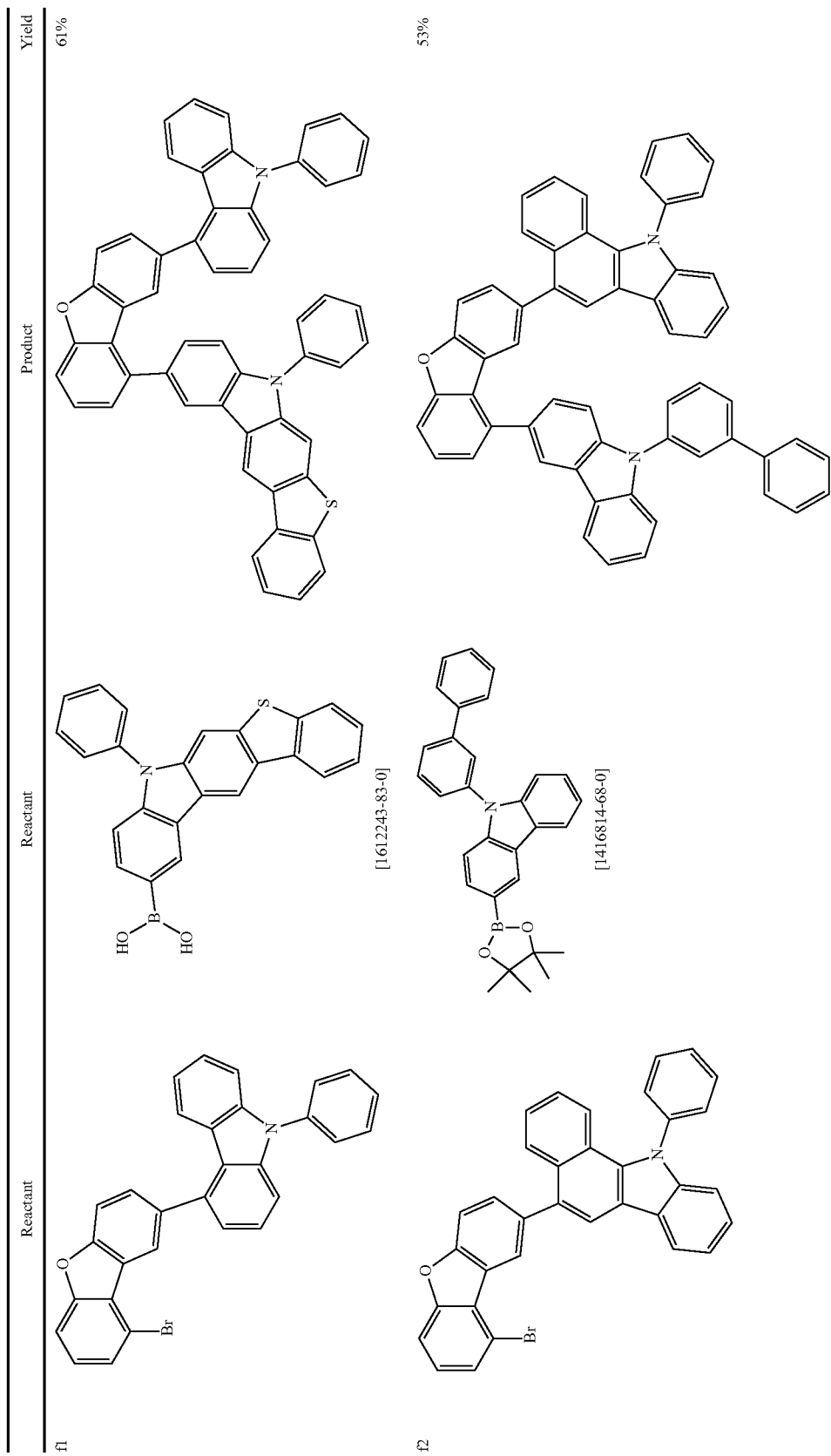

| Reactant | Reactant | Product | Yield |
|---|---|---|---|
| 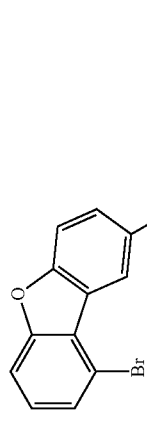 | 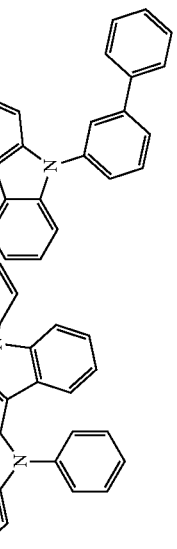 [1267981-76-9] | 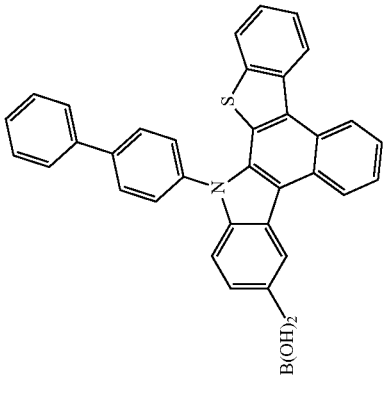 | 63% |
| 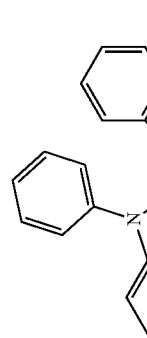 | 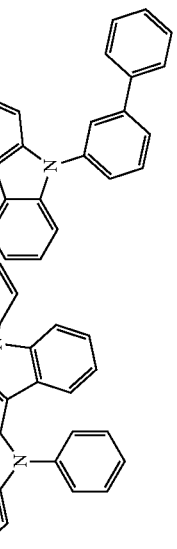 [1313395-20-8] | 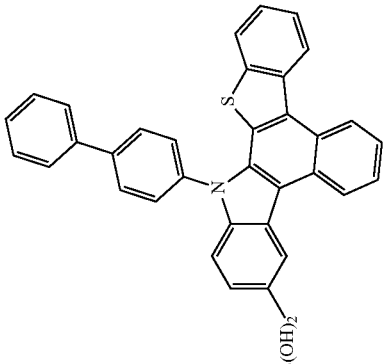 | 62% |

-continued
| | Reactant | Reactant | Product | Yield |
|---|---|---|---|---|
| f5 | 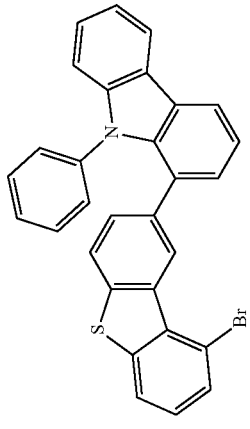 | 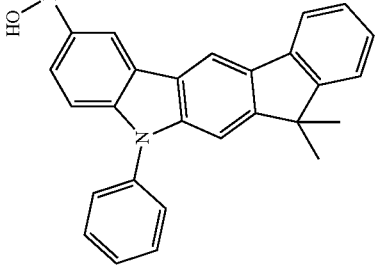 | 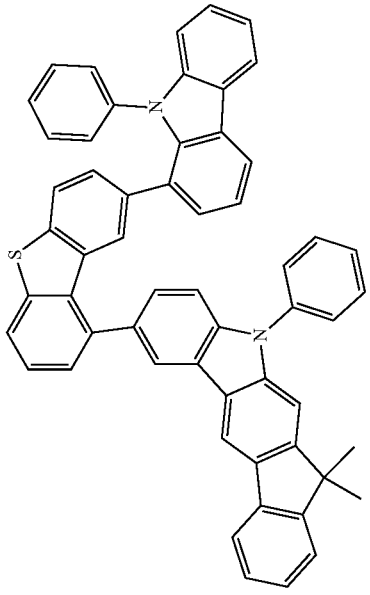 | 51% |
| f6 | 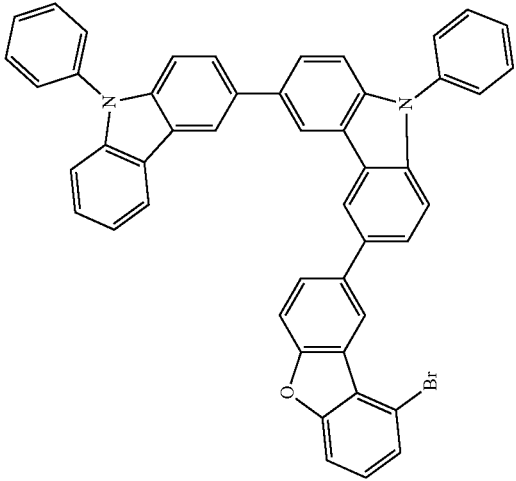 | 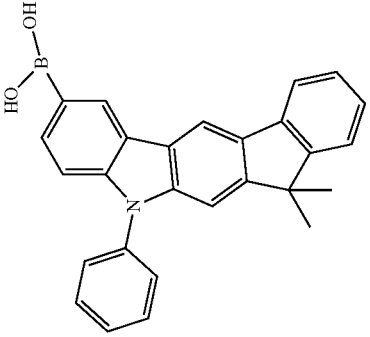 | 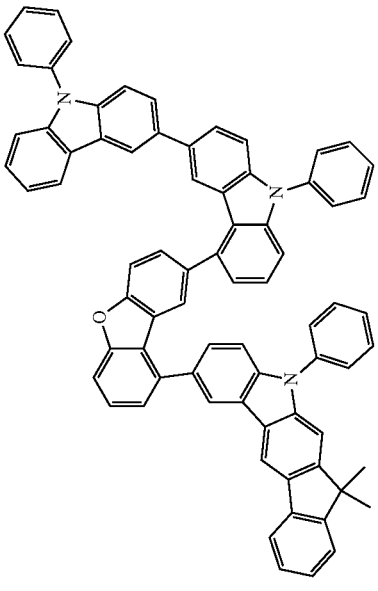 | 64% |
[1379585-25-7]

-continued

| | Reactant | Reactant | Product | Yield |
|---|---|---|---|---|
| f7 | | | | 67% |
| f8 | | | | 67% |

| Reactant | Reactant | Product | Yield |
|---|---|---|---|
| f9 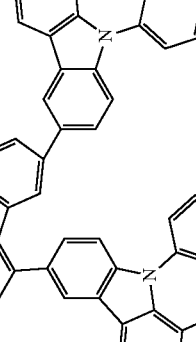 | 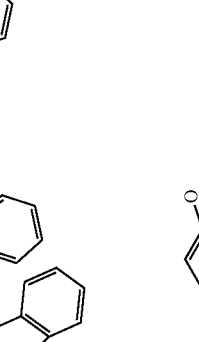 [1616232-07-5] |  | 63% |
| f10  | 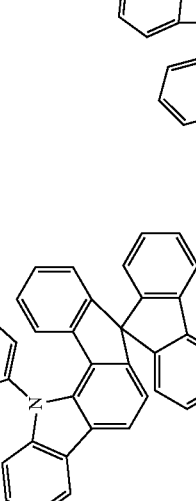 [1628070-74-5] |  | 65% |

-continued
| Reactant | Reactant | Product | Yield |
|---|---|---|---|
| f11 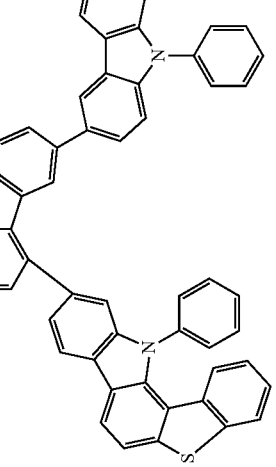 | 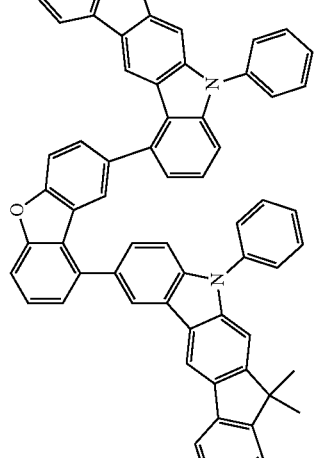 [1391729-62-6] | 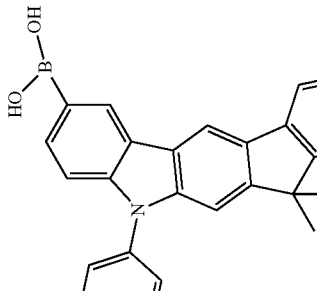 | 60% |
| f12 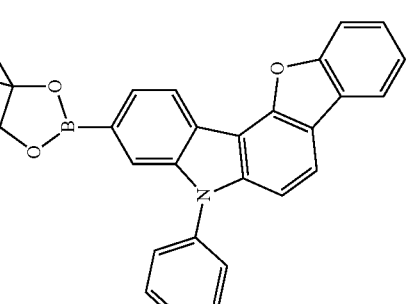 | 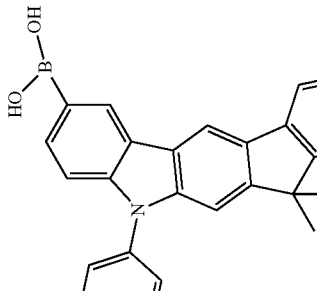 [1379585-25-7] | 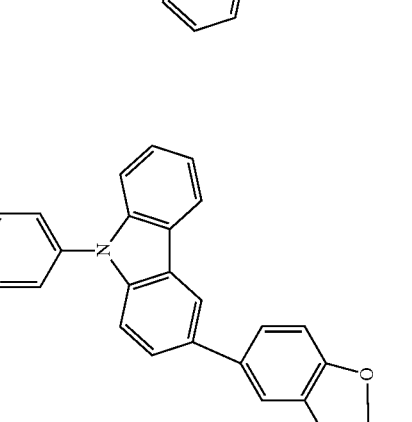 | 67% |

| Reactant | Reactant | Product | Yield |
|---|---|---|---|
| fl3 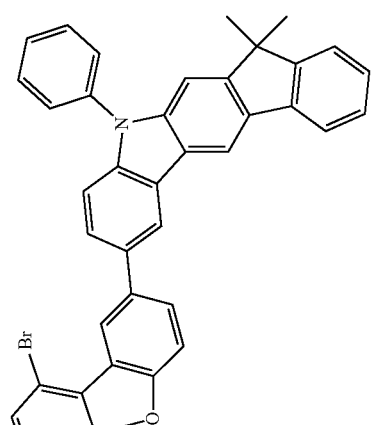 | 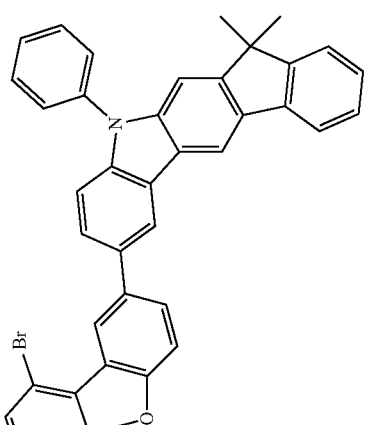 [162870-49-4] | 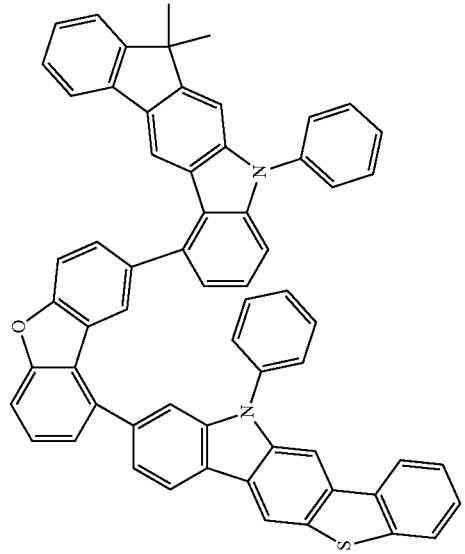 | 65% |
| fl4 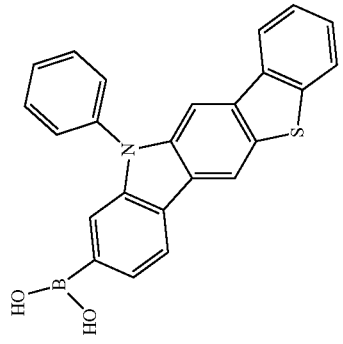 | 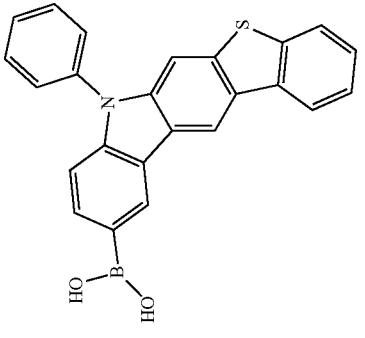 [161243-83-0] | 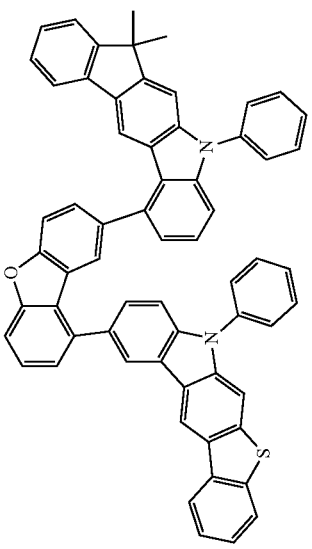 | 60% |

| | Reactant | Reactant | Product | Yield |
|---|---|---|---|---|
| f15 | | [1616232-07-5] | | 66% |
| f16 | | [1493715-37-9] | | 63% |

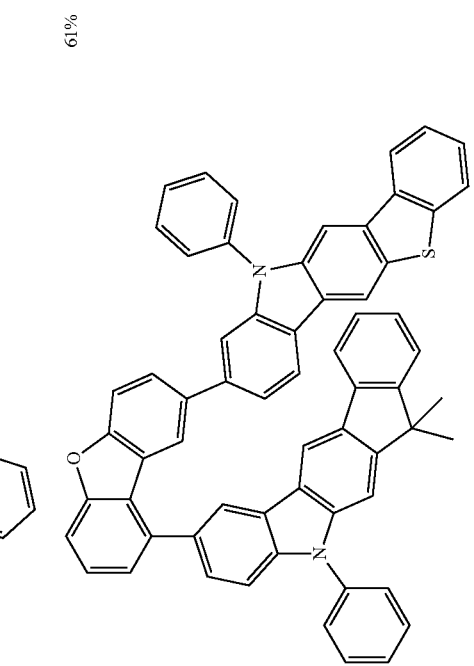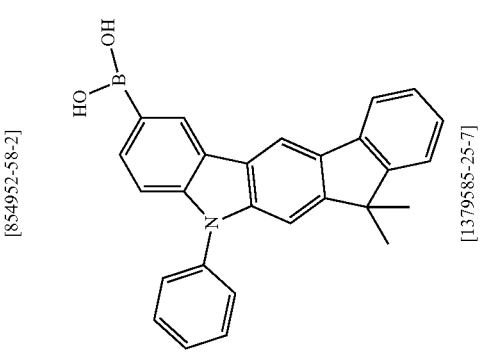

| | Reactant | Reactant | Product | Yield |
|---|---|---|---|---|
| f19 | 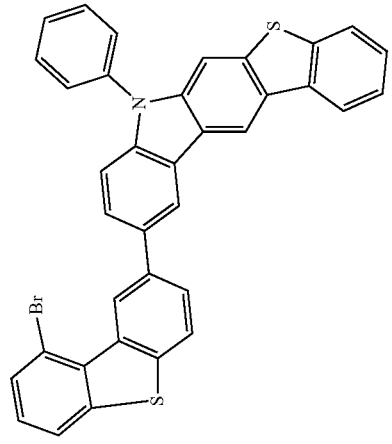 | 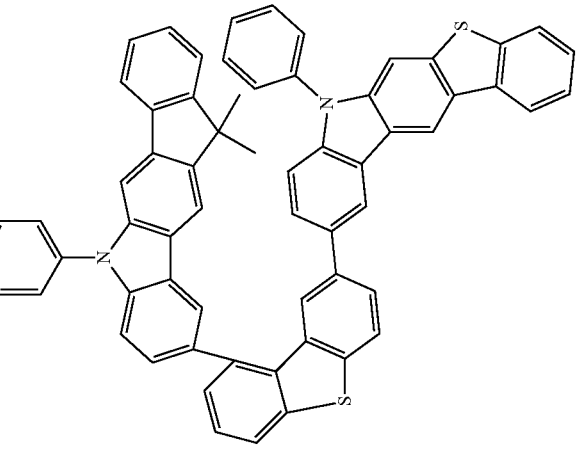 | 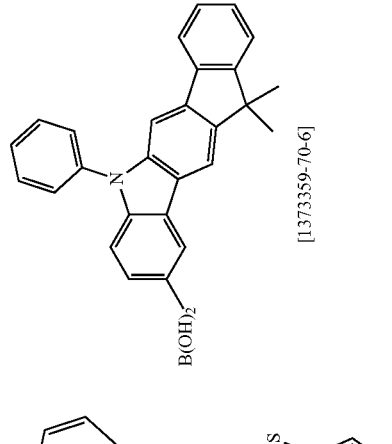 | 57% |
| f20 | 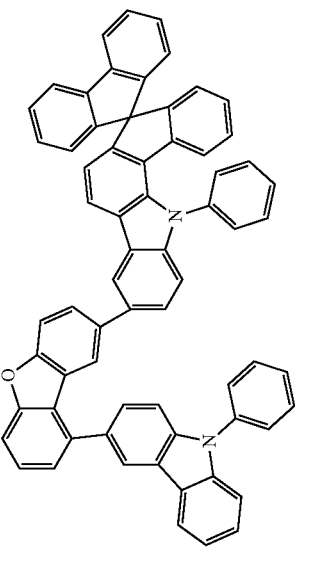 | 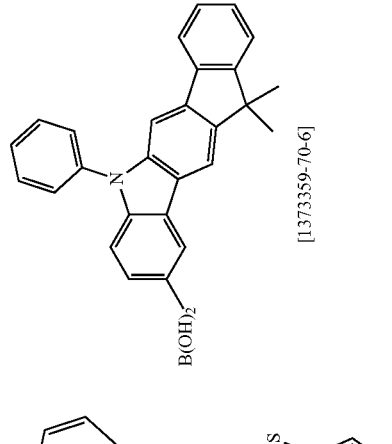 | 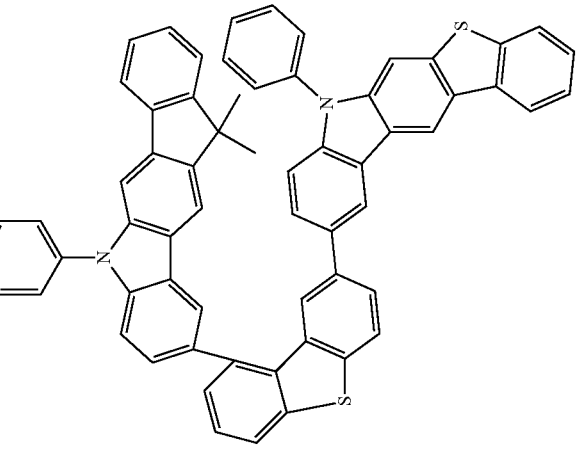 | 57% |

| | Reactant | Reactant | Product | Yield |
|---|---|---|---|---|
| f21 | 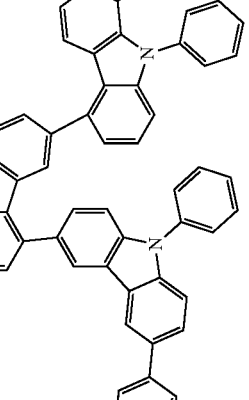 | 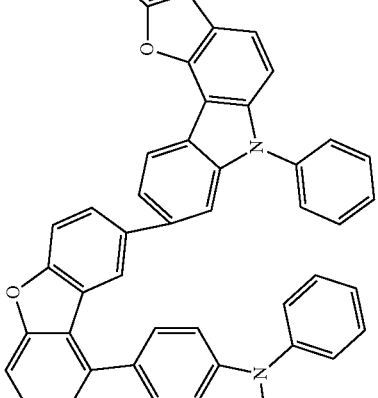 | 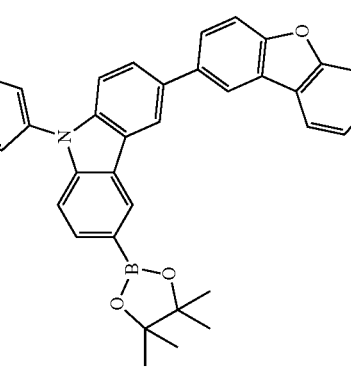 | 56% |
| f22 | 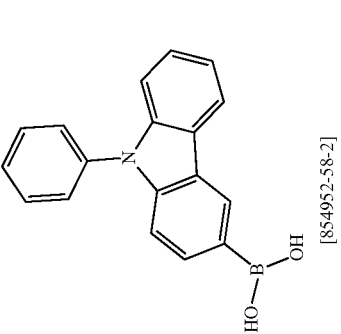 | 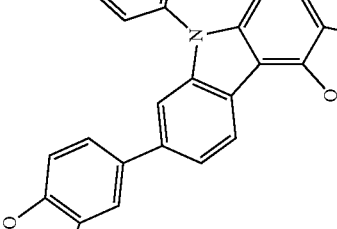 | 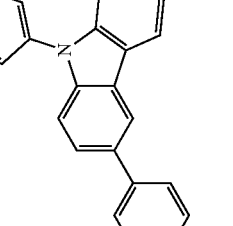 | 51% |

| Reactant | Reactant | Product | Yield |
|---|---|---|---|
| f23  | 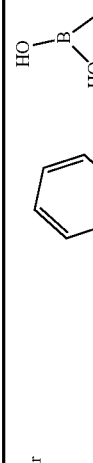 [1628070-49-4] |  | 53% |

-continued

| Reactant | Reactant | Product | Yield |
|---|---|---|---|
| f24 | [1612243-83-0] | | 56% |
| f25 | [1616232-07-5] | | 56% |

| Reactant | Reactant | Product | Yield |
|---|---|---|---|
| f26 | [1493715-37-9] | | 70% |
| f27 | [1391729-62-6] | | 73% |

-continued

| Reactant | Reactant | Product | Yield |
|---|---|---|---|
| f28 | [1333002-41-7] | | 72% |

| Reactant | Reactant | Product | Yield |
|---|---|---|---|
| f29 | [1547492-13-6] | | 72% |

| Reactant | Reactant | Product | Yield |
|---|---|---|---|
| f30 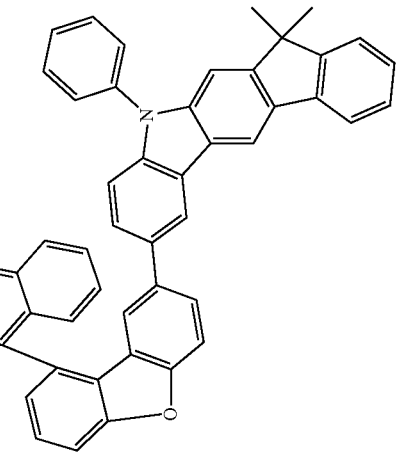 | [1493715-37-9] 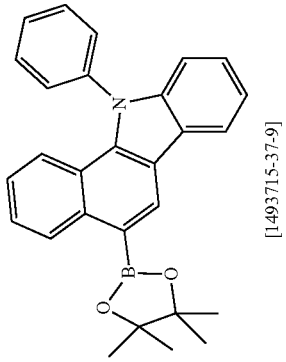 | 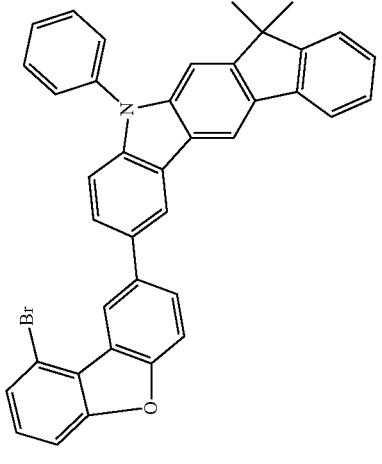 | 55% |

| Reactant | Reactant | Product | Yield |
|---|---|---|---|
| f31 | [1246562-39-9] | | 56% |
| f32 | [1379585-25-7] | | 60% |

| | Reactant | Reactant | Product | Yield |
|---|---|---|---|---|
| f33 | 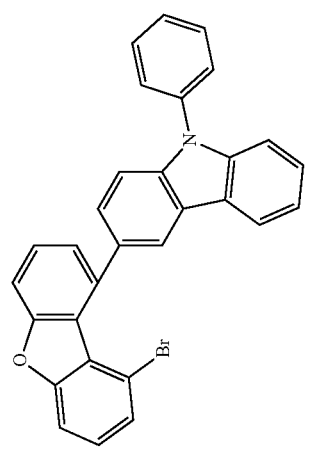 | 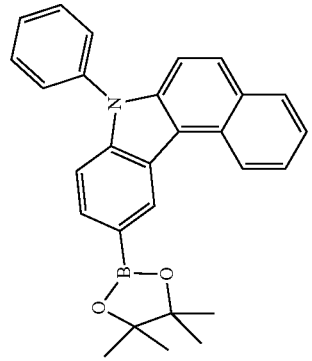 | 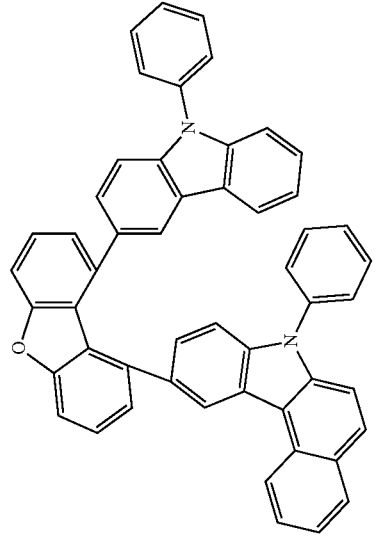 | 53% |
| f34 | 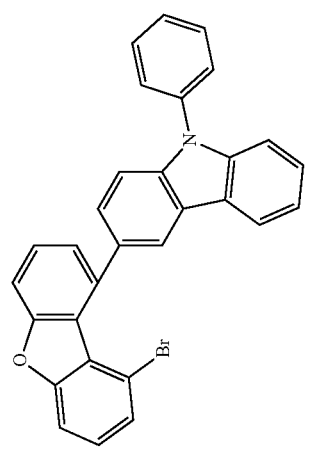 | 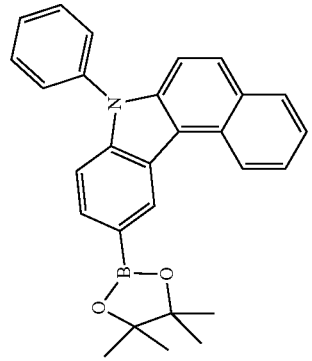 | 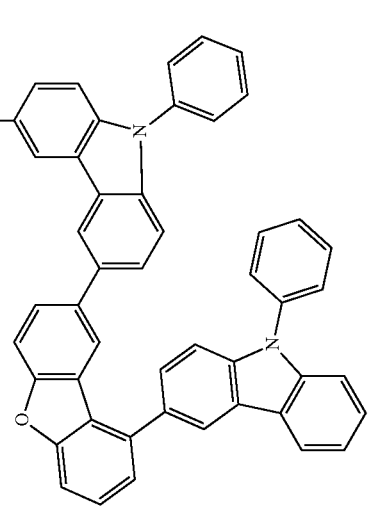 | 60% |

| Reactant | Reactant | Product | Yield |
|---|---|---|---|
| f35 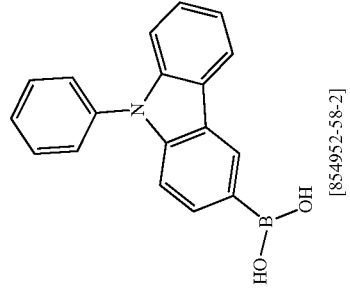 | 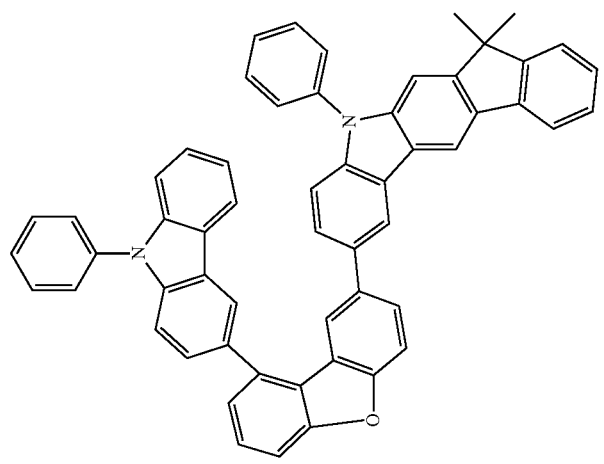 [854952-58-2] | 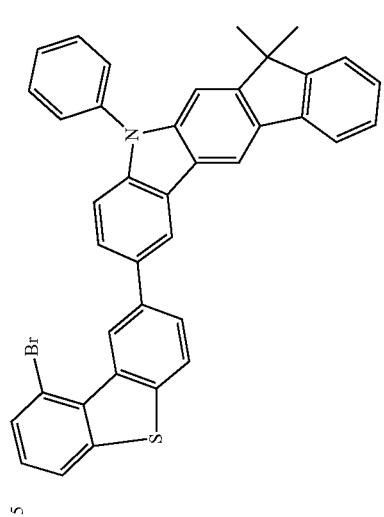 | 53% |

-continued
| Reactant | Reactant | Product | Yield |
|---|---|---|---|
| f36  |  [854952-58-2] |  | 50% | g) 12,12-Dimethyl-10-[9-(9-phenyl-9H-carbazol-3-yl)dibenzofuran-2-yl]-10,12-dihydro-10-azaindeno[2,1-b]fluorene

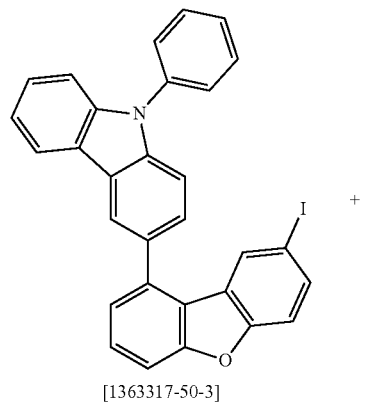

[1363317-50-3]

+

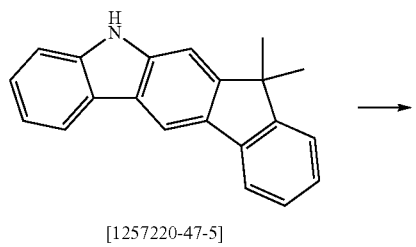

[1257220-47-5]

→

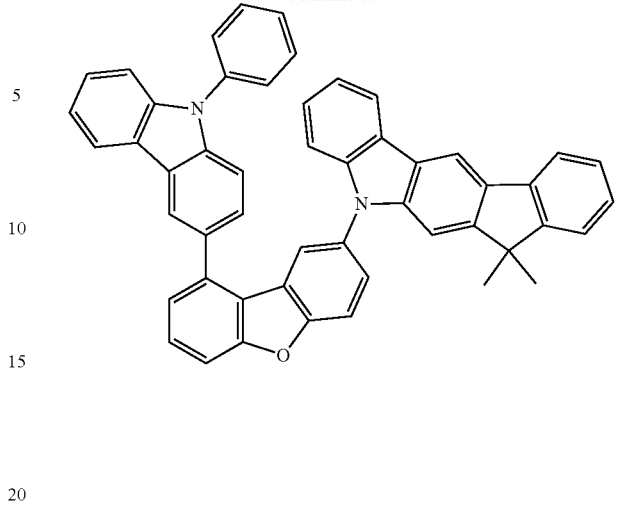

A degassed solution of 78 g (147 mmol) of 3-(8-iodo-1-dibenzofuranyl)-9-phenyl-9H-carbazole and 41.6 g (147 mmol) of 5,7-dihydro-7,7-dimethyl-indeno[2,1-b]carbazole indeno[21b]carbazole in 600 ml of toluene is saturated with $N_2$ for 1 h. Thereafter, first 2.09 ml of (8.6 mmol) $P(tBu)_3$ and then 1.38 g (6.1 mmol) of palladium(II) acetate are added to the solution, and then 17.7 g (185 mmol) of NaOtBu in the solid state are added. The reaction mixture is heated under reflux for 1 h. After cooling to room temperature, 500 ml of water were added cautiously. The aqueous phase was washed with 3×50 ml of toluene and dried over $MgSO_4$, and the solvent was removed under reduced pressure. Thereafter, the crude product was purified by chromatography using silica gel with heptane/ethyl acetate (20:1). The residue is recrystallized from toluene and finally sublimed under high vacuum (p=$5\times10^{-6}$ mbar). The yield is 85 g (123 mmol), corresponding to 85% of theory.

The following compounds are prepared in an analogous manner:

| | Reactant | Reactant | Product | Yield |
|---|---|---|---|---|
| g1 | | | | 60% |

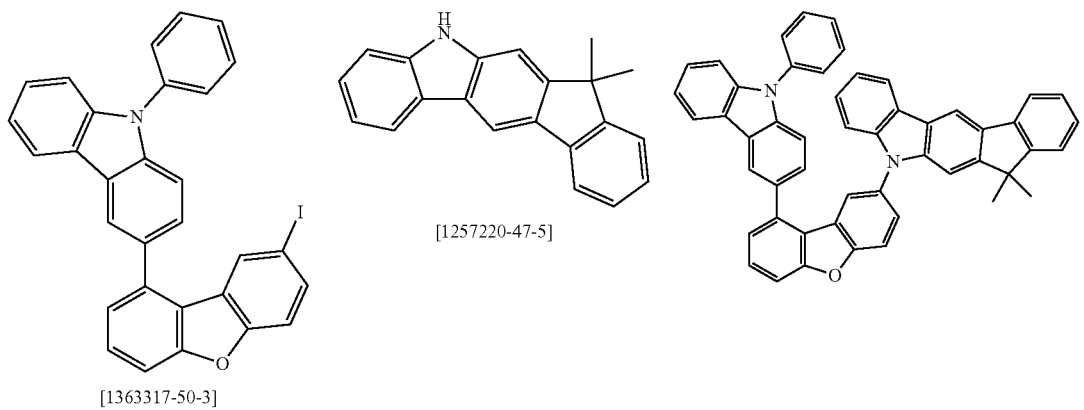

-continued

| Reactant | Reactant | Product | Yield |
|---|---|---|---|
| g2 [1363317-50-3] | [1060735-14-9] | | 57% |
| g3 [1363317-50-3] | [1024598-06-8] | | 59% |
| g4 [1363317-50-3] | [1439927-96-4] | | 63% |

-continued

| Reactant | Reactant | Product | Yield |
|---|---|---|---|
| g5 [1363317-50-3] | [1373281-72-1] | | 61% |
| g6 [1363317-50-3] | [1316311-27-9] | | 54% |
| g7 [1363317-50-3] | [1260228-95-2] | | 67% |

-continued
| | Reactant | Reactant | Product | Yield |
|---|---|---|---|---|
| g8 | 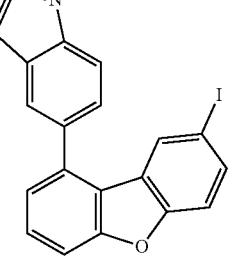 [1363317-50-3] | 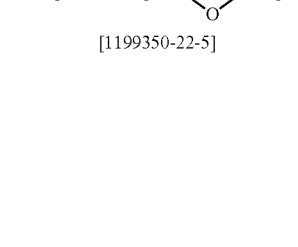 [1199350-22-5] | 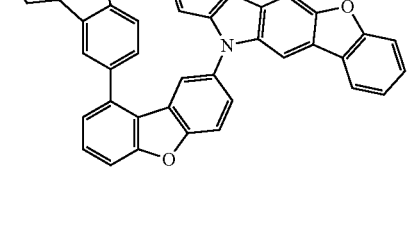 | 68% |
| g9 | 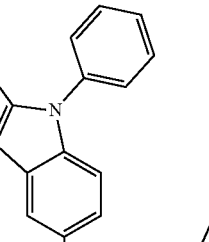 [1363317-50-3] | 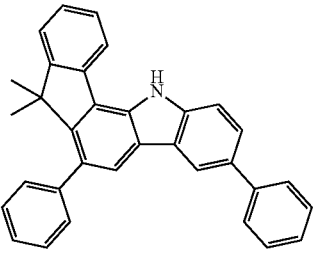 [1447708-58-8] | 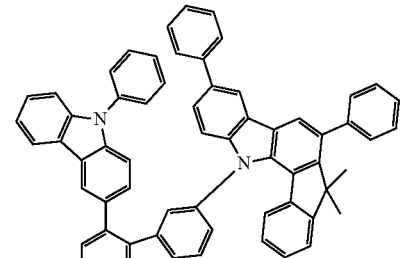 | 64% |
| g10 | 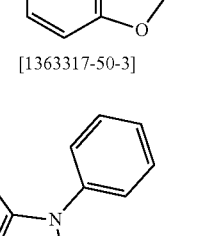 [1363317-50-3] | 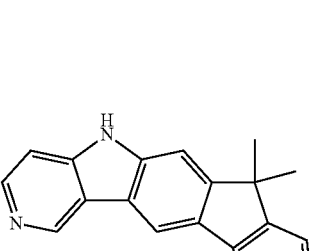 [1257248-14-8] | 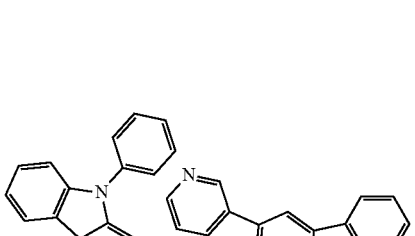 | 66% |
| g11 | 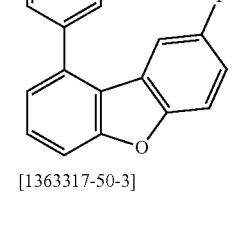 | 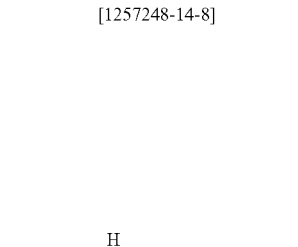 [103012-26-6] | 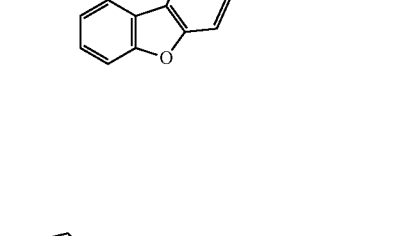 | 66% |

-continued

| Reactant | Reactant | Product | Yield |
|---|---|---|---|
| g12 | | | 64% |
| g13 | [1257220-47-5] | | 67% |
| g14 | [1257220-47-5] | | 81% |
| g15 | [1257220-47-5] | | 61% |

-continued

| Reactant | Reactant | Product | Yield |
|---|---|---|---|
| g16 | | | 60% |

Production of the OLEDs

In examples C1 to I11 which follow (see Tables 1 and 2), the data of various OLEDs are presented.

Pretreatment for Examples C1-I11: Glass plaques coated with structured ITO (indium tin oxide) of thickness 50 nm are treated prior to coating with an oxygen plasma, followed by an argon plasma. These plasma-treated glass plaques form the substrates to which the OLEDs are applied. The OLEDs basically have the following layer structure: substrate/hole injection layer (HIL)/hole transport layer (HTL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:PA:TEG1 (55%:35%:10%) mean here that the material IC1 is present in the layer in a proportion by volume of 55%, PA in a proportion of 35% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A) and the external quantum efficiency (EQE, measured in percent) are determined as a function of luminance, calculated from current-voltage-luminance characteristics (IUL characteristics) assuming Lambertian emission characteristics. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. CE1000 denotes the current efficiency which is achieved at 1000 cd/m$^2$. Finally, EQE1000 refers to the external quantum efficiency at an operating luminance of 1000 cd/m$^2$.

The data for the various OLEDs are collated in Table 2. Examples C1-C5 are comparative examples according to the prior art; examples I1-I11 show data of OLEDs of the invention. Some of the examples are elucidated in detail hereinafter, in order to illustrate the advantages of the OLED of the invention.

Use of Compounds of the Invention as Matrix Material of Phosphorescent OLEDs

The materials of the invention, when used as matrix material in combination with an electron-conducting compound (for example compound IC5 in the examples adduced below) in the emission layer (EML) in phosphorescent OLEDs, result in significant improvements over the prior art, particularly in relation to the power efficiency.

By use of the inventive compounds f35, f and f34, it is possible to observe an improvement in the power efficiency by about 5-10% compared to the compound from the prior art PA1 (comparison of examples C1 with examples I1, I2, I3). In addition, compound f35 has about a 10% improvement in power efficiency over PA5 (comparison of example C5 with example I1).

By use of the inventive compound g16, it is possible to observe an improvement in the power efficiency by about 5-10% compared to the compounds from the prior art PA2 and PA4 (comparison of examples C2 and C4 with example I4).

By use of the inventive compound g12, it is possible to observe an improvement in the power efficiency by about 10% compared to the compound from the prior art PA3 (comparison of example C3 with example I5).

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| C1 | HATCN 5 nm | SpMA1 230 nm | SpMA3 20 nm | IC5:PA1:TEG2 (30%:60%:10%) 30 nm | ST2 10 nm | ST2:LiQ (50%:50%) 30 nm | — |
| C2 | HATCN 5 nm | SpMA1 230 nm | SpMA3 20 nm | IC5:PA2:TEG2 (30%:60%:10%) 30 nm | ST2 10 nm | ST2:LiQ (50%:50%) 30 nm | — |
| C3 | HATCN 5 nm | SpMA1 230 nm | SpMA3 20 nm | IC5:PA3:TEG2 (30%:60%:10%) 30 nm | ST2 10 nm | ST2:LiQ (50%:50%) 30 nm | — |
| C4 | HATCN 5 nm | SpMA1 230 nm | SpMA3 20 nm | IC5:PA4:TEG2 (30%:60%:10%) 30 nm | ST2 10 nm | ST2:LiQ (50%:50%) 30 nm | — |
| C5 | HATCN 5 nm | SpMA1 230 nm | SpMA3 20 nm | IC5:PA5:TEG2 (30%:60%:10%) 30 nm | ST2 10 nm | ST2:LiQ (50%:50%) 30 nm | — |
| I1 | HATCN 5 nm | SpMA1 230 nm | SpMA3 20 nm | IC5:f39:TEG2 (30%:60%:10%) 30 nm | ST2 10 nm | ST2:LiQ (50%:50%) 30 nm | — |
| I2 | HATCN 5 nm | SpMA1 230 nm | SpMA3 20 nm | IC5:f:TEG2 (30%:60%:10%) 30 nm | ST2 10 nm | ST2:LiQ (50%:50%) 30 nm | — |
| I3 | HATCN 5 nm | SpMA1 230 nm | SpMA3 20 nm | IC5:f37:TEG2 (30%:60%:10%) 30 nm | ST2 10 nm | ST2:LiQ (50%:50%) 30 nm | — |
| I4 | HATCN 5 nm | SpMA1 230 nm | SpMA3 20 nm | IC5:g17:TEG2 (30%:60%:10%) 30 nm | ST2 10 nm | ST2:LiQ (50%:50%) 30 nm | — |
| I5 | HATCN 5 nm | SpMA1 230 nm | SpMA3 20 nm | IC5:g13:TEG2 (30%:60%:10%) 30 nm | ST2 10 nm | ST2:LiQ (50%:50%) 30 nm | — |
| I6 | HATCN 5 nm | SpMA1 230 nm | SpMA3 20 nm | IC5:f1:TEG2 (30%:60%:10%) 30 nm | ST2 10 nm | ST2:LiQ (50%:50%) 30 nm | — |
| I7 | HATCN 5 nm | SpMA1 230 nm | SpMA3 20 nm | IC5:f7:TEG2 (30%:60%:10%) 30 nm | ST2 10 nm | ST2:LiQ (50%:50%) 30 nm | — |
| I8 | HATCN 5 nm | SpMA1 230 nm | SpMA3 20 nm | IC5:f10:TEG2 (30%:60%:10%) 30 nm | ST2 10 nm | ST2:LiQ (50%:50%) 30 nm | — |
| I9 | HATCN 5 nm | SpMA1 230 nm | SpMA3 20 nm | IC5:f23:TEG2 (30%:60%:10%) 30 nm | ST2 10 nm | ST2:LiQ (50%:50%) 30 nm | — |
| I10 | HATCN 5 nm | SpMA1 230 nm | SpMA3 20 nm | IC5:f25:TEG2 (30%:60%:10%) 30 nm | ST2 10 nm | ST2:LiQ (50%:50%) 30 nm | — |
| I11 | HATCN 5 nm | SpMA1 230 nm | SpMA3 20 nm | IC5:g7:TEG2 (30%:60%:10%) 30 nm | ST2 10 nm | ST2:LiQ (50%:50%) 30 nm | — |

TABLE 2

Data of the OLEDs

| Ex. | U1000 (V) | LE1000 (lm/W) | CE1000 (cd/A) |
|---|---|---|---|
| C1 | 3.4 | 52 | 56 |
| C2 | 3.3 | 63 | 66 |
| C3 | 3.4 | 61 | 66 |
| C4 | 3.4 | 64 | 69 |
| C5 | 3.6 | 53 | 61 |
| I1 | 3.3 | 58 | 61 |
| I2 | 3.3 | 55 | 58 |
| I3 | 3.4 | 55 | 59 |
| I4 | 3.3 | 70 | 74 |
| I5 | 3.3 | 67 | 70 |
| I6 | 3.4 | 53 | 57 |
| I7 | 3.4 | 55 | 60 |
| I8 | 3.5 | 58 | 65 |
| I9 | 3.4 | 58 | 63 |
| I10 | 3.4 | 55 | 61 |
| I11 | 3.3 | 66 | 69 |

TABLE 3
Structural formulae of the materials for the OLEDs
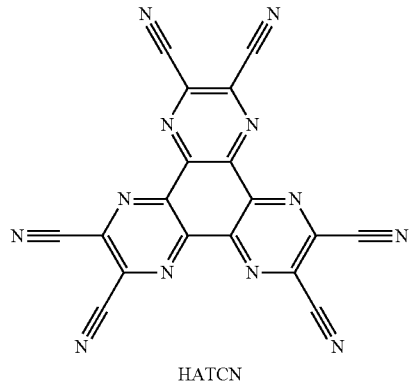
HATCN
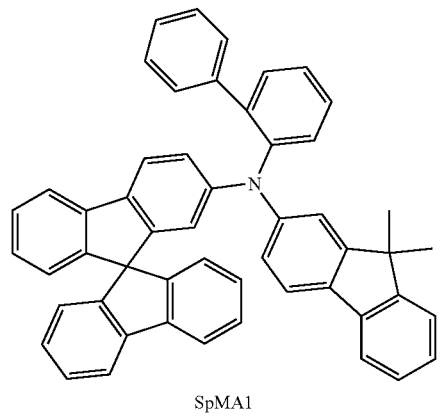 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
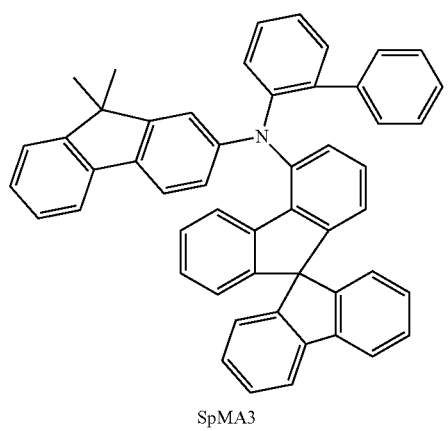 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
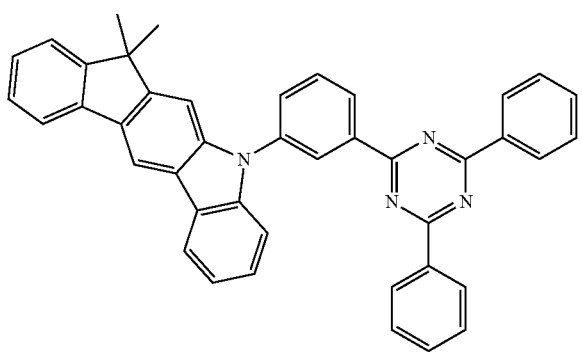
IC5
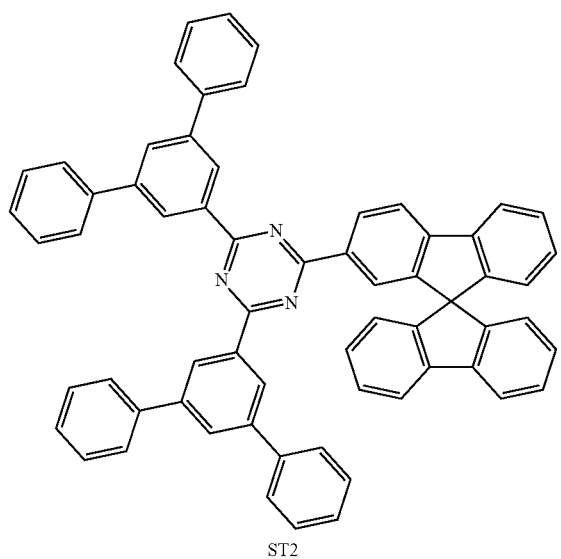
ST2
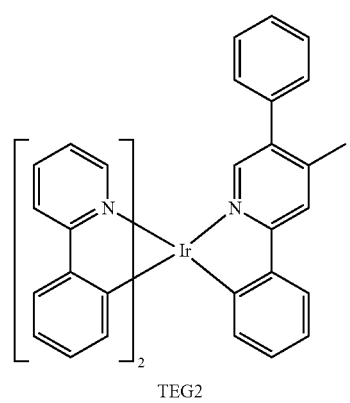
TEG2
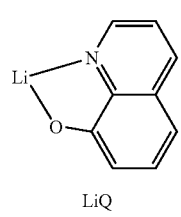
LiQ TABLE 3-continued
Structural formulae of the materials for the OLEDs
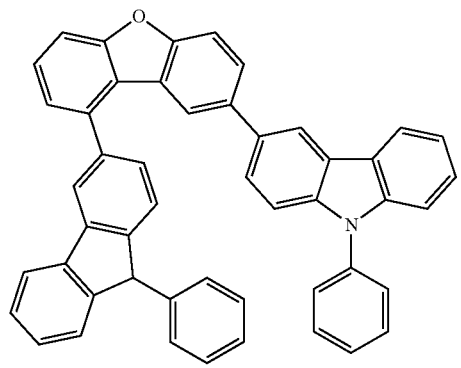
according to JP 2012-049518
PA1
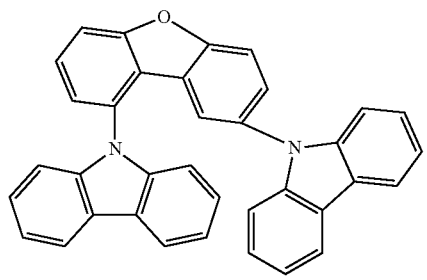
according to WO 2015/022988
PA2
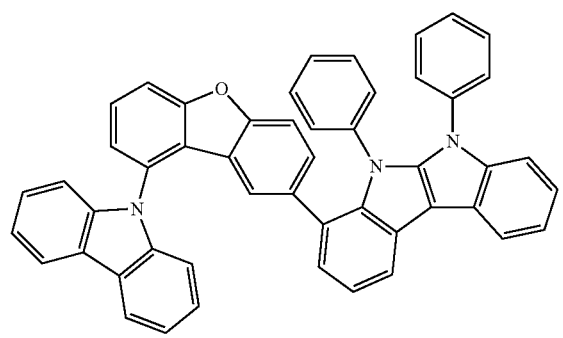
according to WO 2014/097866
PA3
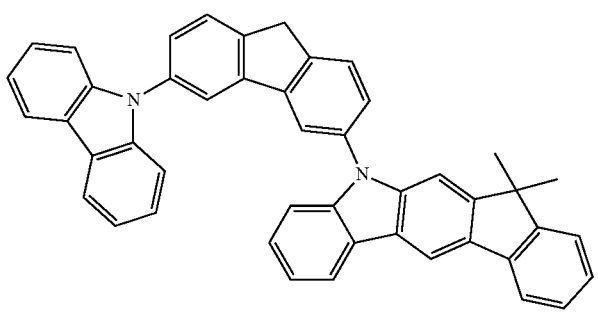
according to WO 2013/041176
PA4
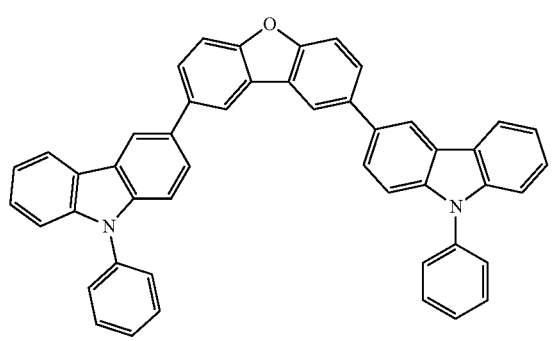
according to U.S. Pat. No. 7,935,434 B2
PA 5
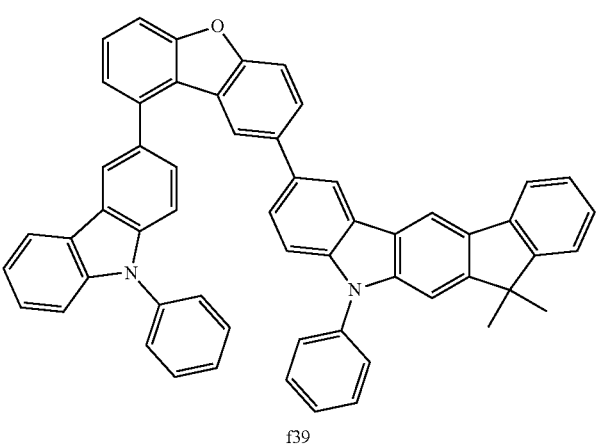 [SMILES: CC1(C)c2ccccc2-c2cc3c4cc(-c5ccc6oc7cccc(-c8ccc9c(c8)c8ccccc8n9-c8ccccc8)c7c6c5)ccc4n(-c4ccccc4)c3cc21]
f39

TABLE 3-continued
Structural formulae of the materials for the OLEDs
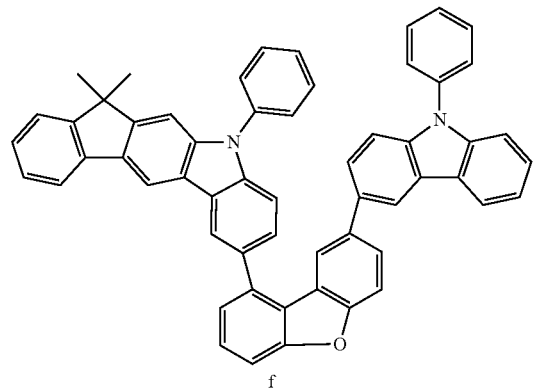 [SMILES: CC1(C)c2ccccc2-c2cc3c4cc(-c5cccc6oc7ccc(-c8ccc9c(c8)c8ccccc8n9-c8ccccc8)cc7c56)ccc4n(-c4ccccc4)c3cc21]
f
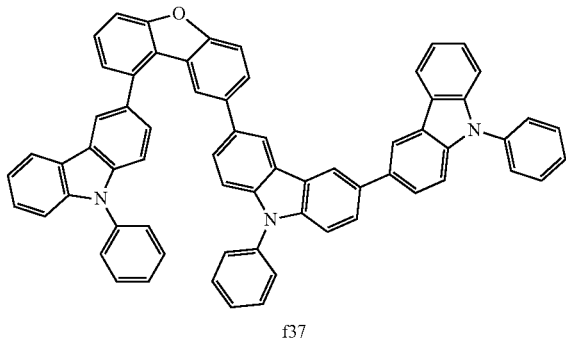 [SMILES: c1ccc(-n2c3ccccc3c3cc(-c4ccc5c(c4)c4cc(-c6ccc7oc8cccc(-c9ccc%10c(c9)c9ccccc9n%10-c9ccccc9)c8c7c6)ccc4n5-c4ccccc4)ccc32)cc1]
f37
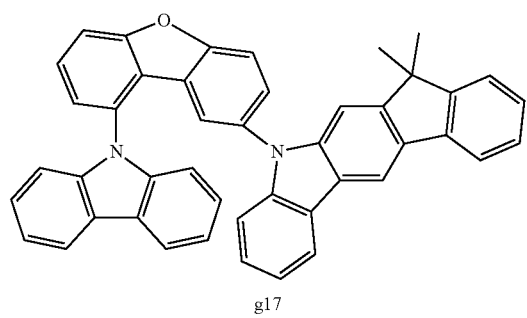 [SMILES: CC1(C)c2ccccc2-c2cc3c4ccccc4n(-c4ccc5oc6cccc(-n7c8ccccc8c8ccccc87)c6c5c4)c3cc21]
g17
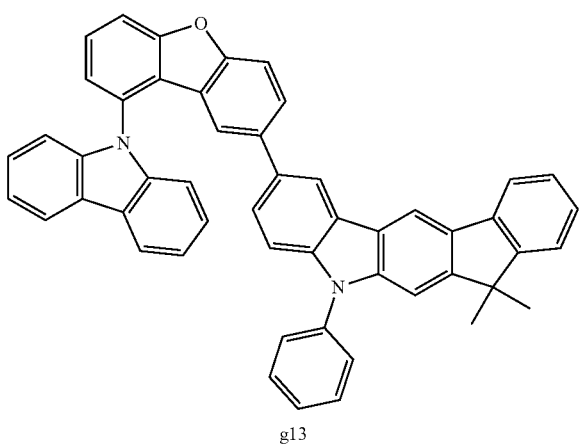 [SMILES: CC1(C)c2ccccc2-c2cc3c4cc(-c5ccc6oc7cccc(-n8c9ccccc9c9ccccc98)c7c6c5)ccc4n(-c4ccccc4)c3cc21]
g13
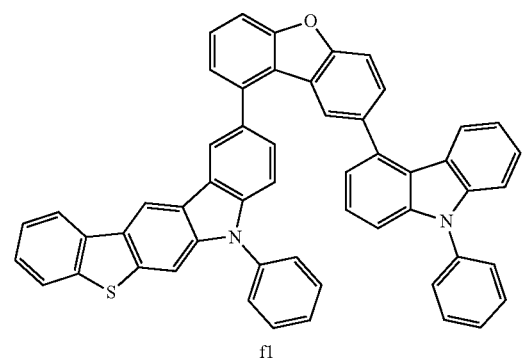 [SMILES: c1ccc(-n2c3ccc(-c4cccc5oc6ccc(-c7cccc8c7c7ccccc7n8-c7ccccc7)cc6c45)cc3c3cc4c(cc32)sc2ccccc24)cc1]
f1
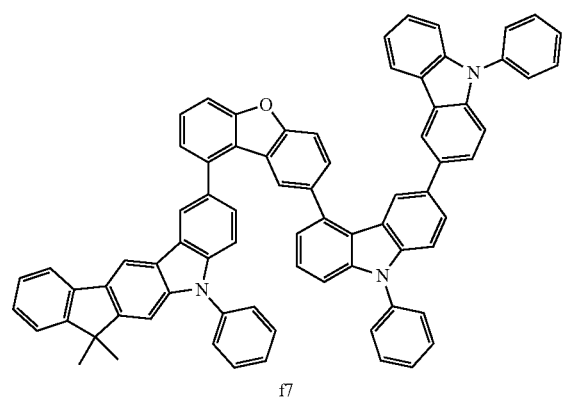 [SMILES: CC1(C)c2ccccc2-c2cc3c4cc(-c5cccc6oc7ccc(-c8cccc9c8c8cc(-c%10ccc%11c(c%10)c%10ccccc%10n%11-c%10ccccc%10)ccc8n9-c8ccccc8)cc7c56)ccc4n(-c4ccccc4)c3cc21]
f7

TABLE 3-continued
Structural formulae of the materials for the OLEDs
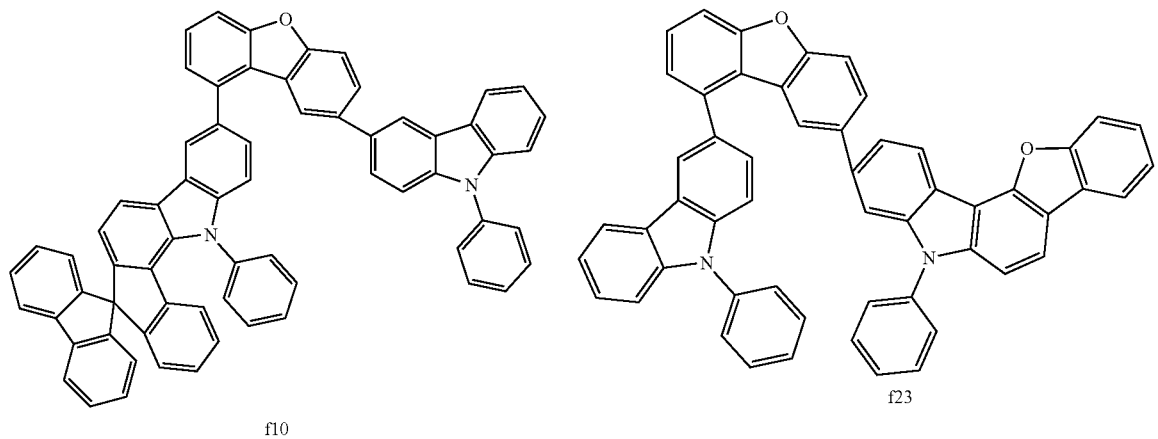
f10
f23
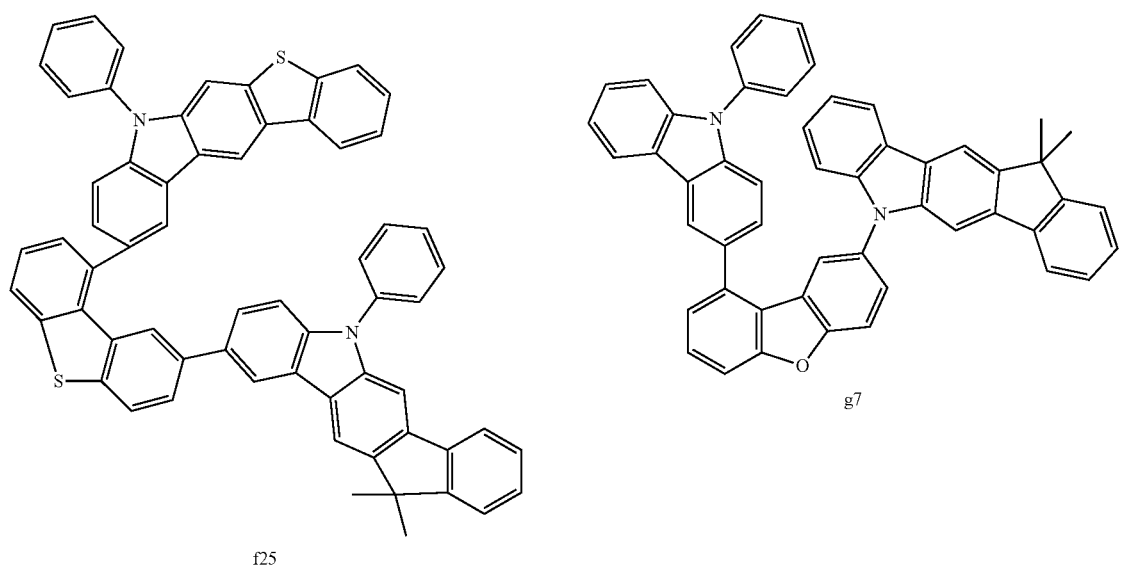
f25
g7
The invention claimed is:
1. A compound of formula (1), (2), (3) or (4),
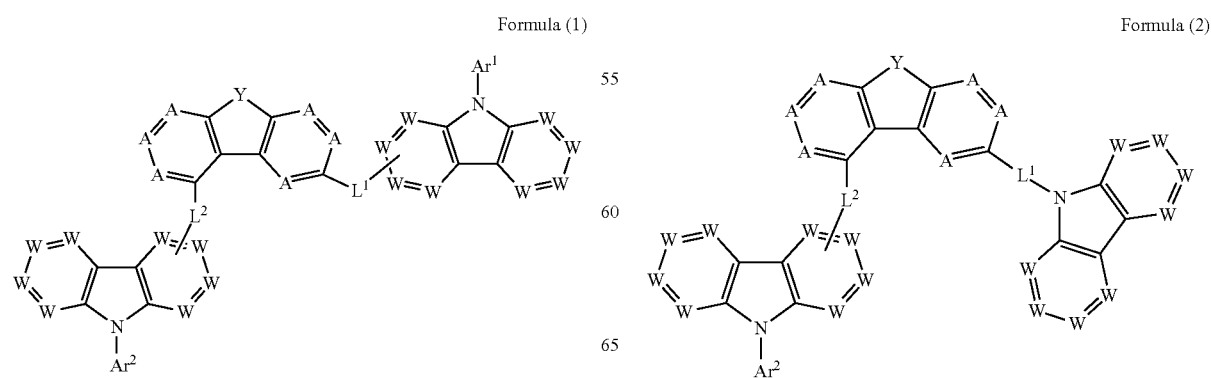
Formula (1)
Formula (2)
-continued Formula (3)

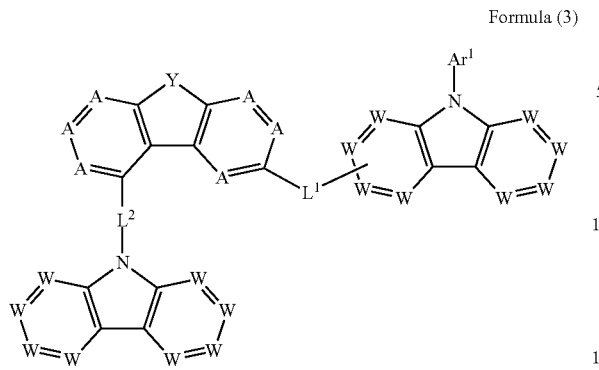

Formula (4)

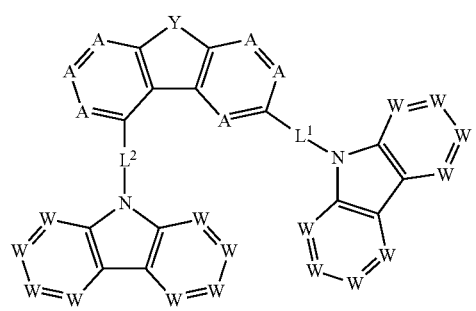

where the symbols used are as follows:

A is the same or different at each instance and is CR' or N, where not more than two A groups per cycle are N;

Y is O or S;

W is the same or different at each instance and is CR or N, where not more than two W groups per cycle are N and where W is C when an $L^1$ or $L^2$ group is bonded to this position, or two adjacent W groups together are a group of the following formula (5) or (6) and the remaining W are the same or different at each instance and are CR or N, where each of the two carbazolyl derivative groups in the compound of the formula (1), (2), (3) or (4) has not more than two groups of the formula (5) or formula (6):

Formula (5)

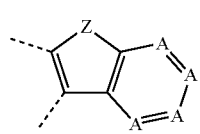

Formula (6)

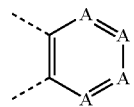

where the dotted bonds indicate the linkage of this group, A has definitions given above and Z is NR, $CR_2$, O or S;

with the proviso that one W group is CR and R at this position is a group of the following formula (7) or formula (8), or that two adjacent W groups are a group of the formula (5) or (6);

Formula (7)

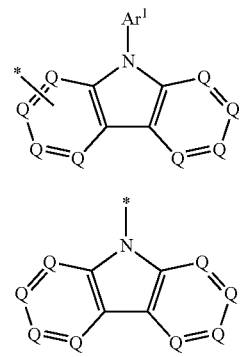

Formula (8)

Q is the same or different at each instance and is $CR^1$ or N, where not more than two Q groups per cycle are N and where Q is C when the single bond to formula (1), (2), (3) or (4) is at this position, or two adjacent Q groups together are a group of the formula (5) or (6) and the remaining Q are the same or different at each instance and are $CR^1$ or N, where the group of the formula (7) or formula (8) has not more than two groups of the formula (5) or formula (6), and A in the case of CR' is $CR^1$;

* is the single bond to formula (1), (2), (3) or (4);

$Ar^1$, $Ar^2$ is the same or different at each instance and is an aromatic ring system having 5 to 30 aromatic ring atoms or a dibenzofuran or dibenzothiophene group, where the aromatic ring system or the dibenzofuran or dibenzothiophene group may be substituted in each case by one or more nonaromatic R radicals;

$L^1$, $L^2$ in the formula (1), (2) or (4) is the same or different at each instance and is a single bond or an aromatic or heteroaromatic ring system which has 5 to 30 aromatic ring atoms and may be substituted by one or more R radicals;

$L^1$ in the formula (3) is a single bond or an aromatic or heteroaromatic ring system which has 5 to 30 aromatic ring atoms and may be substituted by one or more R radicals;

$L^2$ in the formula (3) is a single bond or an aromatic ring system which has 6 to 30 aromatic ring atoms and may be substituted by one or more R radicals;

R, R' is the same or different at each instance and is selected from the group consisting of H, D, F, Cl, Br, I, CN, $NO_2$, $N(R^1)_2$, $C(=O)R^1$, $P(=O)(R^1)_2$ $P(R^1)_2$, $B(R^1)_2$, $Si(R^1)_3$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^1$ radicals, where one or more nonadjacent $CH_2$ groups may be replaced by $R^1C=CR^1$, $Si(R^1)_2$, C=O, C=S, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^1$ radicals, or an aryloxy or heteroaryloxy group which has 5 to 40 aromatic ring atoms and may be substituted by one or more $R^1$ radicals; at the same time, it is optionally possible for two R substituents bonded to the same carbon atom or to adjacent carbon atoms, or two R' substituents bonded to adjacent carbon atoms, to form a monocyclic or polycyclic, aliphatic, aromatic or heteroaromatic ring system which may be substituted by one or more $R^1$ radicals;

$R^1$ is the same or different at each instance and is selected from the group consisting of H, D, F, Cl, Br, I, CN, $N(R^2)_2$, $C(=O)R^2$, a straight-chain alkyl group having 1 to 10 carbon atoms or a branched or cyclic alkyl group having 3 to 10 carbon atoms or an alkenyl group having 2 to 10 carbon atoms, each of which may be substituted by one or more $R^2$ radicals, where one or more hydrogen atoms may be replaced by D, F, Cl, Br, I or CN, or an aromatic or heteroaromatic ring system which has 5 to 40 aromatic ring atoms and may be substituted in each case by one or more $R^2$ radicals; at the same time, it is optionally possible for two $R^1$ substituents bonded to the same carbon atom or to adjacent carbon atoms to form a monocyclic or polycyclic, aliphatic, aromatic or heteroaromatic ring system which may be substituted by one or more $R^2$ radicals;

$R^2$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, CN and which may be substituted by one or more alkyl groups each having 1 to 4 carbon atoms; at the same time, it is possible for two or more adjacent $R^2$ substituents together to form a mono- or polycyclic, aliphatic ring system.

2. The compound according to claim 1, wherein $L^1$ is a single bond.

3. The compound according to claim 1, wherein $L^1$ and $L^2$ are each a single bond.

4. The compound according to claim 1, wherein at least one of the two carbazole groups or carbazole derivatives is joined by the 3 position.

5. The compound according to claim 1, wherein the $Ar^1$ and $Ar^2$ groups are the same or different at each instance and are selected from the group consisting of phenyl, ortho-, meta- or para-biphenyl, terphenyl, quaterphenyl, 1-, 2-, 3- or 4-fluorenyl, 1-, 2-, 3- or 4-spirobifluorenyl, 1-, 2-, 3- or 4-dibenzofuranyl and 1-, 2-, 3- or 4-dibenzothienyl, each of which may be substituted by one or more nonaromatic R radicals.

6. The compound according to claim 1, wherein R and R' are selected from the group consisting of H, D, F, CN, $N(R^1)_2$, $C(=O)R^1$, $P(=O)(R^1)_2$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^1$ radicals, where one or more nonadjacent $CH_2$ groups may be replaced by O and where one or more hydrogen atoms may be replaced by D or F, or an aromatic or heteroaromatic ring system which has 5 to 24 aromatic ring atoms and may be substituted in each case by one or more $R^1$ radicals; at the same time, it is optionally possible for two R substituents bonded to the same carbon atom or to adjacent carbon atoms to form a monocyclic or polycyclic, aliphatic, aromatic or heteroaromatic ring system which may be substituted by one or more $R^1$ radicals.

7. A process for preparing a compound according to claim 1 comprising reacting an optionally substituted 1,8-dihalodibenzofuran or 1,8-dihalodibenzothiophene with a carbazole derivative, followed by reaction with the other carbazole derivative, where the reactions with the carbazole derivatives are each C—C couplings or C—N couplings.

8. A formulation comprising at least one compound according to claim 1 and a solvent and/or at least one further organic or inorganic compound.

9. A method comprising utilizing the compound according to claim 1 in an electronic device.

10. An electronic device selected from the group consisting of organic electroluminescent devices, organic integrated circuits, organic field-effect transistors, organic thin-film transistors, organic light-emitting transistors, organic solar cells, organic dye-sensitized solar cells, organic optical detectors, organic photoreceptors, organic field-quench devices, light-emitting electrochemical cells, organic laser diodes and organic plasmon emitting devices, comprising at least one compound according to claim 1.

11. The Electronic device according to claim 10, wherein the electronic device is an organic electroluminescent device and the compound is used as matrix material for fluorescent or phosphorescent emitters in an emitting layer and/or as electron transport or hole blocker material in an electron transport layer and/or in a hole-blocking layer and/or as a hole transport material in a hole transport or hole injection layer and/or as an exciton blocker material in an exciton blocker layer.

* * * * *